United States Patent
Sun et al.

(10) Patent No.: US 6,552,053 B2
(45) Date of Patent: Apr. 22, 2003

(54) CONTROLLING ATTENTION AND MEMORY BY ALTERING NEURONAL CARBONIC ANHYDRASE ACTIVITY

(75) Inventors: Miao-Kun Sun, Bethesda, MD (US); Daniel L. Alkon, Bethesda, MD (US); Wei-Qin Zhao, Bethesda, MD (US)

(73) Assignee: The United States of America as represented by the Secretary of Health and Human Services, Washington, DC (US)

( * ) Notice: Subject to any disclaimer, the term of this patent is extended or adjusted under 35 U.S.C. 154(b) by 0 days.

(21) Appl. No.: 09/875,283

(22) Filed: Jun. 7, 2001

(65) Prior Publication Data

US 2002/0107267 A1 Aug. 8, 2002

Related U.S. Application Data

(60) Provisional application No. 60/209,790, filed on Jun. 7, 2000.

(51) Int. Cl.[7] .............................................. A61K 31/41
(52) U.S. Cl. ....................................................... 514/363
(58) Field of Search ........................................ 514/363

(56) References Cited

PUBLICATIONS

Lindskog S., Structure and mechanism of carbonic anhydrase, Pharmacol Ther. 1997;74(1):1–20.

Sun, M.–K., Nelson, T.J., Xu, H., and Alkon, D.L., Calexcitin transformation of GABAergic synapses: from excitation filter to amplifier, Proc. Natl. Acad. Sci. USA 96: 7023–7028, 1999.

Sun, M.–K., Nelson, T.J., Xu, H., and Alkon, D.L., Theta Rhythm of Hippocampal CA1 Neuron Activity: Gating by GABAergic Synaptic Depolarization, J Neurophysiol. Jan. 2001;85(1):269–279.

Sun, M.–K., Pharmacology of reticulospinal vasomotor neurons in cardiovascular regulation, Phanmacol. Rev. 48: 465–494, 1996.

*Primary Examiner*—William R. A. Jarvis
(74) *Attorney, Agent, or Firm*—Venable; Michael A. Gollin

(57) ABSTRACT

The invention provides a method for modulating attentive cognition comprising administering a compound that alters intraneuronal carbonic anhydrase activity thereby affecting establishment of a theta rhythm. The metabolic pathway of the compound preferably involves bicarbonate-mediated GABAergic depolarization. The term "attentive cognition" is meant to encompass memory formation, learning, spatial memory, and attention. The modulating may be stimulating, or the compound may have the multiple effects of inhibiting intraneuronal carbonic anhydrase activity, establishment of a theta rhythm, and memory acquisition. The invention further provides a method of modulating memory and attention comprising switching theta rhythm on and off, the switching comprising potentiating or inhibiting intraneuronal carbonic anhydrase activity.

26 Claims, 40 Drawing Sheets

CONTROL

CCH

BIC+CCH

CONTROL

-70 mV -

CCH

-70 mV -

CONTROL

CONTROL

CONTROLLING ATTENTION AND MEMORY BY ALTERING NEURONAL CARBONIC ANHYDRASE ACTIVITY

This application claims the benefit of provisional application USSN 60/209,790, filed Jun. 7, 2000, incorporated herein by reference.

BACKGROUND OF THE INVENTION

This invention relates to methods for modulating attention, learning, and memory by controlling carbonic anhydrase activity. More particularly, the invention involves administering a compound that alters carbonic anhydrase activity in the brain thereby affecting establishment of a theta rhythm in the brain.

Acetazolamide is a generic drug manufactured in forms of capsule, tablets or injectable preparations. Inhibition of carbonic anhydrase activity by acetazolamide is a therapeutic approach in use or suggested for several indications, including glaucoma, conjunctive heart failure, mountain sickness, sleep apnea and petit mal seizures (epilepsy), and body fluid retention. These therapeutic avenues are diverse and none of them suggests any cognitive impacts of regulating carbonic anhydrase activity.

Hippocampal theta (θ) rhythm (synchronized neuronal discharge) is believed to play a critical role in information processing and memory consolidation during exploratory behavior. Theta activity depends on cholinergic inputs and θ discharges of GABAergic interneurons, and can be induced e.g. by a cholinergic receptor agonist (carbachol). GABA acts as an inhibitor of action potentials by keeping the GABA-$Cl^-$ channel open. This channel is an anion transporter, exchanging $Cl^-$ for $HCO_3^-$. Maintaining the open channel allows $Cl^-$ to flow into the cell to hyperpolarize the membrane potential. Cholinergic components depolarize the membrane potential, and if threshold is reached an action potential is created. It is believed that the synchronized depolarization and excitation creates an oscillating membrane potential leading to θ activity, but the mechanism has remained unknown. GABAergic depolarization can be induced by enhancing $HCO_3^-$ conductance through $GABA_A$ receptor-channels in adult hippocampal cells, a response sensitive to carbonic anhydrase inhibitors (Kaila '93). However, no association has previously been identified between carbonic anhydrase inhibition at the cellular-electrophysiological level on the one hand, and a reduction in theta rhythm on the other.

There have been few medications suitable for improving attention in those who need it, and no effective medications for those who need to suppress learning painful memories. There is a need to elucidate a simple biochemical target for controlling the extremely complicated brain-wide effect of theta rhythm, and the even more complex events leading to attention and learning. Such a target would be invaluable in identifying specific compounds for achieving the desired cognitive effects.

This invention differs from the prior art in modifications, which were not previously known or suggested, including the use of carbonic anhydrase regulators to alter theta rhythm and produce cognitive effects in mammals. The methods of the invention provide advantages that were not previously appreciated, such as the ability to selectively enhance attention and learning. This invention satisfies a long felt need for compounds that selectively enhance or inhibit attention and learning.

The widespread use of acetazolamide, with no substantial cognitive side effects reported, makes it surprising to discover that the compound does inhibit spatial learning in animals, and presumably in humans. This invention thus identifies a previously unrecognized problem, and shows how to solve it, e.g. by careful dosing regimens of acetazolamide so as to reduce its cognitive side effects.

SUMMARY OF THE INVENTION

Acetazolamide, a drug commonly used for glaucoma and diuresis, has been found to specifically block acquisition of new memories. Post-traumatic stress disorder involves learning new contexts for traumatic memories. These new contexts would be blocked during the administration of acetazolamide. Thus, acetazolamide can be used for short-term memory suppression, for example to prevent post traumatic stress syndrome during a period of trauma.

More generally, based on comprehensive electrophysiologic studies of GABAergic depolarization of CA1 hippocampal cells, we have implicated bicarbonate conductance enhancement as critical for theta rhythm and spatial maze learning. Bicarbonate-mediated GABAergic depolarization mediated by carbonic anhydrase (blocked by acetazolamide) is a target for drugs that either block or enhance new memory formation. Blocking drugs would have application in post-traumatic stress disorders and related diseases. Cognitive enhancing drugs would have wide application in the treatment of neurodegenerative disorders, especially those involving dementia.

Surprisingly, according to the invention, the GABAergic transformation is associated with establishment of a theta rhythm, and both phenomena can be controlled together by modifying neuronal carbonic anhydrase activity. Although it was previously thought that the transformation was related to attention, and that the theta rhythm was associated with attention, there was no teaching that the two were intimately connected and subject to common control via carbonic anhydrase inhibitors or activators.

The invention relates to a method for blocking associative memory acquisition comprising determining a need for blocking, and administering an inhibitor, such as acetazolamide, of carbonic anhydrase activity in the brain, thereby blocking the memory acquisition. The method can also be used for suppressing attention, learning and/or memory formation in a mammal comprising determining a need for suppressing, and administering an inhibitor of carbonic anhydrase activity in an amount effective to inhibit carbonic anhydrase activity in the brain, preferably in neurons. The inhibitor may be selected from the group consisting of acetazolamide, benzolamide, and analogs thereof. An analog is a molecule having a structure function relationship similar to the named compound that allows it to bind to and inhibit carbonic anhydrase in the brain. Although, the inhibitor prevents establishment of a theta rhythm during learning, it does not affect memory retrieval from formed memories, or sensory or locomotor behaviors.

In yet another aspect of the invention, the method can be used for improving attention and/or memory acquisition in a patient comprising determining the need for improved attention and/or memory acquisition, and administering to the patient a stimulator of intraneuronal carbonic anhydrase activity in an amount sufficient to stimulate intraneuronal carbonic anhydrase activity. The patient may be healthy, i.e. have no neurodegenerative disorder or the patient may suffer from a neurodegenerative disease. The invention may also be used for treating a neurodegenerative disorders comprising administering an effective amount of a stimulator of intraneuronal carbonic anhydrase activity. The cognitive ability may be enhanced. The neurodegenerative disease can also be dementia.

The invention further provides a method for modulating attentive cognition comprising administering a compound that alters intraneuronal carbonic anhydrase activity in an amount sufficient to affect the establishment of a theta rhythm. The theta rhythm can be affected by modulating bicarbonate-mediated GABAergic depolarization. Moreover, the attentive cognition may be selected from memory formation, learning, spatial memory, and attention. In one aspect the modulating is stimulating. The compound can be administered in an amount sufficient to inhibit intraneuronal carbonic anhydrase activity, establish of a theta rhythm, and suppress memory acquisition. The compound may also be administered in an amount that does not affect memory retrieval. Moreover, the suppression may occur about one half to one hour after administering the inhibitor compound.

The term "attentive cognition" is meant to encompass memory formation, learning, spatial memory, and attention. The inhibiting of carbonic anhydrase is preferably selective in that it reduces memory acquisition, but not memory retrieval.

In another aspect of the invention, the method may be used for modulating memory and attention by switching theta rhythm on and off to modulate intraneuronal carbonic anhydrase activity, comprising administering a compound that modulates intraneuronal carbonic anhydrase activity. The modulating intraneuronal carbonic anhydrase activity may comprise increasing intraneuronal carbonic anhydrase activity or alternatively decreasing intraneuronal carbonic anhydrase activity.

In yet a further aspect, the invention relates to a method of altering memory acquisition by modulating $HCO_3^-$ conductance comprising administering a compound that modulates carbonic anhydrase activity the brain in an amount sufficient to alter $HCO_3^-$ conductance. The compound can be administered in an amount sufficient to modulate the $HCO_3^-$ current relative to the $Cl^-$ and $K^+$ currents. The invention also relates to a method of modulating establishment of a theta rhythm comprising administering a compound that modulates intraneuronal carbonic anhydrase activity in an amount sufficient to control the occurrence of synaptic transformation. Another aspect of the invention relates to a method for treating a neurological disorder comprising administering a compound that stimulates intraneuronal carbonic anhydrase activity in an amount sufficient to control the occurrence of synaptic transformation. The neurological disorder can be associated with a disorder affecting cognition such as stroke, hypoxia, and ischemia, and others known to practitioners.

The invention may also relate to a method for screening compounds for usefulness for cognitive enhancement therapy comprising measuring the effect of a compound on carbonic anhydrase activity in neurons, in tissue, in animals, or in cell culture, and selecting those compounds that stimulate carbonic anhydrase activity. In addition, the invention provides a method for screening compounds for usefulness for cognitive enhancement therapy comprising measuring the effect of a compound on theta rhythm in neurons, in tissue, in animals, or in cell culture and selecting those that establish a theta rhythm.

Finally, the invention provides a method of blocking synaptic transformation of inhibitory postsynaptic potentials into excitatory postsynaptic potentials in GABAergic synapses in a mammalian brain, comprising determining a need for blocking, and administering to the brain an inhibitor of intraneuronal carbonic anhydrase activity, thereby blocking the synaptic transformation in the synapses. The inhibitor may neutralize the excitatory effects of a memory related signaling protein. The memory related signaling protein can be calexcitin and the inhibitor can be acetazolamide or an analog of acetazolamide. The metabolic pathway of the compound preferably involves bicarbonate-mediated GABAergic depolarization. The affected synapses may be found in circuits throughout the brain, including pyramidal cells in the hippocampal region.

The invention also relates to a pharmaceutical product comprising a dosage form comprising a pharmaceutically acceptable carrier and a compound that inhibits or stimulates carbonic anhydrase activity in the brain, associated with labeling indicating use of the dosage form for cognitive effects.

Further objectives and advantages will become apparent from a consideration of the description, drawings, and examples.

BRIEF DESCRIPTION OF THE DRAWINGS

The invention is better understood by reading the following detailed description with reference to the accompanying figures, in which like references refer to like elements throughout, and in which:

FIGS. 1A1 to 1A3, 1B1 to 1B4 and 1C1 to 1C4 show the effects of carbachol (CCH)-induced θ oscillations of hippocampal CA1 field potential and of membrane potential of CA1 pyramidal cells, which depend on activation of GABAergic inputs.

FIGS. 2A1 to 2A5, 2B and 2C demonstrate the effects of carbachol (CCH)-induced θ oscillations of hippocampal CA1 field potential and of membrane potential of CA1 pyramidal cells, which are associated with GABAergic postsynaptic depolarization.

FIGS. 3A1 to 3A3, 3B1 to 3B3 and 3C1 to 3C3 show carbachol shifts reversal potentials of GABAergic postsynaptic responses in hippocampal CA1 pyramidal cells.

FIGS. 4A1 to 4A3, and 4B1 to 4B3 demonstrate the effects of carbachol (CCH)-induced θ oscillations of hippocampal CA1 field potential and of membrane potential of CA1 pyramidal cells, which depend on $HCO_3^-$ formation.

FIGS. 5A, 5B and 5C1 to 5C2 show the effects of intracellular administration of calexcitin associated with postsynaptic depolarization induced intracellular θ in hippocampal pyramidal cells.

FIGS. 7A1 to 7A3, 7B1 to 7B2 and 7C1 to 7C5 demonstrate the effects of carbachol (CCH)-induced θ GABAergic depolarization of hippocampal CA1 pyramidal cells in enabling GABAergic inputs to entrain CA1 pyramidal cells.

FIGS. 8A, 8B, 8C1 to 8C2, 8D1 to 8D2 and 8E show the effects of carbonic anhydrase inhibitors in impairing rat formation of spatial memory in vivo.

FIGS. 9A, 9B1 to 9B2 and 9C1 to 9C2 demonstrate the effects of acetazolamide administration in not affecting retrieval of formed spatial memory.

FIGS. 10A to 10H, 10I1 and 10I2, and 10J to 10O show the effects of CE in transforming BAS-CA1 synapses.

DETAILED DESCRIPTION OF THE PREFERRED EMBODIMENTS

Figures 1, 1A:
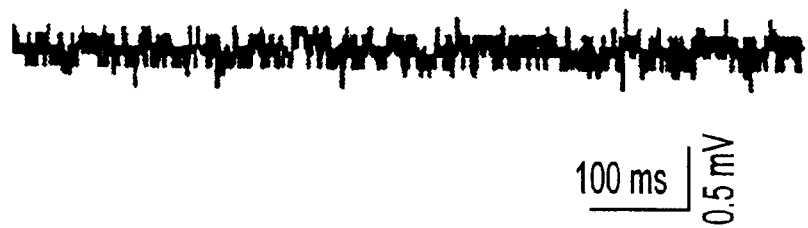

In describing preferred embodiments of the present invention illustrated in the drawings, specific terminology is employed for the sake of clarity. However, the invention is not intended to be limited to the specific terminology so selected. It is to be understood that each specific element includes all technical equivalents, which operate in a similar manner to accomplish a similar purpose. Each reference cited here is incorporated by reference as if each were individually incorporated by reference.

Attentive cognition according to the invention means the ability to pay attention, to learn, and/or to form and acquire memory, including encoding experience into memory and forming associative memory, such as spatial memory, or memories of auditory and/or visual images. Preferably the attentive cognition effects according to the invention are specific. Thus, suppressing attentive cognition preferably does not suppress memory retrieval from stored memories, or cause sensory or locomotor effects.

The invention provides therapeutic methods for modulating attentive cognition by modulating carbonic anhydrase activity in the brain. In particular, the core pathway employed by the inventive methods may be summarized as follows:

Carbonic Anhydrase→Attentive Cognition

More particularly, preferred aspects of the core pathway which are modulated by the methods of the invention are as follows:

Carbonic Anhydrase→bicarbonate formation→Synaptic transformation→Theta rhythm→Attentive Cognition→behavior effects or disease therapy The inventive methods and compositions intervene at various stages in the aspects of the core pathway, and indeed the invention contemplates each of the various combinations of the aspects of the pathway. For example, the invention contemplates methods of increasing or decreasing not only carbonic anhydrase activity, but also (or instead) increasing or decreasing bicarbonate formation, synaptic transformation, and/or theta rhythm establishment to provide some or all of the listed downstream effects, including increasing or decreasing bicarbonate formation, synaptic transformation, and/or theta rhythm establishment, and the ultimate effects including the presence of attentive cognition, and resulting behavioral effects and therapies for disease.

By increasing $GABA_A$ receptor-channel $HCO_3^-$ current relative to $Cl^-$ current, GABA induced depolarization is promoted. This mechanism is sensitive to carbonic anhydrase inhibitors. θ activity is dependent on GABAergic postsynaptic depolarization and a shift of the reversal potential from $Cl^-$ towards $HCO_3^-$. The cholinergic θ activity involves a switch of GABAergic postsynaptic responses from hyperpolarizing predominantly $Cl^-$ to a depolarizing $HCO_3^-$ conductance. This reversed polarity can effectively and immediately entrain pyramidal cells into a θ rhythm.

In vitro, the θ activity was shown to be abolished by $GABA_A$ receptor antagonists and carbonic anhydrase inhibitors, but largely unaffected by blocking cholinergic receptors. Acetazolamide was used to inhibit carbonic anhydrase, an enzyme that increases $HCO_3^-$ formation and regulates $HCO_3^-$ ionic gradient. Carbonic anhydrase is present in hippocampal pyramidal cells. In vivo, carbonic anhydrase inhibition also impaired spatial learning in a watermaze, but did not affect other sensor/locomotor behaviors.

Thus, $HCO_3^-$-mediated signaling, as regulated by carbonic anhydrase through reversed polarity of GABAergic postsynaptic responses, is implicated in both θ activity and memory consolidation in rat spatial maze learning. Carbonic anhydrase activity appears to be an essential requirement in the molecular signaling pathways of GABAergic synapses. The multiple and related effects of carbonic anhydrase in cognition, and the ability to control them via inhibition of the enzyme, are surprising results, and of great significance in designing therapeutic targets.

According to the invention, experiments show that reversed $HCO_3^-$-dependent GABAergic postsynaptic responses and their effectiveness in entraining θ activity of pyramidal cells play a central role in memory retention. Carbonic anhydrase is very efficient and may act as a functional switch to turn on and off θ activity, thereby controlling memory retention. acetazolamide-regulated $HCO_3^-$ gradients appear important for acquisition of memory rather than retrieval from formed memory. Such compounds have clinical value when temporarily suppressed memory is beneficial (e.g. surgery or post-traumatic-stress-disorder).

An aspect of the invention relates to a method of treatment using acetazolamide as a memory suppressor to treat post-traumatic syndrome. The dosage used in the memory experiments provides concentrations of 1–10 micromolar, and in rats corresponds to about 15 mg/Kg. This corresponds to about 1 g for a 70 kg human for a single dosage. Acetazolamide is currently available in dosage forms including 500 mg capsules and injectables; and 250-mg capsules or tablets. Thus, the effectiveness of the inventive method is readily predictable from the animal studies. Moreover, rat spatial learning tests are known to be predictive of attention and learning in humans. Furthermore, it is known that theta rhythms in humans are associated with learning. Thus, the data presented in the examples establish a strong basis for extrapolating to effective therapies for humans.

Example 1 (Miao-Kun Sun, Wei-Qin Zhao, Thomas J. Nelson, and Daniel L. Alkon, "Theta Rhythm of Hippocampal CA1 Neuron Activity: Gating by GABAergic Synaptic Depolarization," Journal of Neurophysiology, vol. 85 No. 1, pp. 269–279 (January 2001)), which is incorporated herein by reference in its entirety, establishes that carbonic anhydrase increases $HCO_3^-$ formation and regulates $HCO_3^-$ gradient formation, to produce GABAergic postsynaptic response and establish a theta rhythm. Memory-related signaling, encoding an experience into lasting memory, and associative memory are linked to the establishment of a theta rhythum. It is thought that an increase in $HCO_3^-$ is needed to mediate attention. These effects seem to control memory acquisition and attention. Acetazolamide inhibits carbonic anhydrase, and reduces $HCO_3^-$ levels. It has newly been discovered that acetazolamide blocks the theta rhythm, and thereby prevents memory acquisition. Intracellular benzolamide, which does not cross the cell membrane absent injection, causes a similar effect when injected. The structural homology of the two compounds suggests a family of analogs with similar effects, as would be known to a person of ordinary skill.

As detailed below, Example 2 relates to the synaptic transformation of GABAergic interneuron cells from producing inhibitory post synaptic signals (IPSPs) to producing excitatory post synaptic signals (EPSPs). It has been determined that calexcitin reduces IPSPs, and has effects on $K^+$-channels, does not blockade a relevant receptor-channel complex, and does cause shifts of reversal potential. Confirming the excitatory effect of calexcitin, anti-CE antibodies enhance IPSPs. More particularly, it has been learned that acetazolamide eliminates calexcitin-induced alterations in IPSPs, probably due to the carbonic anhydrase type II isoform. Acetazolamide at 10 micromolar, for 30 minutes, is sufficient to maintain IPSPs while eliminating transformative effects of calexcitin. This teaches a central role of $HCO_3^-$/carbonic anhydrase activity in the calexcitin-induced synaptic transformation. Calexcitin had no direct effect on carbonic anhydrase activity in a homogenate and so does not act directly on the enzyme.

The effects of carbonic anhydrase activity on inhibiting and/or stimulating theta rhythm and memory formation were not previously known or suggested and are of great significance. For example, as a person of ordinary skill can understand, any carbonic anhydrase inhibitor, including suitable structural analogs and derivatives of acetazolamide and benzolamide, would have a similar memory suppressing effect. In the presence of acetazolamide, Inhibitory Post-Synaptic Potentials (IPSPs) are not converted well to Excitatory Post-Synaptic Potentials (EPSPs). Likewise, potentiators, or upregulators of carbonic anhydrase increase the establishment of a $HCO_3^-$ gradient and theta rhythm, and produce a state of enhanced attention and learning.

According to the invention, one can administer a drug to a patient at a given time to produce a cognitive effect (referred to as attentive cognition), such as learning, learning-related attention, associative learning, and memory acquisition, and memory consolidation (without affecting memory storage and recall) by modulating neuronal carbonic anhydrase activity. The modulation may be inhibition, e.g by acetazolamide and other carbonic anhydrase inhibitors, or it may be excitation, e.g. by compounds that enhance carbonic anhydrase activity and thereby switch GABAergic activity from predominantly hyperpolarizing $Cl^-$ conductance to a depolarizing, primarily $HCO_3^-$ conductance, entraining pyramidal cells into a theta rhythm.

The compounds administered according to the invention can inhibit GABAergic depolarization, and reduction of the theta rhythm, and in turn diminish memory and attention (or the opposite). Without intending to limit the scope of the invention, it is believed that the following mechanism is at play according to the invention. GABA opens $Cl^-$ and $K^+$ channels. Bicarbonate ion $HCO_3^-$ flows through the same channels. When there is relatively more bicarbonate in the cell, it flows out, changing the charge-carrying capacity to bicarbonate from chloride ion. Inhibiting carbonic anhydrase reduces bicarbonate availability relative to chloride ion, thus causing a relative hyperpolarizing effect, and diminishing GABAergic response and synaptic transformation. Activating carbonic anhydrase increases bicarbonate concentration, and/or its availability to flow out through the $Cl^-$ and/or $K^+$ channels, thus having a depolarizing effect, increasing synaptic transformation in the brain and in turn, theta rhythm and attentive cognition.

According to the invention, activators of carbonic anhydrase that are presently known or subsequently discovered may be administered to a patient to increase neuronal carbonic anhydrase activity and to produce the resulting desired effects. This method follows from the method of administering a carbonic anhydrase inhibitor as demonstrated in the examples.

Neuronal carbonic anhydrase activity is meant to encompass activity of carbonic anhydrase in the brain, preferably intraneuronally. Alternatively the invention contemplates modulating extraneuronal carbonic anhydrase. The locus of action may be in various regions of the brain, preferably and as demonstrated in the hippocampus.

The established electrophysiological and biochemical effects of carbonic anhydrase inhibitors on the synaptic transformation of GABAergic synapses support the basic method of inhibiting synaptic transformation in hippocampal cells by administering a carbonic anhydrase inhibitor. The inhibitor eliminates the stimulative effect of calexcitin on cells in hippocampal tissue slices. Further, acetazolamide counteracts the stimulative effects of carbachol, a cholinergic receptor agonist, in vitro.

As to the theta rhythm gating described in more detail in the examples, it is known that theta rhythm is associated with attention, one aspect of associative learning. However, the theta rhythm effects of carbonic anhydrase inhibitors demonstrated here are new and different from what was previously known. Prior to this invention, there was no motivation to combine the electrophysiology and cellular biochemistry relating to carbonic anhydrase with studies of theta rhythm, as they relate to two distinct fields of study.

Thus, principal aspects of the invention include (1) specific cognitive effects, (2) theta rhythm effects, and in particular, (3) the method of enhancing learning by stimulating carbonic anhydrase activity, and (4) inhibiting attention below standard control levels. The fact that carbonic anhydrase is a common link between stimulating excitatory post synaptic potential and stimulating theta rhythm is completely unprecedented and extremely useful in allowing therapies for neurological disorders, including cognitive therapy.

While the studies relate to hippocampal CA1 pyramidal cells, the invention applies to any susceptible target cells in the brain, i.e. GABAergic synaptic circuits.

Interestingly, widespread use of acetazolamide e.g. for glaucoma may be causing memory blockage as an unidentified side effect. The new results suggest screening for those side effects and perhaps counteracting them with cognitive enhancers, or precise dosage and timing regimes that minimize the effects.

EXAMPLES

Example 1

Information processing and memory consolidation during exploratory behavior require synchronized activity known as hippocampal theta ($\theta$) rhythm. Theta ($\theta$) activity depends on cholinergic inputs from the medial septum/vertical limb of the diagonal band nucleus (MS/DBv) and $\theta$ discharges of GABAergic interneurons, and can be induced with cholinergic receptor agonists. However, it was not clear how the increased excitation of pyramidal cells could occur with increased discharges of GABAergic interneurons during $\theta$ waves. The following experiments show that the characteristic $\theta$ activity in adult rat hippocampal CA1 pyramidal cells is associated with GABAergic postsynaptic depolarization and a shift of the reversal potential from $Cl^-$ toward $HCO_3^-$ (whose ionic gradient is regulated by carbonic anhydrase). The $\theta$ activity was abolished by $GABA_A$ receptor antagonists and carbonic anhydrase inhibitors, but largely unaffected by blocking glutamate receptors. Carbonic anhydrase inhibition also impaired spatial learning in a watermaze without affecting other sensory/locomotor behaviors. Thus, $HCO_3^-$-mediated signaling, as regulated by carbonic anhydrase, through reversed polarity of GABAergic postsynaptic responses is implicated in both θ and memory consolidation in rat spatial maze learning. These experiments suggest that this mechanism may be important for the phase forward shift of the place cell discharges for each θ cycle during the animal's traversal of the place field for that cell.

Introduction

Synchronization of neural activity within mammalian brain structures, as occurs during hippocampal θ rhythm (Skaggs W E, and McNaughton B L., Replay of neuronal firing sequences in rat hippocampus during sleep following spatial memory., Science 271: 1870–1873, 1996; Huerta, P. T. and Lisman, J. E., Heightened synaptic plasticity of hippocampal CA1 neurons during a cholinergically induced rhythmic state, Nature 364: 723–725, 1993; O'Keefe, J. and Recce, M. L., Phase relationship between hippocampal place units and the EEG theta rhythm, Hippocampus 3: 317–330, 1993; Shen, J., Barnes, C. A., McNaughton, B. L. Skaggs, W. E., and Weaver, K. L., The effects of aging on experience-dependent plasticity of hippocampal place cells, J. Neurosci. 17: 6769–6782, 1997), contributes to diverse forms of information coding (Draguhn, A., Traub, R. D., Schmitz, D., and Jefferys, J. G., Electrical coupling underlies high-frequency oscillations in the hippocampus in vitro, Nature 394: 189–192, 1998; Usher, M. and Donnelly, N., Visual synchrony affects binding and segmentation in perception, Nature 394: 179–182, 1998; Rodriguez, E., George, N., Lachaux, J. P., Martinerie, J., Renault, B., and Varela, F. J., Perception's shadow: long-distance synchronization of human brain activity, Nature 397: 430–433, 1999). The θ frequency field oscillation, a major feature of the hippocampal electroencephalogram (EEG), for example, occurs during two specific behaviors, exploration and rapid-eye-movement (REM) sleep, and reflects synchronized synaptic potentials that entrain the discharge of neurons at frequencies between 4 and 12 Hz. The rhythm is believed by many to gate or facilitate memory information processing in the hippocampus, particularly during persistent information storage. Thus, as an animal explores its environment, MS/DBv cholinergic inputs, which innervate the whole hippocampal formation (Dutar, P., Bassant, M. -H., Senut, M. -C., and Lamour, Y, The septohippocampal pathway: structure and function of a central cholinergic system, Physiol. Rev. 75: 393–427, 1995; Vertes, R. P. and Kocsis, B., Brainstem-diencephalo-septo-hippocampal systems controlling the theta rhythm of the hippocampus, Neuroscience 81: 893–926, 1997), activate hippocampal θ rhythm (Vertes and Kocsis 1997). Briefly increased θ power has been reported during a word recognition memory task in humans, with a delay of about 125 ms after the visual presentation of a word (Burgess, A. P. and Gruzelier, J. H., Short duration synchronization of human theta rhythm during recognition memory, NeuroReport 8: 1039–1042, 1997). Recording neuromagnetic signals during a working memory task in humans reveals stimulus-locked hippocampal θ (Tesche, C. D. and Karhu J., Theta Oscillations Index Human Hippocampal Activation During a Working Memory Task, Proc. Natl. Acad. Sci. USA 97:919–924, 2000). Evidence has also been provided that disruption of the θ activity by lesions of cholinergic inputs to the hippocampus blocks spatial memory (Winson, J., Loss of hippocampal theta rhythm results in spatial memory deficit in the rat, Science 201: 160–163, 1978). The synaptic bases of the θ rhythm have been extensively studied, but many important questions related to the underlying mechanism(s) for the θ activity remain to be answered. For instance, while the cholinergic θ activity recorded in place pyramidal cells is known to depend on θ rhythmic activity from GABAergic interneurons, pyramidal cells are excited when the animals travel into the field of the place cell, i.e. when GABAergic interneurons are most active (Soltesz, I. and Deschenes, M., Low- and high-frequency membrane potential oscillations during theta activity in CA1 and CA3 pyramidal neurons of the rat hippocampus under ketamine-xylazine anesthesia, J. Neurophysiol. 70: 97–116, 1993; Ylinen, A., Soltesz, I., Bragin, A., Penttonen, M., Sik, A., and Buzsaki, G., Intracellular correlates of hippocampal theta rhythm in identified pyramidal cells, granule cells, and basket cells, Hippocampus 5: 78–90, 1995; Cscsvari, J., Hirase, H., Czurkd, A., Mamiya, A., and Buzsaki, G., Oscillatory coupling of pyramidal cells and interneurons in the behaving rat, J. Neurosci. 19: 274–287, 1999). Furthermore, the firing period of the place cell during the exploration traversal shifts forward during each θ wave and becomes more in phase with interneuron discharge.

Here, it is shown that cholinergic θ activity in hippocampal CA1 pyramidal cells involves a switch of GABAergic postsynaptic responses from a predominantly hyperpolarizing $Cl^-$ to a depolarizing, predominantly $HCO_3^-$ conductance. GABAergic activity through the reversed polarity can effectively and immediately entrain the pyramidal cells into a θ rhythm. Reducing $HCO_3^-$ formation by inhibition of carbonic anhydrase blocks θ rhythm induction in vitro and impairs rat watermaze performance in vivo. Switching between these operational states of the synapses may thereby provide a powerful way to selectively direct signal processing through the network.

Methods

Chemicals. Agents were either injected into the recorded cells through the recording electrodes: benzolamide (gift from T. H. Maren, University of Florida, Gainesville; 0.1 mM; 0.5 nA, 500 ms at 50% on cycles for 10 min) and calexcitin (260 ng/$\mu$l of cloned calexcitin in 1 M K acetate, pH 7.4; −2.0 nA, 700 ms at 33% on cycles for 15 min), or through the perfusion medium: kynurenic acid (Sigma), bicuculline methiodide (BIC; Sigma); carbachol (CCH; Sigma), acetazolamide (ACET; Sigma), and atropine sulfate (Sigma).

Hippocampal slice electrophysiology. CA1 field potentials were recorded with glass microelectrodes filled with an artificial cerebrospinal fluid solution (ACSF; see below). Male Sprague-Dawley rats (150–200 mg) were decapitated, and the brains were removed and cooled rapidly in an ACSF solution (~4° C.), bubbled continuously with 95% $O_2$-5% $CO_2$. Hippocampi were sliced (400 $\mu$M), placed in oxygenated ACSF (in mM: 124 NaCl, 3 KCl; 1.3 $MgSO_4$; 2.4 $CaCl_2$; 26 $NaHCO_3$; 1.25 $NaH_2PO_4$; and 10 glucose), and perfused (2 ml/min) with the oxygenated ACSF in an interface chamber at 30–31 ° C. Whole slices were used unless otherwise indicated. CA1 pyramidal cells were recorded intracellularly (Sun, M. -K., Nelson, T. J., Xu, H., and Alkon, D. L. Calexcitin transformation of GABAergic synapses: from excitation filter to amplifier. Proc. Natl. Acad. Sci. USA 96: 7023–7028, 1999, for cell labeling) with sharp electrodes (3M KAc; tip resistance: 60–120 M; to prevent "run-down" of GABAergic responses in whole-cell recordings due to wash out of intracellular factors). Stable GABAergic inhibitory postsynaptic response (IPSP) could thus be evoked for several hours without noticeable change in amplitudes. Signals were amplified with AxoClamp-2B amplifier, digitized, stored, and analyzed using DigiData 1200 with P-Clamp6 software (Axon Instruments). Frequency and amplitude values of oscillation were taken from an average of five consecutive traces, all triggered at the same level of the same phase. Capacitance was optimally adjusted during discontinuous current-clamp mode before and after cell penetration to neutralize capacitance and reduce overshoot/undershoot errors. Discontinuous single-electrode voltage-clamp mode was used for voltage-clamping, employing a sampling rate of 3.0–5.0 kHz (30% duty cycle). Gain was usually set at 6–8 nA·mV$^{-1}$, slightly below the maximum value without causing overshoot or instability in the step response to a repetitive 10 mV step command. Bipolar stimulating electrodes (Teflon-insulated PtIr wire with 25 μm in diameter) were placed in s. pyramidale, within 200 μm, from the recording electrode, for stimulation of interneurons (50 μA, 50 μA) in the pyramidale layer. In some cases, the position of the stimulating electrodes was slightly varied within the CA1 cell layer to obtain monophasic postsynaptic responses. Test stimuli were applied at 1 per minute (0.017 Hz). In some experiments, an additional stimulating electrode was placed in the stratum radiatum to stimulate the Schaffer collateral pathway (Sch). Experiments in which >20% variations in the evoked IPSP magnitudes occurred during the 10-min control period were discarded.

Spatial maze tasks. Effects of reducing $HCO_3^-$ formation in vivo on spatial memory were evaluated in rats with Morris watermaze task (Meiri, N., Sun, M. -K., Segal, Z., and Alkon, D. L. Memory and long-term potentiation (LTP) dissociated: normal spatial memory despite CA1 LTP elimination with Kv1.4 antisense. Proc. Natl. Acad. Sci. USA 95: 15037–15042, 1998). Male adult Wistar rats were housed in a temperature-controlled (20–24° C.) room for one week, allowed free access to food and water, and kept on a 12 h light/dark cycle. On the first day of experiments, all rats were randomly assigned to different groups (10 each) and swam for 2 min in a 1.5 m (diameter)×0.6 m (depth) pool (22±1° C.). On the following day, rats were trained in a 4 trial/day task for 4 consecutive days. Each training trial lasted for up to 2 min, during which rats learned to escape from water by finding a hidden platform placed in a fixed location and submerged about 1 cm below the water surface. A quadrant test was performed after removing the platform, 24 h after the last training trial. The route of rats' swimming across the pool was recorded. The number of grid-crossings on record paper in each quadrant was counted and used as arbitrary swimming distance units. A single dose of ACET (5 mg/0.5 ml saline/day, freshly prepared) was injected (intraperitoneal), about 65–70 min prior to the first trial or quadrant test. The control rats received the same volume (intraperitoneal) of saline.

Statistical analysis was performed using the Student's t-test for paired or unpaired data or ANOVA whenever appropriate. The values are expressed as means±SE of the mean, with n indicating number of the cells or rats. All animals used in these experiments were treated under National Institutes of Health guidelines for the welfare of laboratory animals.

Results

Figures 1, 1A, 2:
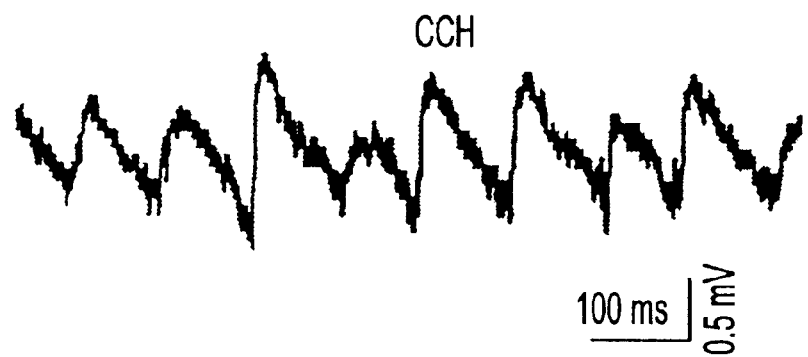
Figures 1, 1A, 2, 3:
Figures 1, 1B:
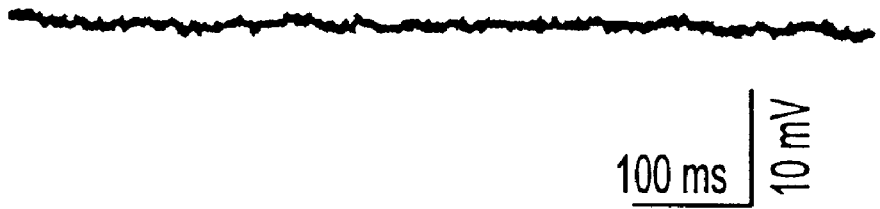
Figures 1, 1B, 2:
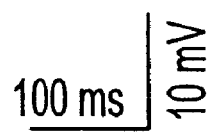
Figures 1, 1B, 2, 3:
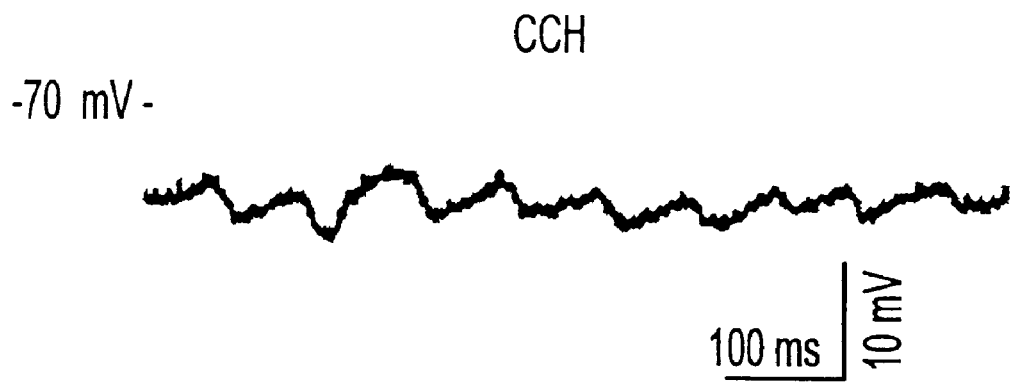
Figures 1, 1B, 2, 3, 4:
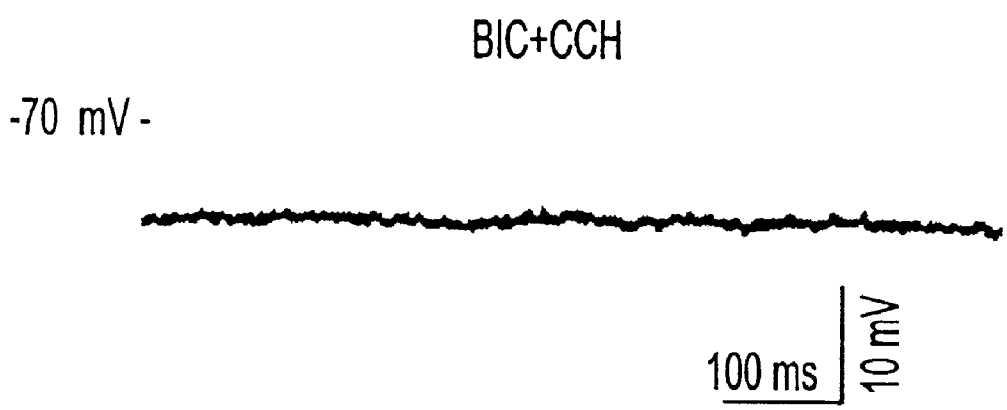
Figures 1, 1C:
Figures 1, 1C, 2:
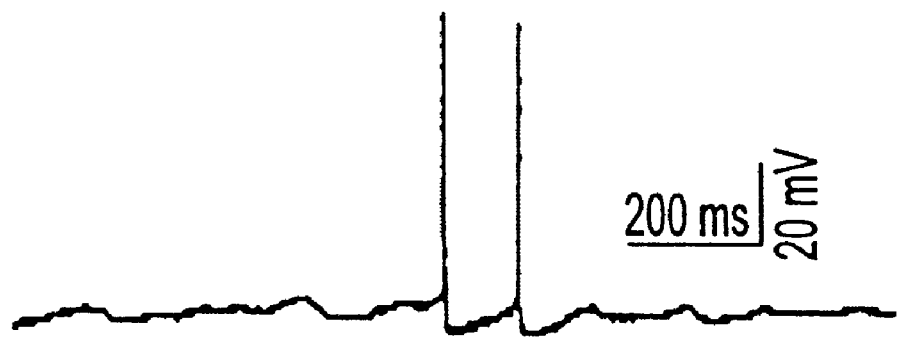
Figures 1, 1C, 2, 3:
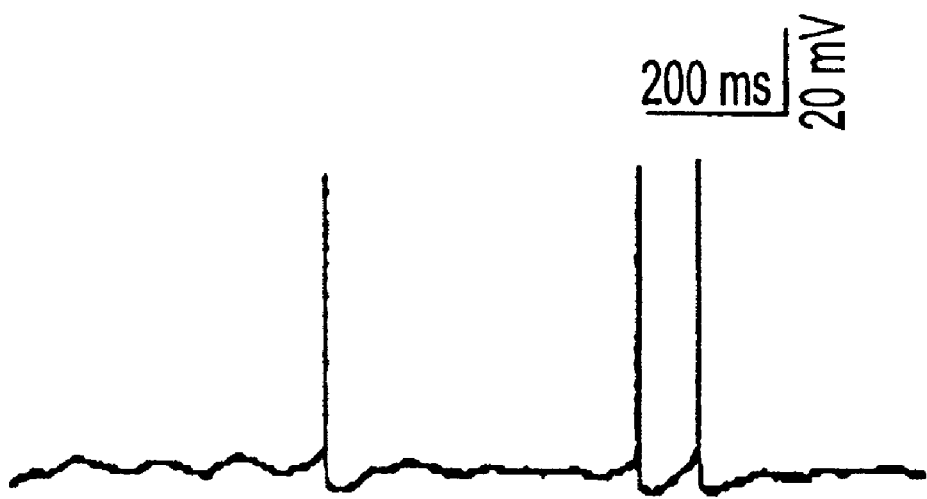
Figures 1, 1C, 2, 3, 4:
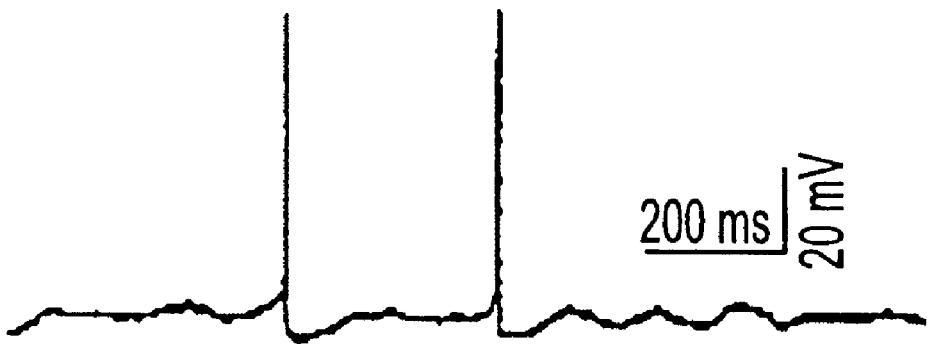

As seen in FIGS. 1A, B and C, carbachol (CCH)-induced θ oscillations of hippocampal CA1 field potential and of membrane potential of CA1 pyramidal cells are shown to be depend on activation of GABAergic inputs. FIGS. 1A-1, -2 and -3 contain examples of recorded field potentials in hippocampal CA1: pre-CCH control (FIG. 1A-1), during CCH (50 μM, 30 min; FIG. 1A-2) and bicuculline application (BIC, 1 μM, 30 min; FIG. 1A-3). FIGS. 1B-1, -2 and -3 show membrane potential traces of recorded CA1 pyramidal cells: pre-CCH (control; FIG. 1B1), during CCH application (50 μM, 30 min; the membrane was slightly depolarized and action potential truncated; FIG. 1B2) and with membrane potential maintained at pre-CCH level by passing negative current; FIG. 1B3), and during application of BIC (1 μM, 30 min; FIG. 1B4). FIG. 1C-1, -2, -3 and -4 show examples of CCH-induced intracellular θ activity in 4 different cells, shown at low amplification and without action potentials truncated.

CCH-induced θ Field Oscillation and Intracellular Theta θ Rhythm Activity

To simulate cholinergic septal activation and diffuse acetylcholine transmission (Descarries, L., Gisiger, V., and Steriade, M., Diffuse transmission by acetylcholine in the CNS, Prog. Neurobiol. 53: 603–625, 1997), CCH (50 μM, 20 min), a cholinergic receptor agonist, was bath applied to hippocampal slices from adult rats. CCH triggered a local θ field potential (FIG. 1A2; peak amplitude: 0.75±0.03 mV, mean±SE, n=12, P<0.05 from background noise; at 7.8±0.8 Hz; n=12), lasting for the post-CCH recording period of ~3 h (Pitler, T. A. and Alger, B. E., Cholinergic excitation of GABAergic interneurons in the rat hippocampal slice, J. Physiol. Lond. 450: 127–142, 1992; Huerta, P. T., and Lisman, J. E., Bidirectional synaptic plasticity induced by a single burst during cholinergic theta oscillation in CA1 in vitro, Neuron 15: 1053–1063, 1995). The θ activity varied in magnitude, indicating summation of different numbers of neurons discharging in each phase.

The θ activity was blocked by bath atropine sulfate (1 μM, n=6; not shown), a muscarinic antagonist, as reported by others (e.g., Huerta and Lisman 1995), and was generated in the CA1. The CCH-induced activity (0.73±0.04 mV, n=7, P<0.05; at 7.7±0.9 Hz; n=7, P<0.05) in CA1 minislices, after dissecting away both CA3 and dentate gyrus, did not differ (P>0.05; unpaired t-test) from that of the whole slices. The θ oscillation frequency did not change (n=8, P>0.05), although the oscillation magnitude was slightly reduced, in the presence of kynurenate, an N-methyl-D-aspartate (NMDA)- and non-NMDA receptor antagonist (Collingridge, G. L. and Lester, R. A, Excitatory amino acid receptors in the vertebrate central nervous system, Pharmacol. Rev. 41: 14–120, 1989). Kynurenate was applied extracellularly at 500 μM (20–30 min), a concentration at which it effectively abolished excitatory postsynaptic responses of CA1 pyramidal cells to stimulation of the Schaffer collateral pathway (Sun et al. 1999) or responses of other brain neurons to L-glutamate (Sun, M. -K., Pharmacology of reticulospinal vasomotor neurons in cardiovascular regulation, Pharmacol. Rev. 48: 465–494, 1996). CCH induced a θ oscillation of membrane potential (7.8±1.1 mV; n=20; P<0.05) in CA1 pyramidal cells (intracellular θ; FIG. 1B2); a response blocked by bath atropine sulfate (1 μM, n=8, P<0.05; not shown). At one-third to one-half of the maximum depolarizing phase, action potentials were triggered. (FIGS. 1A2 and 1B2 to 1B3). During a 5-min observing period, CCH induced an averaged discharge rate of 2.7±0.3 spikes/s, significantly higher (n=20, P<0.05) than their pre-CCH rate (0.0±0.0 spikes/s). These variations were consistent with those of the field θ magnitude recorded. The intracellular θ remained unchanged when the membrane potential of the cells was maintained at their pre-CCH levels.

Figures 1, 2A:
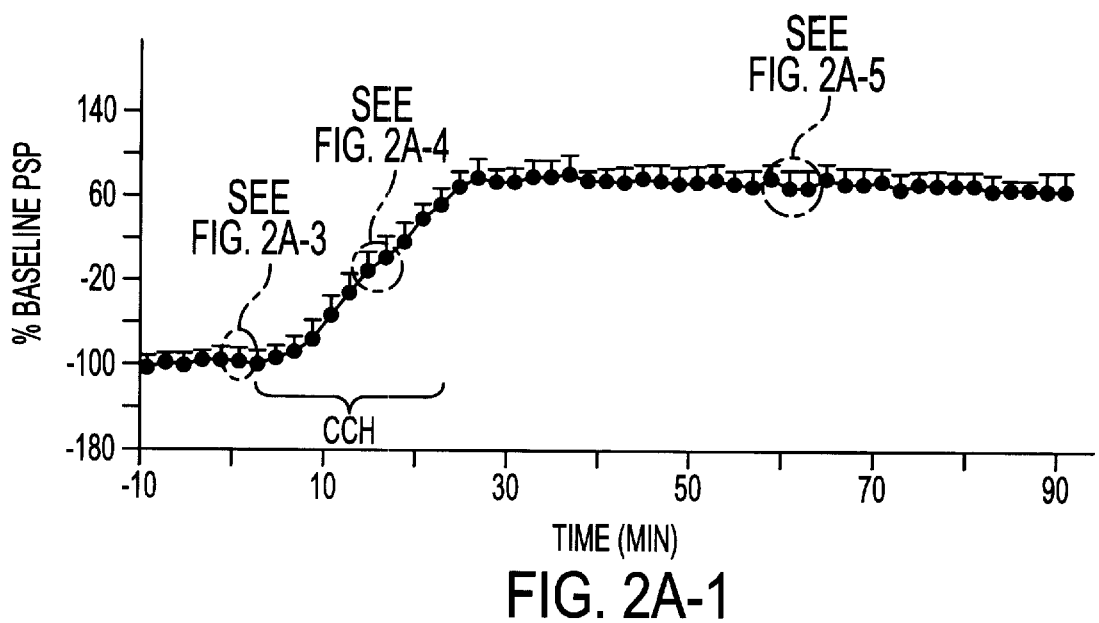
Figures 2, 2A:
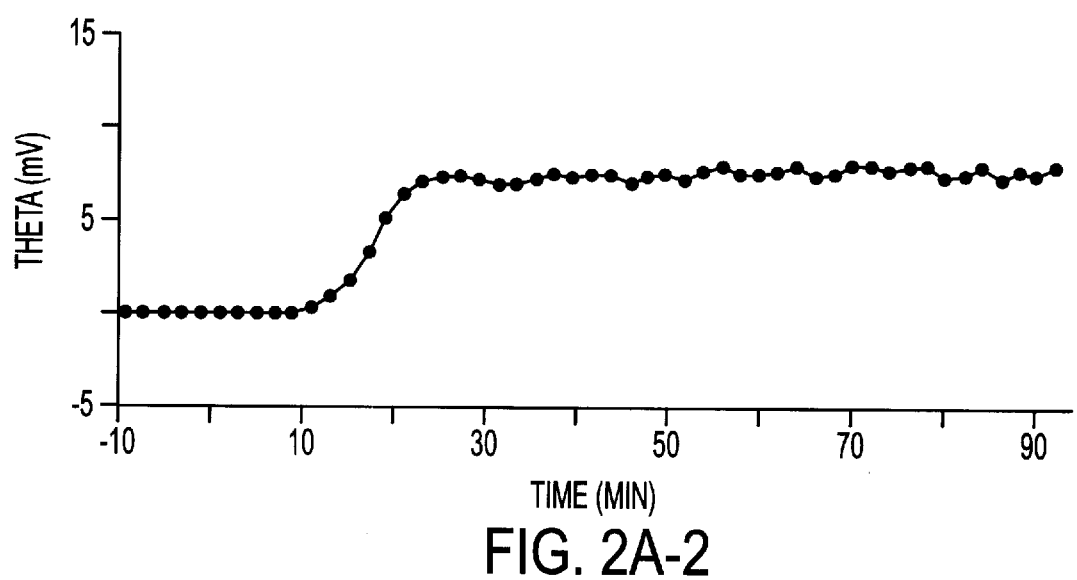
Figures 2, 2A, 3:
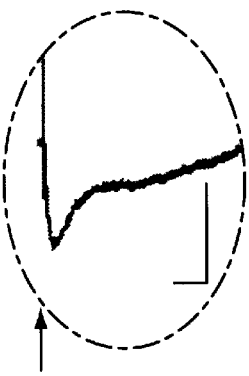
Figures 2, 2A, 3, 4:
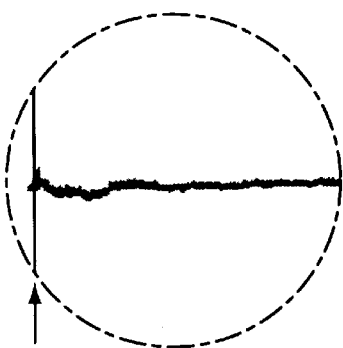
Figures 2, 2A, 3, 4, 5:
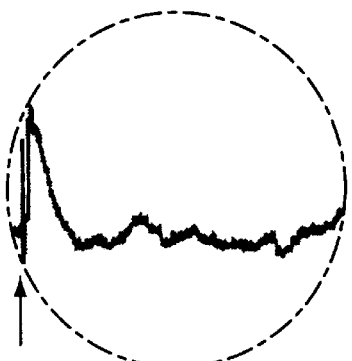
Figure 2B:
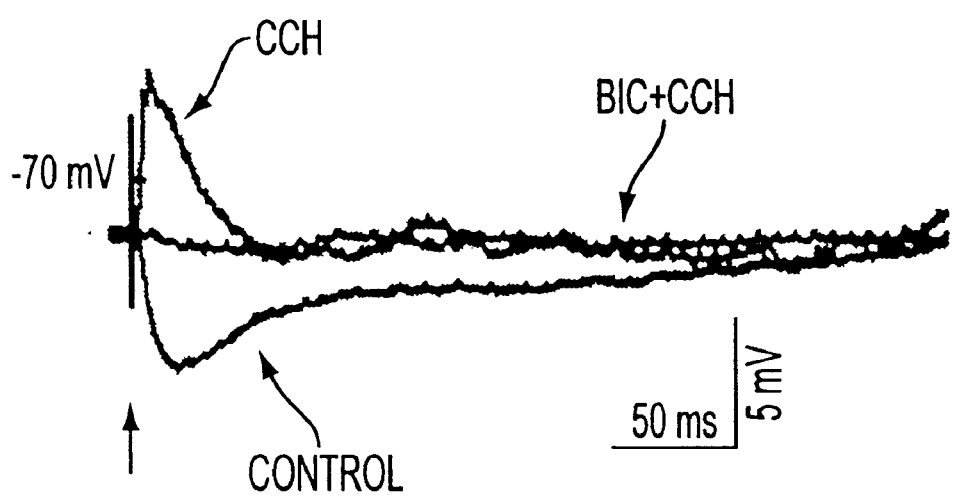
Figure 2C:
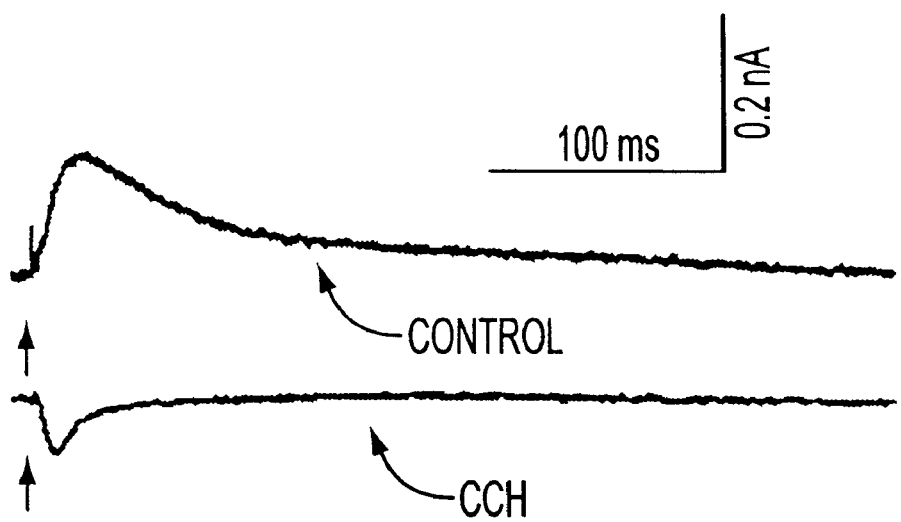

As shown in FIGS. 2A, B and C, carbachol (CCH)-induced θ oscillations of hippocampal CA1 field potential and of membrane potential of CA1 pyramidal cells appear to be associated with GABAergic postsynaptic depolarization. FIGS. 2A1 and 2A2 show that a single pulse stimulation (50 μA, 50 μs) of the GABAergic inputs from interneurons evoked inhibitory postsynaptic potentials (IPSPs), which were gradually reduced and reversed to depolarizing responses during CCH application (50 $\mu$M; CCH), associated with increased amplitude values of $\theta$ activity. The averaged maximum IPSP values of each cell during 10-min stable recording period were defined as 100% baseline PSP. A minus sign was added to indicate its inhibitory nature. For clarity, only every other data point is shown, FIGS. 2A3, 2A4 and 2A5 (calibration bars: 50 ms and 5 mV; dashed horizontal lines indicate potential level of $-70$ mV) showing representing traces at approximate time pointed by broken arrows. FIG. 2B places three of the traces together for comparison. The depolarizing response was blocked by BIC (1 $\mu$M, 30 min; BIC+CCH). Membrane potential was maintained at the pre-CCH level by passing current. FIG. 2C shows that under voltage clamp at $-74$ mV, the evoked GABAergic response was an outward current (Control), which was reversed to inward during CCH application (CCH, 50 $\mu$M, 20 min). Arrowheads indicate the time of the stimulation.

Figures 1, 3A:
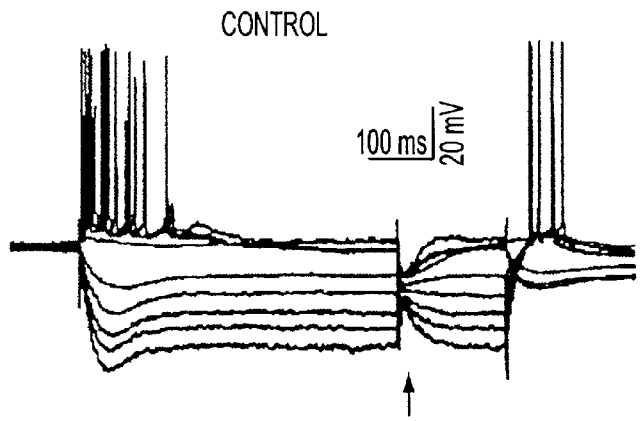
Figures 2, 3A:
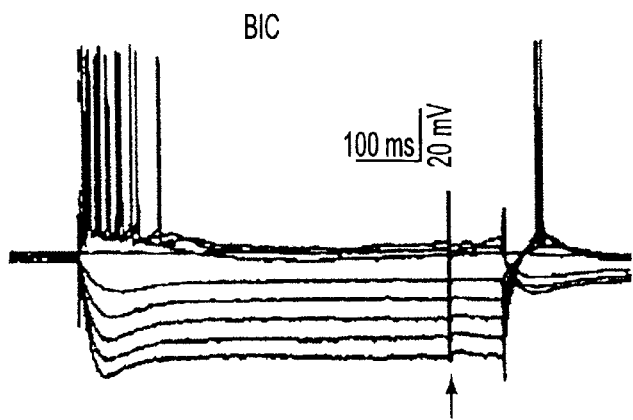
Figures 3, 3A:
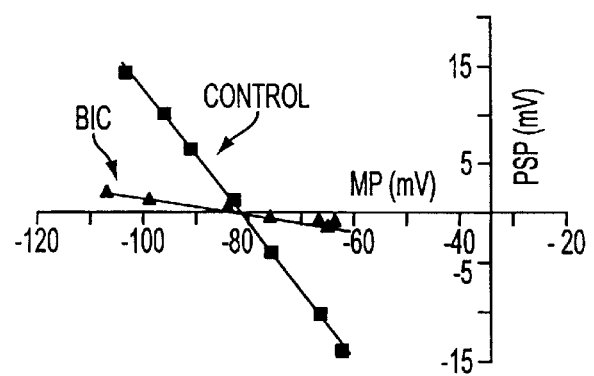
Figures 1, 3B:
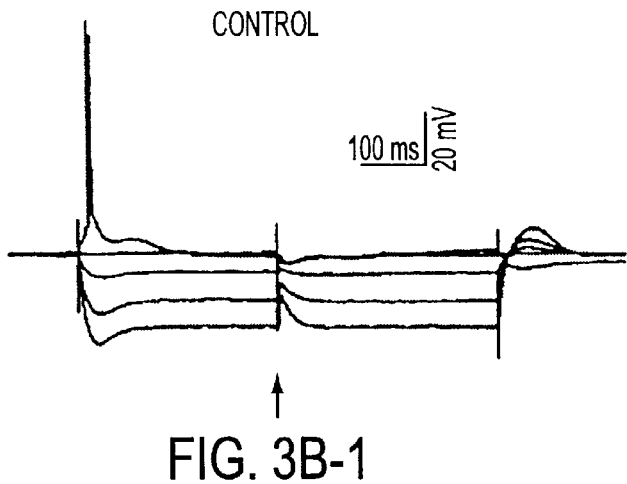
Figures 2, 3B:
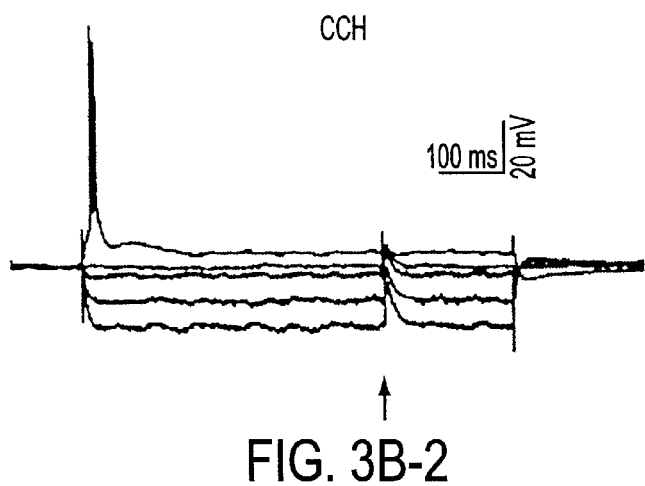
Figures 3, 3B:
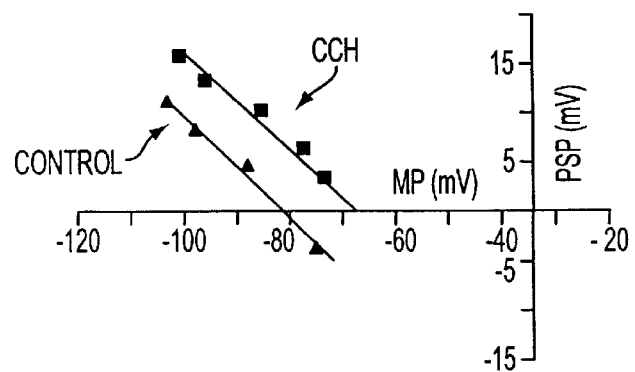
Figures 1, 3C:
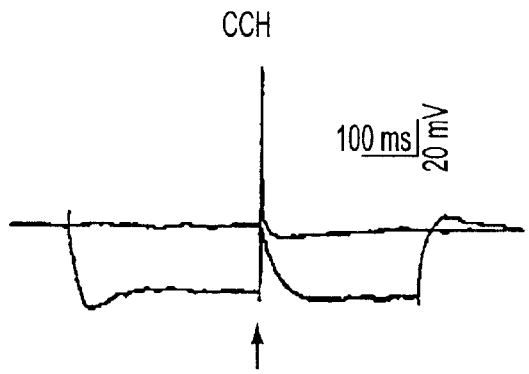
Figures 2, 3C:
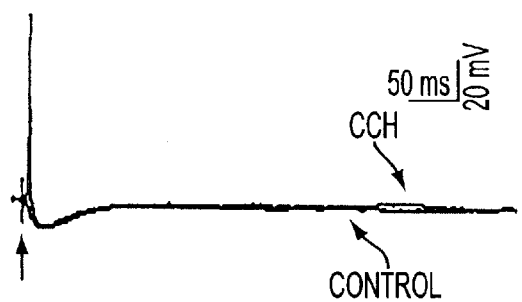
Figures 3, 3C:
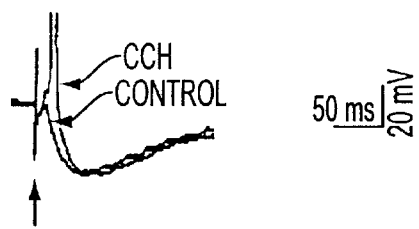

As seen in FIGS. 3A, B and C, carbachol shifts reversal potentials of GABAergic postsynaptic responses in hippocampal CA1 pyramidal cells. Responses of CA1 pyramidal cells to activation of GABAergic inputs at different membrane potentials before (FIG. 3A1) and in the presence of bath 1 $\mu$M BIC, FIG. 3A2). The relationship between the maximum postsynaptic responses and membrane potential can be described with a straight line, determined with the least sum squares criterion and was flattened by BIC without changing the reversal potential. Responses of CA1 pyramidal cells to activation of GABAergic inputs at different membrane potentials before (FIG. 3B1) and during CCH application (50 $\mu$M; FIG. 3B2). Membrane potential was maintained at the pre-CCH level by passing current (FIG. 3B3). Arrowheads indicate the stimulation. FIG. 3C1 shows an example of CCH-induced reversal of GABAergic response that was above threshold for generation of action potentials. The postsynaptic response exhibits a similar relationship between the maximum responses and membrane potential. For clarity, only 2 traces are shown. The same intensity of stimulation of the GABAergic inputs triggered an action potential in the cells post-CCH (CCH) as compared with IPSP pre-CCH (Control; FIG. 3C2). FIG. 3C3 shows the initial segment at x3 magnification with action potential truncated. Arrowheads indicate the time when brief pulse of stimulation was delivered.

Involvement of GABAergic Postsynaptic Depolarization in the CA1 $\theta$ Activities Bath applied BIC (1 $\mu$M) eliminated the $\theta$ field oscillation (by 97.5±4.2%, n=8, P<0.05; FIG. 1A2) and CA1 intracellular $\theta$ activity (by 98.9±3.4%, n=10, P<0.05; FIG. 1B4). When applied before the CCH application, BIC did not produce obvious changes in the field potential (n=6) or membrane potentials of CA1 pyramidal cells (n=8), but prevented CCH effects on the $\theta$ activity induction. At 1 $\mu$M, BIC did not produce any obvious excitation of the CA1 cells. Activation of the $GABA_A$ receptors is thus necessary for CCH to elicit synchronous CA1 field events. Suppressing $GABA_A$ receptor channels alone is insufficient to induce $\theta$.

The GABAergic inputs were activated by microstimulation of s. pyramidale. The evoked inhibitory postsynaptic potentials (IPSPs) in CA1 pyramidal cells depended on the membrane potentials (e.g., FIGS. 3A1 to 3A3, 3B1 to 3B3, and 3C1 to 3C3). Thus, the were always monitored with values compared at their pretest control membrane potentials. The evoked IPSPs (FIGS. 2A1 to 2A5; peak response: $-8.89\pm0.29$ mV, n=89) were not altered by kynurenate (500 $\mu$M, n=6), but abolished by BIC (1 $\mu$M, by 96.8±3.7%; n=8, P<0.05), indicating $GABA_A$ receptor mediation and an absence of contamination of any obvious excitatory component in the evoked IPSPs. Associated with the $\theta$ activity was a gradual reduction in the IPSPs (n=25) and the ultimate production of an 'excitatory' response (FIGS. 2A1 to 2A5 and 2B; from pre-CCH $-9.0\pm1.2$ mV as compared with +5.1±0.4 mV 30 min after the CCH application; n=10, P<0.05). This excitatory response was observed at the pre-CCH membrane potential maintained by intracellular injection of hyperpolarizing current. These voltage changes in the GABAergic responses corresponded to a gradual change of an outward current (0.18±0.03 nA) toward an inward current (0.19±0.05 nA; n=5, P<0.05) under voltage clamp (FIG. 2C). The intracellular $\theta$ activity became evident when the GABAergic responses became depolarizing (FIGS. 2A1 to 2A5). Measured when the $\theta$ activity became evident, the input resistance (79.2±1.6 M$\Omega$) of the cells did not significantly differ (n=10; P>0.05) from their pre-CCH value (80.5±1.4 M$\Omega$). Depressing $GABA_A$ responses alone was insufficient to induce the $\theta$ activity since BIC did not induce the rhythmic activity (see last paragraph). The reversed excitatory response was also sensitive to BIC (FIG. 2B), indicating the involvement of the same type of receptor-channel before and after the CCH administration.

The relationship between the maximum responses of hippocampal CA1 pyramidal cells to stimulation of the GABAergic inputs and membrane potential at which the inputs were activated can be described with a straight line. BIC virtually abolished the GABAergic postsynaptic responses no matter whether the postsynaptic responses were evoked at membrane potentials positive or negative to the reversal potential (FIGS. 3A1 to 3A3). The reversal potential, however, was not changed by BIC (FIG. 3A2; $-81.3\pm2.6$ mV; n=6). This BIC effect contrasts with CCH-induced changes that were associated with a positive-shift of the reversal potential (FIGS. 3B1 to 3B3; from $-79.8\pm3.2$ to $-68.4\pm2.8$ mV; n=10, P<0.05). Thus, the CCH-induced changes in GABAergic responses are fundamentally distinct from a reduced response and could not result from a diminished GABAergic synaptic transmission (suppressed presynaptic release or postsynaptic response). FIGS. 3C1 to 3C3 illustrate an example in which the CCH-induced reversal potential appears to be above the threshold (approximately $-57$ mV) for generation of action potential. Thus single brief pulse of stimulation of the GABAergic inputs elicited action potential during post-CCH period in the cell, in contrast to inhibitory postsynaptic response before the CCH application (FIGS. 3C1 to 3C3).

Figures 1, 4A:
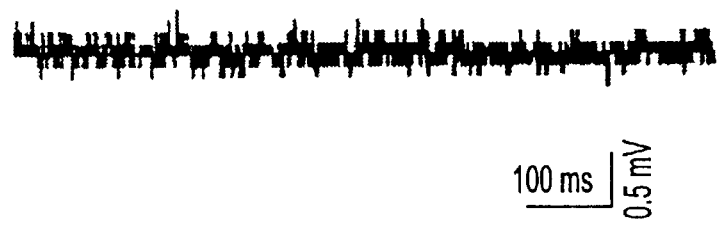
Figures 2, 4A:
Figures 3, 4A:
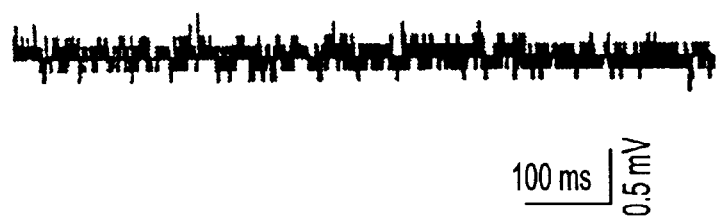
Figures 1, 4B:
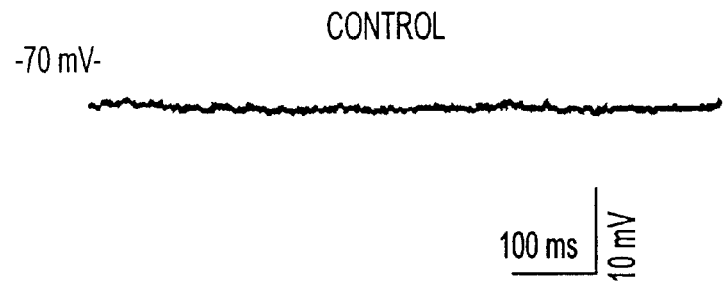
Figures 2, 4B:
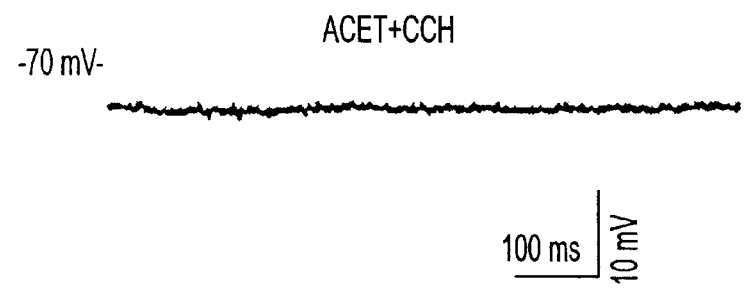
Figures 3, 4B:
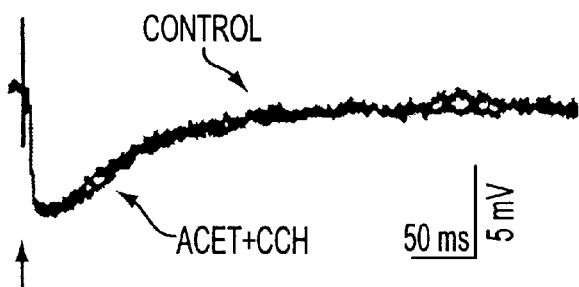

Elimination of CA1 $\theta$ Activities and GABA Depolarization by Carbonic Anhydrase Inhibitors As shown in FIGS. 4A1 to 4A3, and 5B1 to 5B3, carbachol (CCH)-induced $\theta$ oscillations of hippocampal CA1 field potential and of membrane potential of CA1 pyramidal cells depend on $HCO_3^-$ formation. An example of recorded field potentials in hippocampal CA1: pre-CCH control (FIG. 4A1), during CCH (50 $\mu$M, 30 min; FIG. 4A2) and acetazolamide (ACET) application (1 $\mu$M, 30 min; FIG. 4A3). Membrane potential traces of recorded CA1 pyramidal cells: pre-CCH control (4B1), during CCH application (50 $\mu$M, 30 min) in the presence of ACET (1 $\mu$M, 30 min; FIG. 4B2). In the presence of 1 $\mu$M ACET, single pulse stimulation (50 $\mu$A, 50 $\mu$s) of the GABAergic inputs evoked an IPSP (Control), which was not altered by CCH application (50 $\mu$M, 30 min) (FIG. 4B3).

Figure 5A:
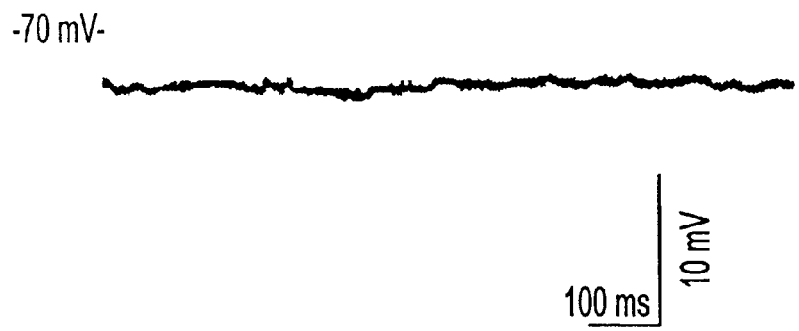
Figure 5B:
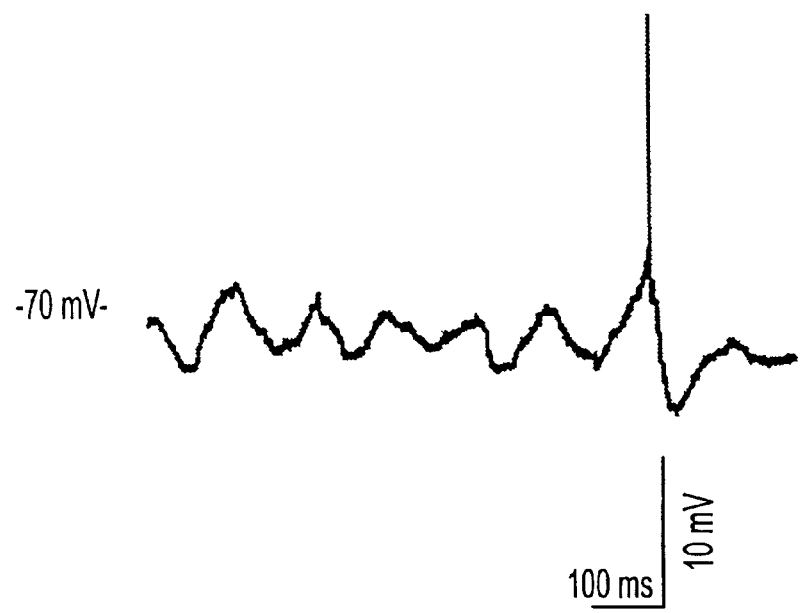
Figures 1, 5C:
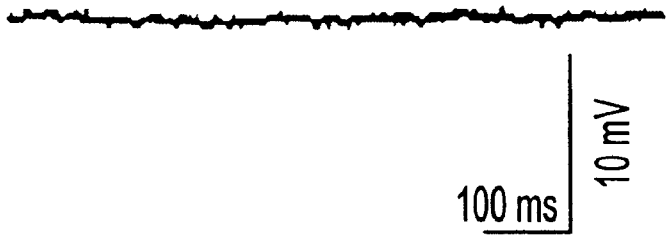
Figures 2, 5C:
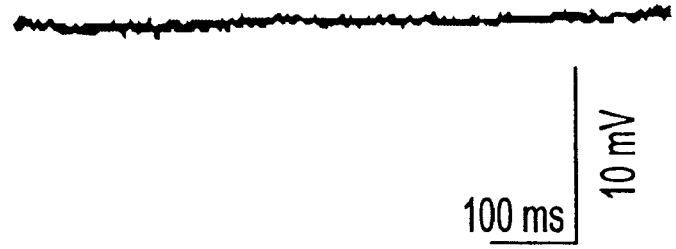

As seen in FIGS. 5A, 5B and 5C1 to 5C2, intracellular administration of calexcitin associated with postsynaptic depolarization induced acetazolamide-sensitive intracellular θ in hippocampal pyramidal cells. Before the application, the membrane potential of the CA1 pyramidal cell did not show θ activity (FIG. 5A). Calexcitin application (associated with a depolarizing current of 0.4–0.6 nA during the off-period to evoke 4–8 spikes/s to load $Ca^{2+}$) into the recorded neuron induced the intracellular (FIG. 5B) θ. In the presence of 1 μM ACET, calexcitin application (associated with a depolarizing current of 0.4–0.6 nA during the OFF-period to evoke 4–8 spikes/s to load $Ca^{2+}$) into the recorded neuron did not induce the intracellular theta rhythm activity θ (FIG. 5C1 and 5C2).

Bath ACET (1 μM, a carbonic anhydrase inhibitor, eliminated the CCH-induced changes in GABAergic postsynaptic responses (FIG. 4B2). The evoked IPSP (−7.7±1.0 mV, n=12, P<0.05) in the presence of ACET and CCH did not differ (n=12, P>0.05) from their control values (−7.8±1.1 mV). Under such conditions, neither θ field oscillation (n=8; FIG. 4A) nor intracellular θ activity (n=10; FIG. 4B3) was induced by CCH. Similarly, intracellular application of benzolamide, a membrane-impermeable carbonic anhydrase inhibitor, prevented the occurrence of CCH-induced reversed GABAergic responses and intracellular θ activity (n=6), indicating an involvement of intracellular carbonic anhydrase. Interestingly, application of calexcitin, a memory-related signal protein (Alkon, D. L., Nelson, T. J., Zhao, W. Q., and Cavallaro, S., Time domains of neuronal $Ca^{2+}$ signaling and associative memory: steps through a calexcitin, ryanodine receptor, $K^+$ channel cascade, Trends Neurosci. 21: 529–537, 1998; Sun et al. 1999), into CA1 pyramidal cells mimicked CCH in inducing the intracellular θ activity (FIG. 5B; n=10), when associated with a depolarizing current to load $Ca^{2+}$. The calexcitin-induced intracellular θ activity was also prevented by bath ACET (1 μM) in six cells tested (FIG. 5C2). These results indicate a critical role of $HCO_3^-$ conductance in an intracellular signaling cascade responsible for the θ rhythm.

Entraining CA1 Pyramidal Cells by GABAergic Inputs

Figure 6A:
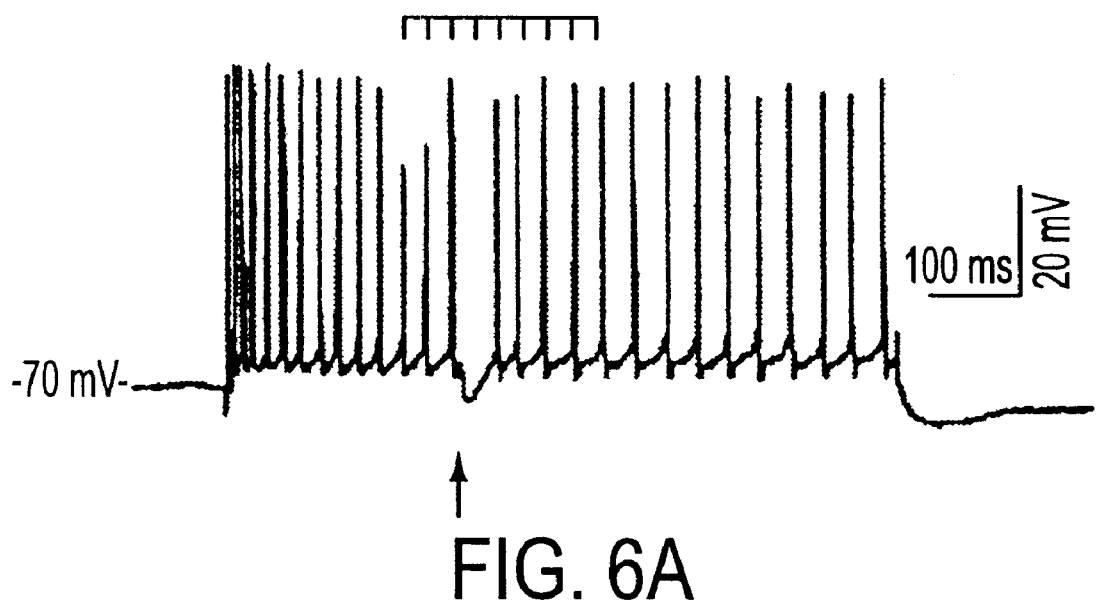
FIGS. 6A, 6B, 6C and 6D demonstrate rebound action potentials of hippocampal CA1 pyramidal cells evoked by GABAergic inhibition, which vary in occurrence and timing.
Figure 6B:
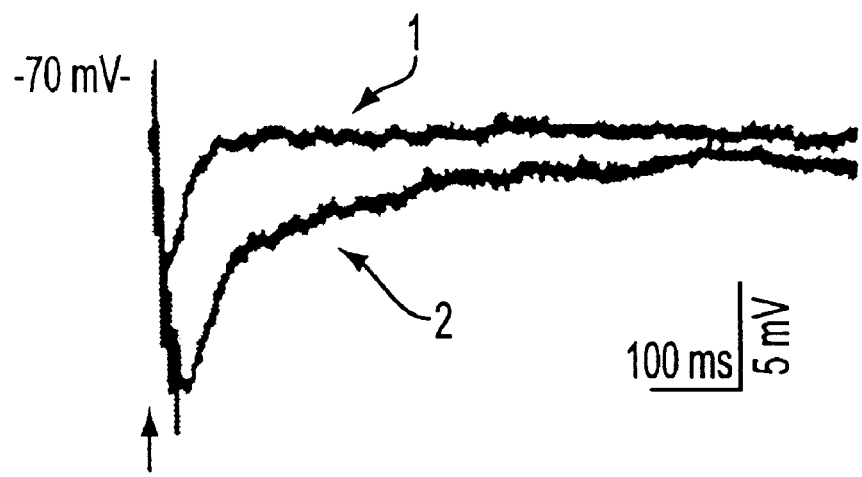
Figure 6C:
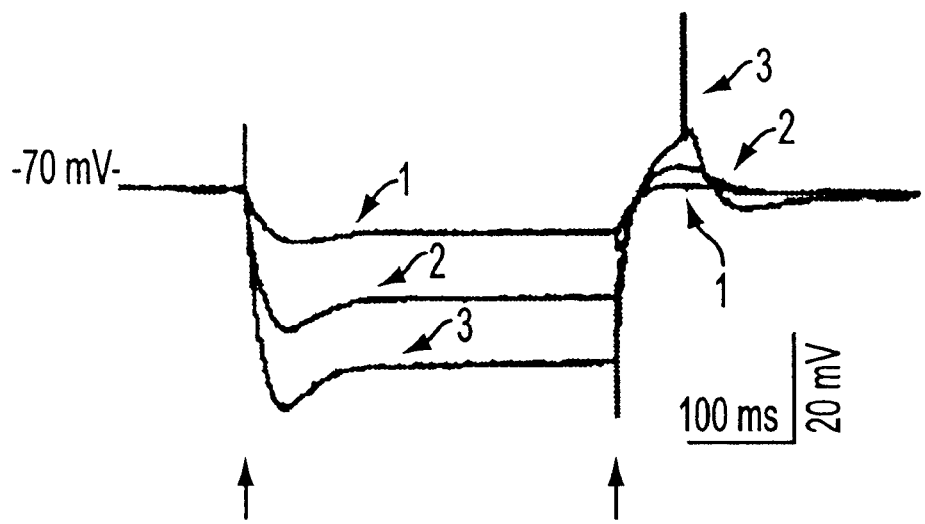
Figure 6D:
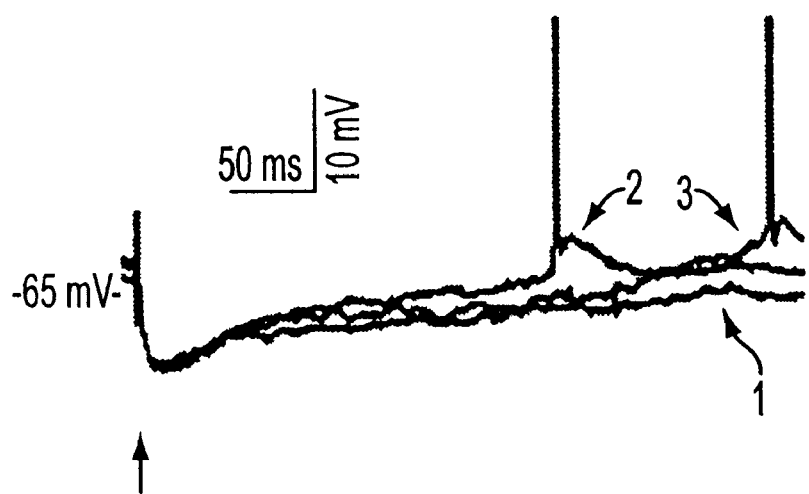

As shown in FIGS. 6A, B, C and D, rebound action potentials of hippocampal CA1 pyramidal cells evoked by GABAergic inhibition vary in occurrence and timing. In slowly adapting cells, an evoked IPSP can delay or reset the subsequent occurrence of spikes when the cells were depolarized (FIG. 6A). The vertical lines above the trace indicate the expected time for an action potential to occur if the cell continued to discharge at the same regular intervals observed immediately before the stimulus was delivered. Arrowhead indicates the stimulation. Rebound depolarization was not evoked at resting membrane potential with single pulse (trace 1) or a train of 4 pulses at 100 Hz (trace 2) stimulation of the GABAergic inputs (FIG. 6B). Rebound action potential at resting membrane potential requires too strong hyperpolarization (FIG. 6C) (≧30 mV; trace 3 with action potential truncated), otherwise no rebound depolarization was evoked (trace 1). When depolarized, rebound action potential can be induced but with low safety and varied timing (with action potential truncated) (FIG. 6D).

Figures 1, 7A:
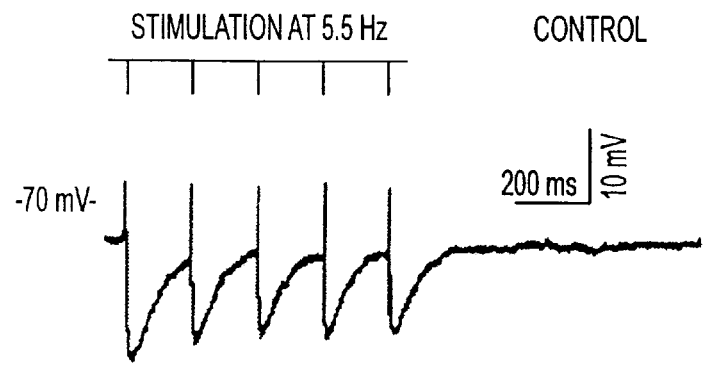
Figures 2, 7A:
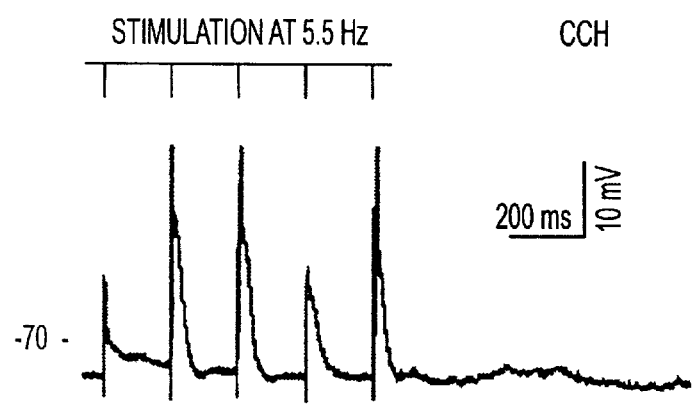
Figures 3, 7A:
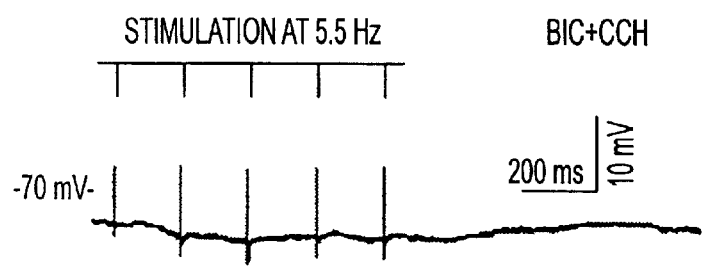
Figures 1, 7B:
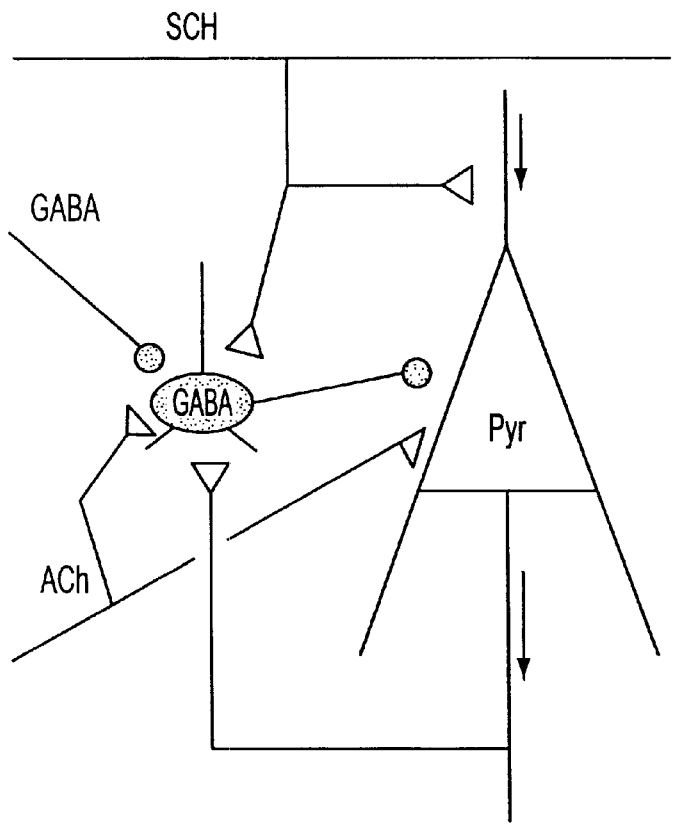
Figures 2, 7B:
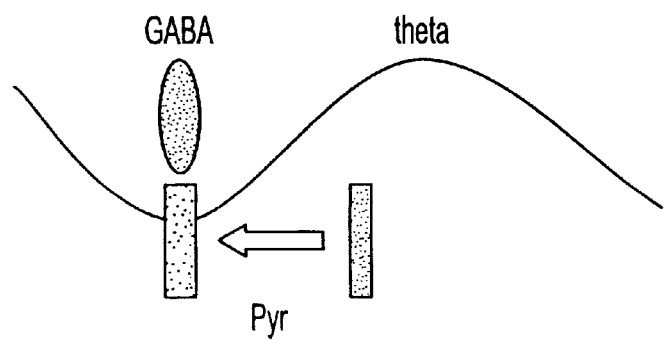
Figures 1, 7C:
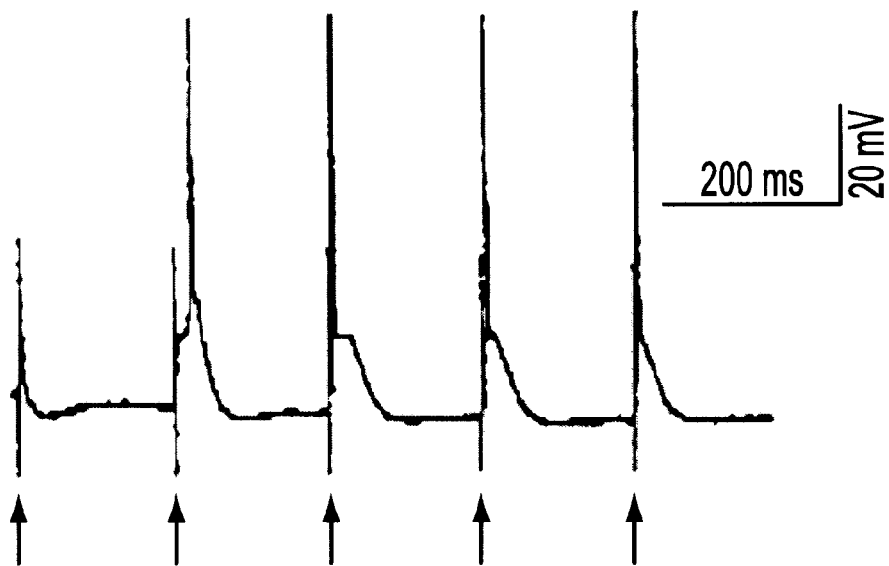
Figures 2, 7C:
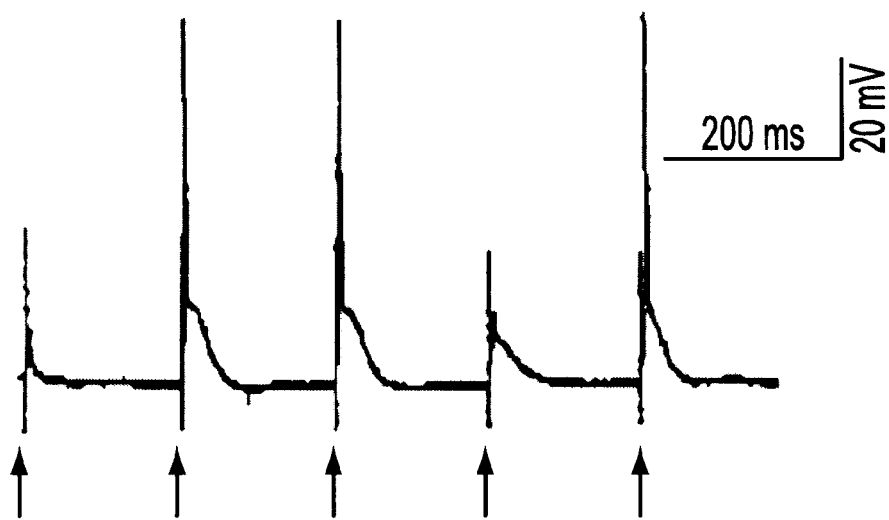
Figures 3, 7C:
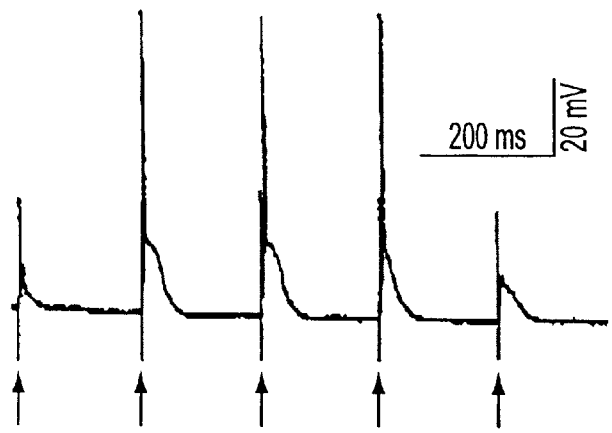
Figures 4, 7C:
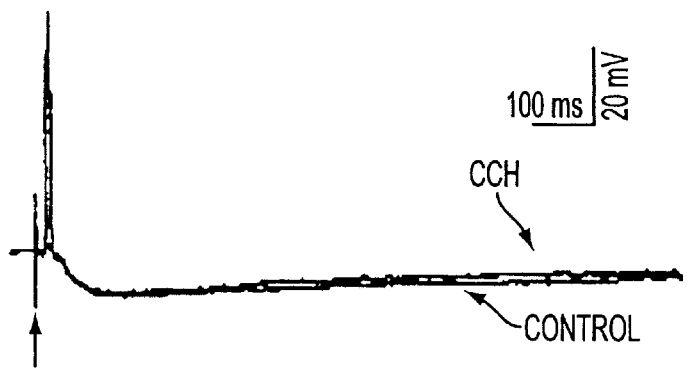
Figures 5, 7C:
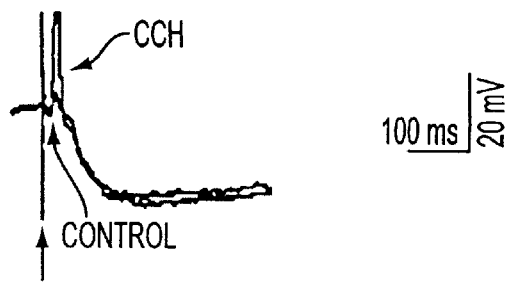

As seen in FIGS. 7A1 to 7A3, 7B1 to 7B2 and 7C1 to 7C5, carbachol (CCH)-induced θ GABAergic depolarization of hippocampal CA1 pyramidal cells enables GABAergic inputs to entrain CA1 pyramidal cells. θ rhythm stimulation evoked IPSPs before CCH application (Control; FIG. 7A1). During CCH application (50 μM, 30 min; FIG. 7A2), the same pattern of stimulation entrained activity of the pyramidal cell. Action potentials were evoked at the 2nd, 3rd, and 5th pulses, with action potentials truncated. The evoked postsynaptic responses were abolished by BIC (1 μM, 30 min; FIG. 7A3). A schematic diagram of the supposed network and discharge relationship between CA1 pyramidal cells and GABAergic interneurons is shown in FIG. 7B1. Cholinergic inputs (synaptic or diffuse transmission) act on pyramidal cells, inducing $HCO_3^-$ accumulation and enhance $HCO_3^-$ conductance through the $GABA_A$ receptor channels. The θ rhythmic activity of GABAergic interneurons can then directly be transmitted to the pyramidal cells, entraining their activity and altering signal processing. FIG. 7B2 models a peak discharge relationship of pyramidal cells (black rectangle) and interneurons (shadow oval) in θ rhythm in behaving and rapid eye movement (REM) sleep (based on O'Keefe and Recce 1993; Shen et al. 1997; Csicsvari et al. 1999). The arrow indicates the discharge shift of a place cell, starting from shadow rectangle, in relation to the θ activity as the animal travels into the place field of the place cell. GABA, GABAergic interneurons; Pyr, CA1 pyramidal cells; SCH, Schaffer collateral pathway. FIGS. 7C1 to 7C3 show examples of traces without truncation, showing that the brief pulse of stimulation at 5.5 Hz elicited action potentials even though the 1st brief pulse of stimulation was insufficient to evoke action potential. FIG. 7C4 illustrates responses to co-stimulation of SCH at below-threshold intensity and GABAergic inputs at pre-CCH (Control) and post-CCH (CCH) periods. FIG. 7C5 shows the initial segment at ×3 amplification with action potential truncated. Arrowheads indicate the time when the brief pulse of stimulation was delivered.

Entraining hippocampal pyramidal cells at θ frequency has been proposed to be a fundamental role of the interneurons (Cobb, S. R., Buhl, E. H., Halasy, K., Paulsen, O., and Somogyi, P., Synchronization of neuronal activity in hippocampus by individual GABAergic interneurons, Nature 378: 75–78, 1995; Paulsen, O. and Moser, E. I., A model of hippocampal memory encoding and retrieval: GABAergic control of synaptic plasticity, Trends Neurosci. 21: 273–278, 1998). The only previously proposed mechanism for how GABAergic interneurons entrain the pyramidal cells is rebound action potential. However, rebound 'depolarization' usually requires resting activity that was provided by constant current injection (Cobb et al. 1995) and hippocampal pyramidal cells normally do not show much spontaneous activity. In some cells (26 out of 149 neurons in which effects of membrane potential changes on the GABAergic postsynaptic responses were examined), discharges lasted for a period of elicited depolarization and an evoked IPSP appeared to be able to delay subsequent spikes (FIG. 6A). The majority of cells (123 out of 149), however, showed a rapid adaptation to depolarization (FIG. 3A1 to 3A3 and 3B1 to 3B3), resulting in a silent but depolarized state. At resting membrane potential, rebound depolarization requires very strong hyperpolarization, which naturally occurring IPSPs are unlikely to provide. No rebound action potential was observed with IPSPs of −8.9±0.3 mV evoked at resting membrane potentials (−73.8±0.9 mV, n=89; FIG. 6B, trace 1). A train of pulses at 100 Hz was also ineffective (FIG. 6B, trace 2), suggesting that temporal summation of the unitary IPSPs is insufficient to evoke rebound depolarization. Furthermore, no significant rebound depolarization (0.19±0.12 mV, n=75, P>0.05) was evoked with intracellular pulses (up to 700 ms) sufficient to evoke −10.8±1.4 mV potential changes (FIG. 6C, trace 1) from their resting membrane potential (−74.8±0.4 mV). In addition, when evoked at depolarized membrane potentials, the occurrence and timing of individual 'rebound' action potentials varied (FIG. 6D). Thus, rebound action potentials, even when they occur, do not represent a precise control mechanism. On the other hand, in the presence of CCH, stimulation of GABAergic inputs elicited instantly phase-locked firing of pyramidal cells (FIGS. 7A2 and 7C1 to 7C3; n=14). The postsynaptic GABAergic response to the first stimulation pulse usually did not reach action potential threshold (FIGS. 7A2 and 7C1 to 7C3). The postsynaptic GABAergic responses were sensitive to BIC, indicating the involvement of the same receptor-channels (FIGS. 7A3). In eight cells, single pulse stimulation of SCH (10–30 $\mu$A, 50 $\mu$s) evoked an excitatory postsynaptic potential of 7.5±1.2 mV, which was about 50% below the threshold. Before the CCH administration, co-stimulation of SCH at the set intensity (50% below the threshold) and GABAergic inputs (50 $\mu$A, 50 $\mu$s) largely abolished the SCH stimulation-induced excitatory potential (by 89.5±4.3%, n=8, P<0.05; FIG. 7C4). The single-pulse SCH stimulation-evoked excitatory postsynaptic potential was not altered (P>0.05) by CCH (not shown). Action potentials, however, were evoked by co-stimulation of Sch at below-threshold intensity together with reversed GABAergic inputs in all cases (n=8, P<0.05; FIG. 7C-4). Thus, reversed synaptic responses reshapes the GABAergic inhibitory function into amplification (Sun et al. 1999) and reconfigures the operations of hippocampal networks into patterns of activity associated with GABAergic inputs (FIG. 7B1 and 7B2).

Spatial Memory Deficits by ACET Administration in vivo

Figure 8A:
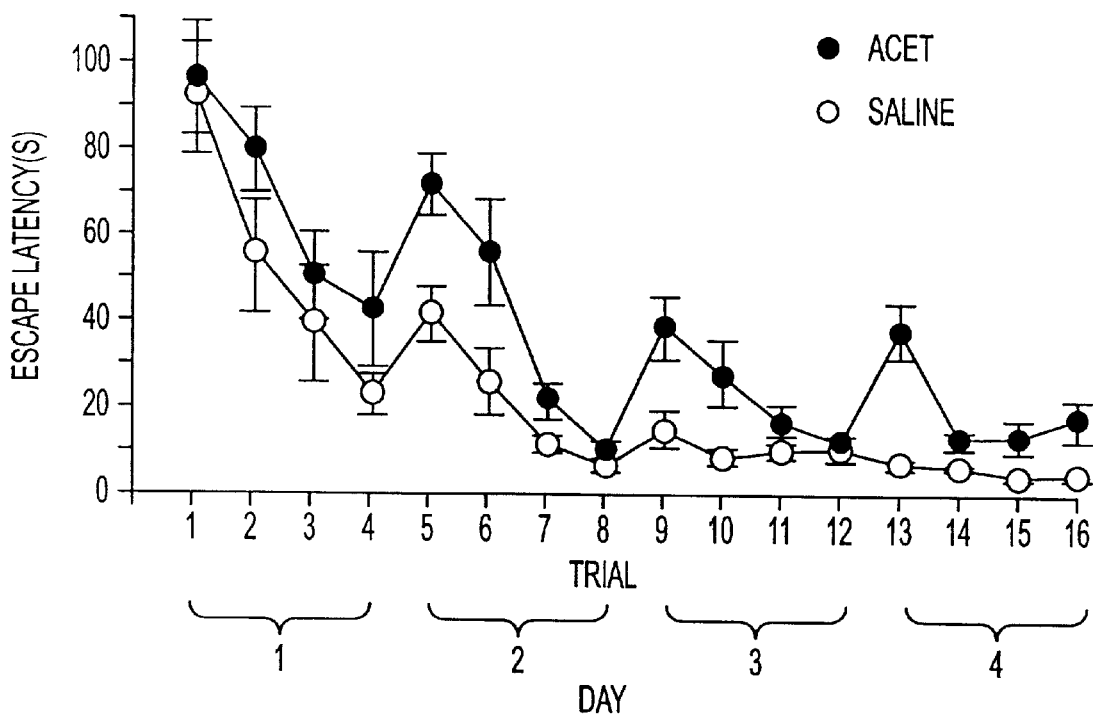
Figure 8B:
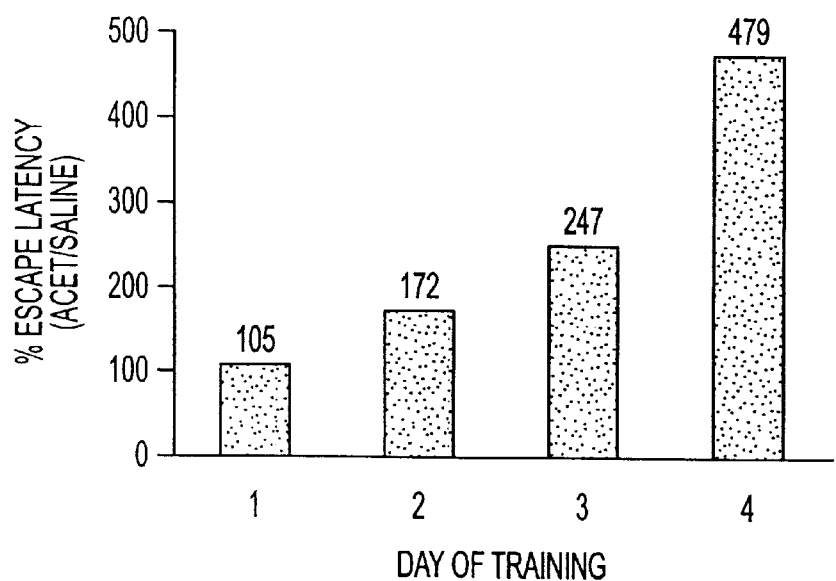
Figures 1, 8C:
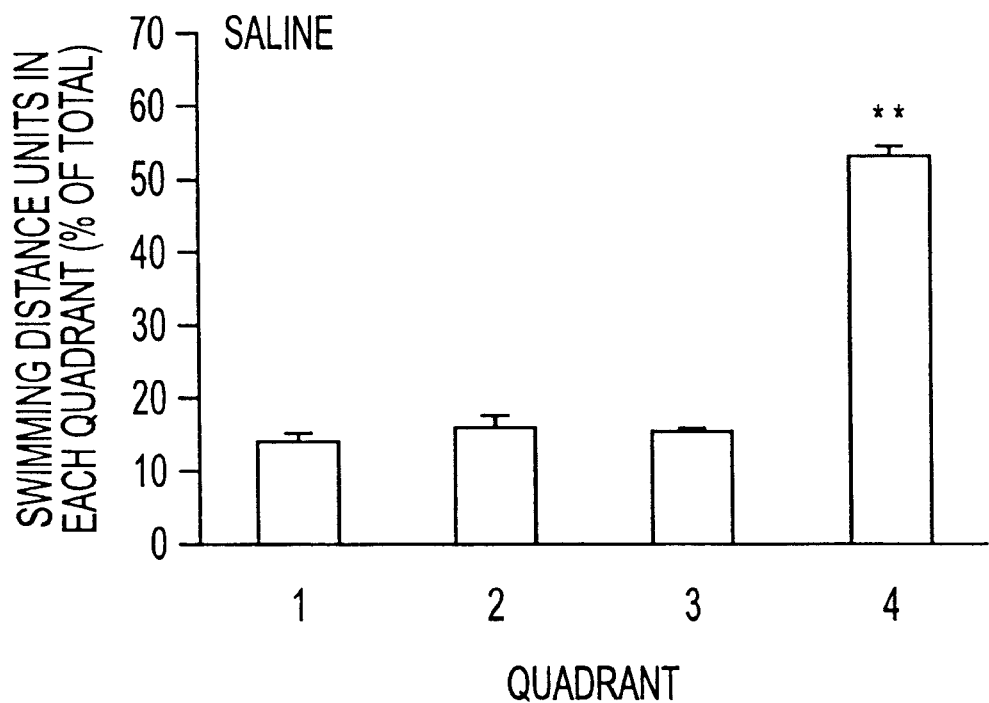
Figures 2, 8C:
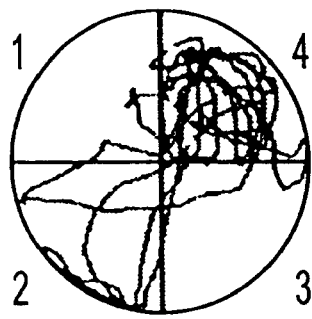
Figures 1, 8D:
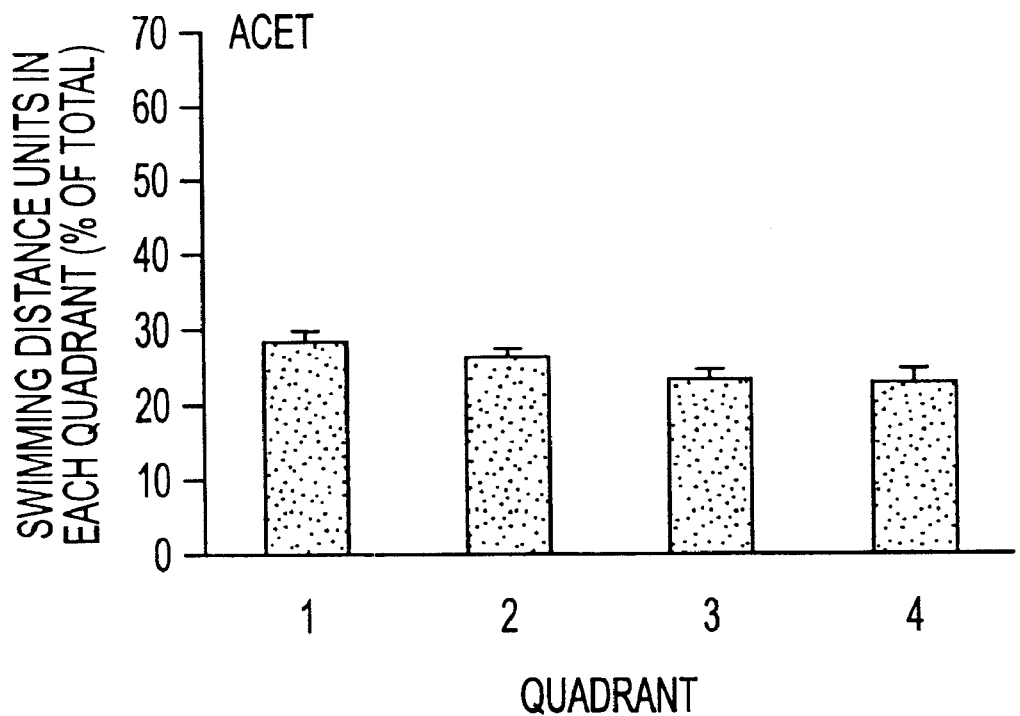
Figures 2, 8D:
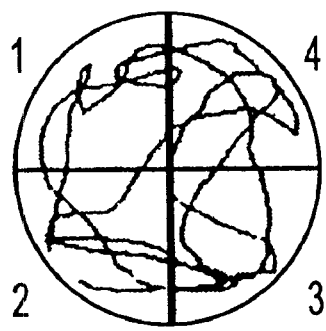
Figure 8E:
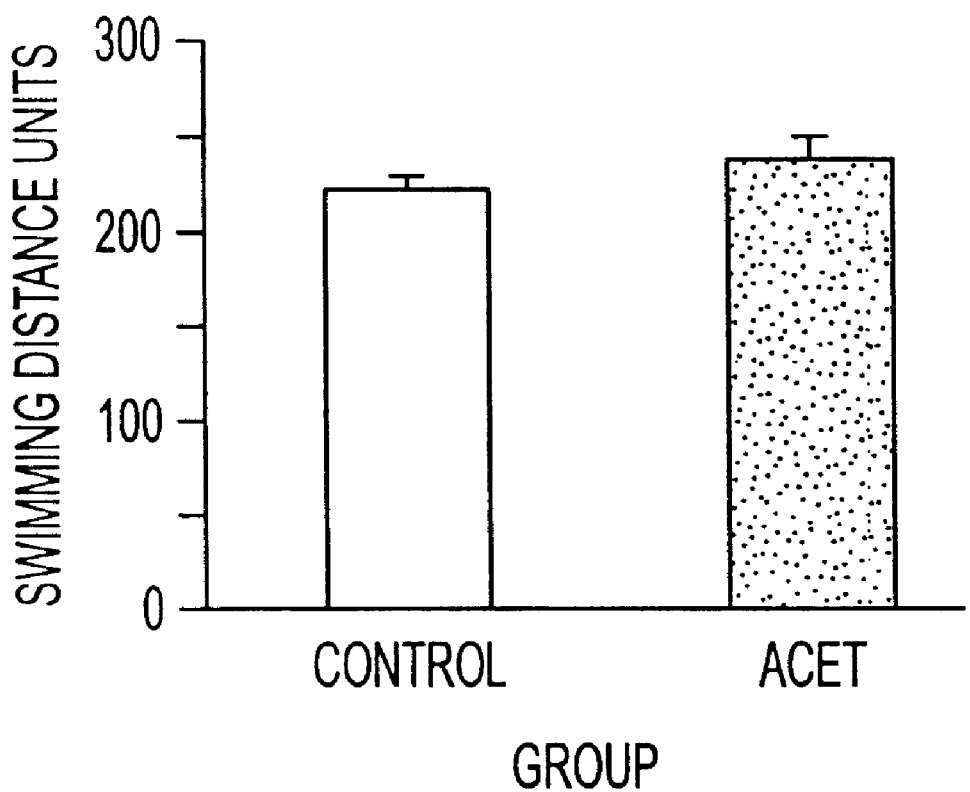

As shown in FIGS. 8A, 8B, 8C1 to 8C2, 8D1 to 8D2 and 8E, carbonic anhydrase inhibitors impair rat spatial memory in vivo. FIG. 8A shows the mean (±SE) escape latency across 16 trials ($F_{15,270}$=22.93, P<0.0001) in the watermaze by rats given a single dose (indicated with arrows) of saline (Saline, 0.5 ml) or ACET (5 mg/0.5 ml/day ip). FIG. 8B illustrates the percentage ratio in escape latency of the 1$^{st}$ trial of the day between the two groups. FIGS. 8C–8E show the quadrant preference of saline-(n=10; ** P<0.0001; 8C1) and ACET-injected rats (n=10; FIG. 8D1) and swimming distance (in 1 min; FIG. 8E). A platform for escape was placed in quadrant 4 during training. FIGS. 8C2 and 8D2 show paths taken by representative rats with quadrant numbers indicated.

Figure 9A:
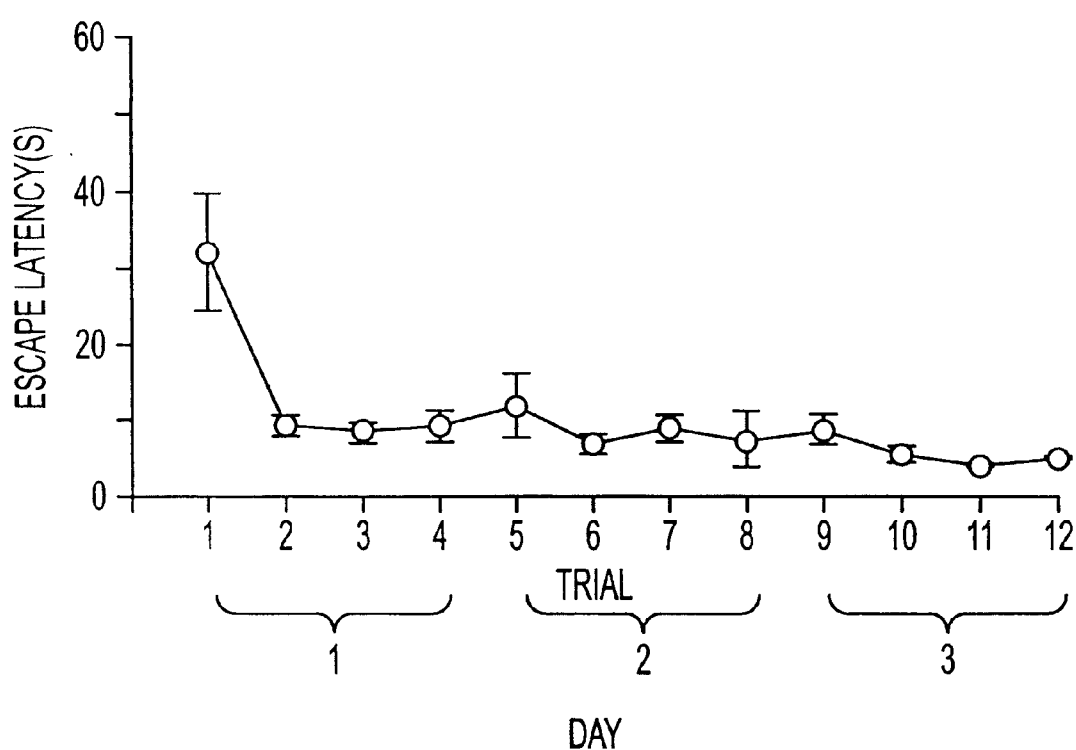
Figures 1, 9B:
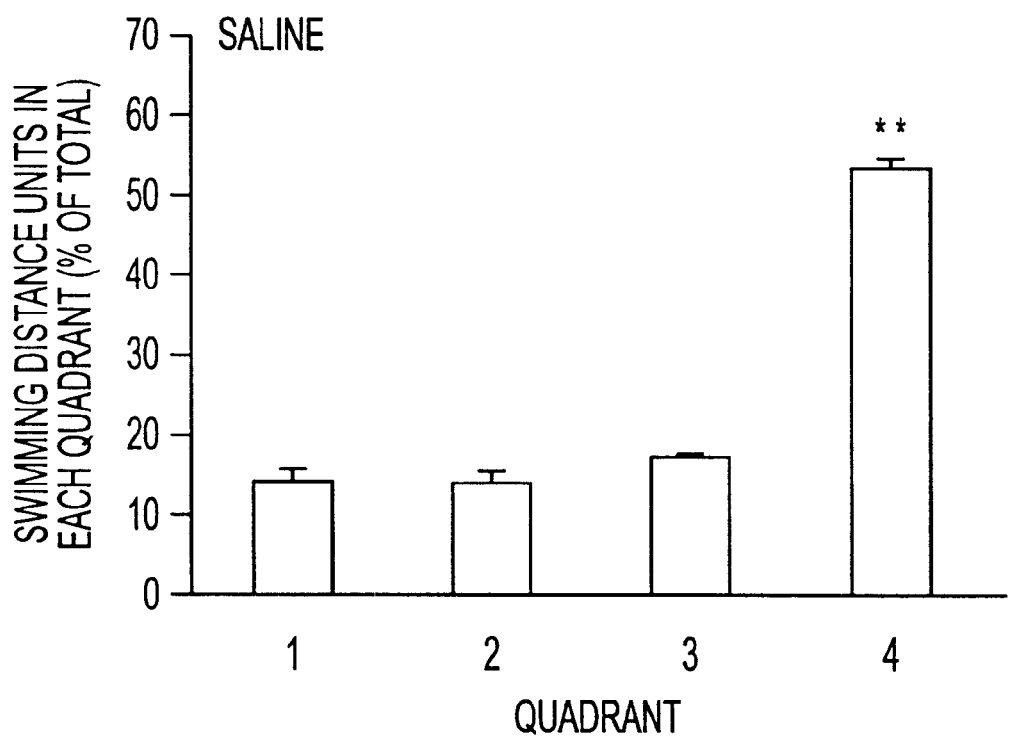
Figures 2, 9B:
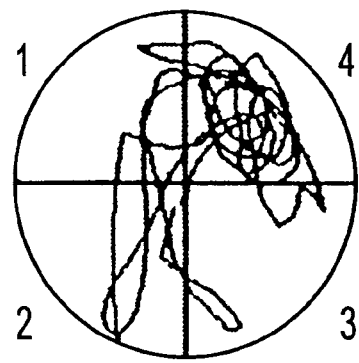
Figures 1, 9C:
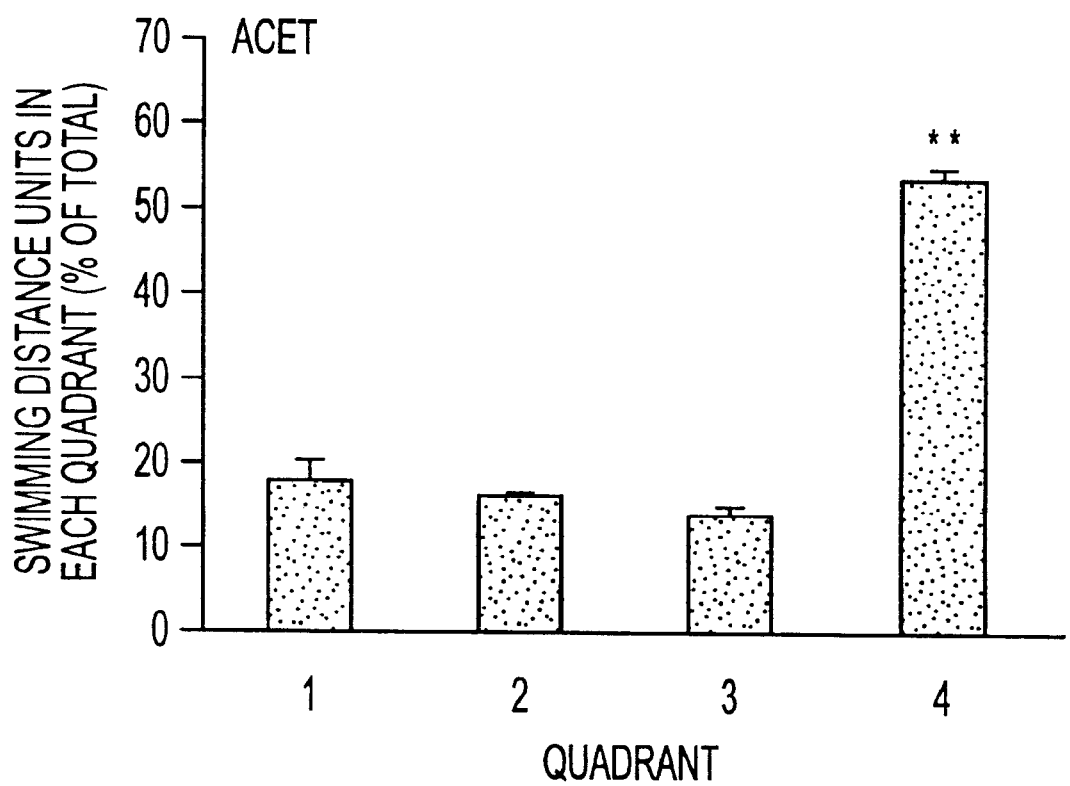
Figures 2, 9C:
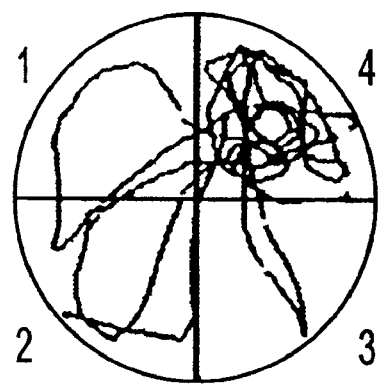

As seen in FIGS. 9A, B and C, ACET administration does not affect retrieval of formed spatial memory. FIG. 9A shows the escape latency of the control rats during three more days of training trials. FIGS. 9B1 and 9C1 illustrate quadrant preference of these rats after a single dose of saline (0.5 ml, n=5; FIG. 9B1) or ACET (5 mg/0.5 ml, n=5; FIG. 9C1). No significant difference in quadrant preference (P>0.05) was observed between the saline- and ACET-injected rats. FIGS. 9B2 and 9C2 show paths taken by representative rats with quadrant numbers indicated.

Reducing $HCO_3^-$ formation with a carbonic anhydrase inhibitor that can pass through the blood brain barrier can affect rat spatial memory. In rats, an intraperitoneal (ip) dose of ACET produces a peak concentration in the blood within 1 hr and is cleared by 2 h (Cassin, S., Beck, M. J., Travis, P., Sanders, S., and Otis, A. B., The Effect of Carbonic Anhydrase Inhibition in Exercising Rats, Brooks Air Force Base, TX: US Air Force School of Aerospace Medicine, 1963, pp. 1–6; Sone, M., Sei, H., Morita, Y., Ogura, T., and Sone, S., The effects of acetazolamide on arterial pressure variability during REM sleep in the rat, Physiol. Behav. 63: 213–218, 1998). Effects of ACET on spatial learning (Meiri et al. 1998) were determined during this short period.

A single dose of ACET (14–18 mg/kg, sufficient to reduce the EEG $\theta$ power by about 50% at maximum during rat REM sleep; Sone et al. 1998) was sufficient to produce memory impairment (FIG. 8A). The ACET group showed a strikingly smaller reduction ($F_{1,18}$=34.79, P<0.0001) in escape latency during training trials than the saline group did. The memory impairment became more significant as the training days progressed and was particularly evident in the first trial (65–70 min after the injection) of each successive day (FIGS. 8A and B). The latter might reflect a relatively normal short-term (vs. long-term) learning after ACET or more likely influence of a rapid clearance of the drug (Cassin et al. 1963; Sone et al. 1998). Quadrant tests 24 h after the last training trial revealed that control rats spent the majority of their time searching in the quadrant (Quadrant 4; FIG. 8C1) where the platform was previously placed and had been removed ($F_{3,36}$=183.9, P<0.0001; ANOVA and Newman-Keuls post hoc test), whereas the ACET group showed no preference to a particular quadrant ($F_{3,36}$=1.59, P=0.21; FIG. 8D1).

The total swimming distances, however, did not differ between the two groups (FIG. 8E; P>0.05), indicating that ACET did not grossly affect their sensory or locomotor activities. Neither was memory retrieval affected by ACET. The control rats were trained for 3 more days (FIG. 9A) and received the single injection of either ACET or saline 24 h after the last training trial. Sixty-five to seventy min after the injection, a quadrant test in ACET-injected rats showed no significant difference (P>0.05) in quadrant 4 preference ($F_{3,16}$=132.9, P<0.0001; FIG. 9C) from that of the saline control rats ($F_{3,16}$=306.4, P<0.0001; FIG. 9B). These results indicate that once formed, memory and its recall, as well as the sensory stimuli that elicit recall, are not vulnerable to ACET. During the experimental periods, no rats showed any apparent sign of discomfort or abnormal behaviors such as hypo- or hyperactivity.

Discussion

In vitro $\theta$ Rhythm and Cholinergic Involvement

The CCH-induced $\theta$ of this experiment is consistent with the in vitro $\theta$ previously reported by many other groups (e.g., Golebiewski H, Eckersdorf B, and Konopacki J., Cholinergic/GABAergic interaction in the production of EEG theta oscillations in rat hippocampal formation in vitro., *Acta Neurobiol Exp* 56: 147–153, 1996; Konopacki J, and Golebiewski H., Theta-like activity in hippocampal formation slices: cholinergic-GABAergic interaction., *NeuroReport* 4: 963–966, 1993;Huerta and Lisman 1995; Vertes and Kocsis 1997) and appears to be fundamentally identical to the $\theta$ rhythm in vivo for its sensitivity to muscarinic receptor antagonists, dependence on GABAergic interneurons, and independence of glutamatergic inputs. Acetylcholine's activation of muscarinic receptors on pyramidal cells is considered to be modulatory and much too slow to generate rhythmic $\theta$ directly (Dutar et al. 1995; Vertes and Kocsis 1997). The ineffectiveness of blocking glutamatergic inputs on the $\theta$ is also consistent with the evidence that during e oscillations in vivo CA3 neurons rarely reach action potential threshold (Bland, B. H. and Wishaw, I. Q., Generators and topography of hippocampal theta (RSA) in the anaesthetized and freely moving rat, Brain. Res. 118: 259–280, 1976; Fox, S. E. and Ranck, J. B. Jr., Electrophysiological characteristics of hippocampal complex-spike cells and theta cells, Exp. Brain. Res. 41: 399–410, 1981) and excitatory inputs from CA3 are unlikely to contribute to CA1 $\theta$ (Thompson, L. T. and Best, P. J., Place cells and silent cells in the hippocampus of freely-behaving rats, J. Neurosci. 9: 2382–2390, 1989; Soltesz and Deschenes 1993; Ylinen et al. 1995). The effectiveness of the specific $GABA_A$ receptor antagonist BIC in eliminating the postsynaptic response and $\theta$ activity strongly suggests that GABA$_B$ receptor activation did not contribute significantly to the responses. The CA1θ activity does, however, appear to be distinct from the activity oscillations that were BIC-insensitive, involved epileptiform bursting, and were generated by CA3 neurons in one report (Williams, J. H. and Kauer, J. A., Properties of carbachol-induced oscillatory activity in rat hippocampus, J. Neurophysiol. 78: 2631–2640, 1997). This difference may depend on the preparations or age of the animals. In their study, slices were obtained from younger animals so that cells may have a high intracellular Cl$^-$ concentration, due to the lack of a developmentally expressed Cl$^-$-extruding K$^+$/Cl$^-$ co-transporter in early age (Rivera, C., Voipio, J., Payne, J. A., Ruusuvuori, E., Lahtinen, H., Lamsa, K., Pirvola, U., Saarma, M., and Kaila, K., The K$^+$/Cl$^-$ co-transporter KCC2 renders GABA hyperpolarizing during neuronal maturation, Nature 397: 251–255, 1999).

Involvement of muscarinic receptors in hippocampal θ induction has been well established. Low-frequency MS/DBv stimulation activates cholinergic inputs to the hippocampus and drives θ in vivo (Descarries et al. 1997). Microinfuisions of CCH or eserine into areas including CA1 induce an atropine-sensitive hippocampal θ activity in vivo (Rowntree, C. I. and Bland, B. H., An analysis of cholinoceptive neurons in the hippocampal formation by direct microinfusion, Brain Res. 362: 98–113, 1986). Atropine administration has been found to eliminate hippocampal θ in vivo (Brazhnik, E. S. and Vinogradova, O. S., Control of the neuronal rhythmic bursts in the septal pacemaker of theta-rhythm: effects of anaesthetic and antichlinergic drugs, Brain Res. 380: 94–106, 1986; Vertes and Kocsis 1997). The effectiveness of muscarinic antagonists does not mean, however, that there is only one form of θ. In anesthetized rats, atropine eliminates θ (Stewart, M. and Fox, S. E., Detection of an atropine-resistant component of the hippocampal theta rhythm in urethane-anesthetized rats, Brain Res. 500: 55–60, 1989). Under such conditions, an unconventional small "residual θ" was described, that, in the absence of θ, could be shown by using MS/Dev neurons that discharged rhythmically to trigger hippocampal EEG in analysis (Stewart and Fox 1989). The involvement of serotonergic transmission has been proposed (Vanderwolf, C. H., Harvey, G. C., and Leung, L. W., Transcallosal evoked potentials in relation to behavior in the rat: effects of atropine, p-chlorophe ylalanine, reserpine, scopolamine and trifluoperazine, Behav. Brain Res. 25: 31–48, 1987). The particular role and importance of such an atropine-resistant component in memory remains to be established. Furthermore, intracellular θ activity of pyramidal cells has been claimed to result from depolarizing or hyperpolarizing membrane potential oscillations (Vertes and Kocsis 1997).

The θ activities induced in here were most likely evoked by muscarinic receptor activation, given their sensitivity to atropine. However, it is possible that multiple cell targets might be required for CCH to induce the θ activity. Although, it should not be ruled out entirely, nicotinic receptors are probably not involved because the interneurons in or near the stratum pyramidale and with axonal projections within and around this layer exhibit no nicotinic response (McQuiston, A. R. and Madison, D. V., Nicotinic receptor activation excites distinct subtypes of interneurons in the rat hippocampus, J. Neurosci. 19: 2887–2896, 1999).

HCO3$^-$-Mediated GABAergic Synaptic Depolarization

Encoding experiences into lasting memory may involve a qualitative diversity of synaptic plasticity (Otis, T., Zhang, S., and Trussell, L. O., Direct measurement of AMPA receptor desensitization induced by glutamatergic synaptic transmission, J. Neurosci. 16: 7496–7504, 1986; Kornhauser, J. M. and Greenberg, M. E., A kinase to remember: dual roles for MAP kinase in long-term memory, Neuron 18: 839–842, 1997; Brenowitz, S., David, J., and Trussell, L., Enhancement of synaptic efficacy by presynaptic GABA(B) receptor, Neuron 20: 135–141, 1998; Paulsen and Moser 1998), including changing operations of preexisting synapses and growing new ones. GABAergic postsynaptic depolarizing responses have been observed by several groups (Michelson, H. B. and Wong, P. K. S., Excitatory synaptic responses mediated by GABA$_A$ receptors in the hippocampus, Science 253: 1420–1423, 1991; Alkon, D. L., Sanchez-Andres, J. -V., Ito, E., Oka, K., Yoshioka, T., and Collin, C., Long-term transformation of an inhibitory into an excitatory GABAergic synaptic response, Proc. Natl. Acad. Sci. USA 89: 11862–11866, 1992; Kaila, K., Voipio, J., Paalasmaa, P., Paternack, M., and Deisz, R. A., The role of bicarbonate in GABA$_A$ receptor-mediated IPSPs of rat neocortical neurones, J. Physiol. Lond. 464: 273–289, 1993; Siklós, L., Rickmann, M., Joó, F., Freeman, W. J., and Wolff, J. R., Chloride is preferentially accumulated in a subpopulation of dendrites and periglomerular cells of the main olfactory bulb in adult rats, Neuroscience 64: 165–172, 1995; Staley, K. J., Soldo, B. L., and Proctor, W. R., Ionic mechanisms of neuronal excitation by inhibitory GABA$_A$ receptors, Science 269: 977–981, 1995; Rivera et al. 1999). The depolarization induced in the present study differs from that reported by Kalia et al. (Kalia, K., Lamsa, K., Smimov, S., Taira, S., and Voipio, J. Long-lasting GABA-mediated depolarization evoked by high-frequency stimulation in pyramidal neurons of rat hippocampal slice is attributable to a network-driven, bicarbonate-dependent K$^+$ transient. J. Neurosci. 17: 7662–7672, 1997), who applied a high-frequency train of pulses to the stratum radiatum to induce depolarizing responses that showed a slow time course but lasted for several seconds. Nevertheless, these experimental results are consistent with the evidence that GABAergic depolarization can be induced by enhancing HCO$_3^-$ conductance through GABA$_A$ receptor-channels in adult hippocampal cells, a response sensitive to carbonic anhydrase inhibitors (Kaila et al. 1993; Staley et al. 1995). Carbonic anhydrase exists in pyramidal cells (Pasternack, M., Voipio, J., and Kaila, K. Intracellular carbonic anhydrase activity and its role in GABA-induced acidosis in isolated rat hippocampal pyramidal neurones. Acta Physiol. Scand. 148: 229–231, 1993). Indeed, the θ activity and the reversed GABAergic postsynaptic responses were largely abolished by carbonic anhydrase inhibitors. The effectiveness of intracellular benzolamide, a membrane-impermeable carbonic anhydrase inhibitor, indicates that the response depends on activity of an intracellular enzyme. Supporting the functional importance of carbonic anhydrase activity in synaptic plasticity is also the result that a partial blockade of the enzyme activity in vivo markedly impaired retention of rat watermaze learning. HCO$_3^-$ has a reversal potential about −12 mV (Staley et al. 1995). With an increased HCO$_3^-$/Cl$^-$ permeability ratio, outward HCO$_3^-$ flux would depolarize the membrane at the resting membrane potential. Alteration in HCO$_3^-$ conductance and/or transmembrane concentrations (thus the driving force) would be expected to dramatically alter the synaptic response.

The existence of physiological regulators of carbonic anhydrase has been proposed in other contexts, including those that activate the anhydrase by facilitating its membrane association (Parkes, J. L. and Coleman, P. S., Enhancement of carbonic anhydrase activity by erythrocyte membranes., Arch. Biochem. Biophys., 275: 459–468, 1989). In molluscan neurons, the carbonic anhydrase-$HCO_3^-$ system has been found to be the most potent regulatory factor in intracellular pH regulation. Depolarized snail neurons, for example, were associated with increased proton conductance (e.g., Thomas R C, and Meech R W., Hydrogen ion currents and intracellular pH in depolarized voltage-clamped snail neurones., Nature 299: 826–828, 1982). Changes in intracellular pH could also alter ion channel function as well as metabolic activity. It remains to be determined whether intracellular pH is significantly altered or plays a role in the CCH-induced θ and/or regulation of memory behavior.

Phase Relationship of θ Activities of CA1 Pyramidal Cells and Interneurons

Two major classes of hippocampal CA1 neurons are the θ cells and the "place cells" (Paulsen and Moser 1998). The GABAergic interneurons, including basket cells and axoaxonic cells, have been called θ cells (Paulsen and Moser 1998). The basket interneurons are particularly active and express strongest rhythmic discharges (Cscsvari et al. 1999) when hippocampal EEG is dominated by θ rhythm. One basket interneuron selectively and perisomatically innervates approximately 1,000 pyramidal cells (Cobb et al. 1995) and thus can entrain a large population. The pyramidal neurons, on the other hand, are largely quiescent during θ rhythm associated with exploration, but a subpopulation shows strong firing that is highly correlated with specific locations in space (Dutar et al. 1995; Vertes and Kocsis 1997; Paulsen and Moser 1998). These "place" cells fire at all phases of the θ rhythm (O'Keefe and Recce 1993). Here, the results show that during θ oscillation, the GABAergic postsynaptic responses are altered. Gating through a postsynaptic mechanism, as described in the present study, could explain why some pyramidal cells become active while the vast majority of others remain silent during θ EEG, even if they are innervated by the same interneuron.

Every pyramidal cell is innervated by 10–12 GABAergic interneurons, preferentially making synapses on cell bodies, proximal dendrites, and axon initial segments of CA1 pyramidal cells (Buhl E H, Halasy K, and Somogyi P., Diverse sources of hippocampal unitary inhibitory postsynaptic potentials and the number of synaptic release sites., Nature 368: 823–828, 1994; Paulsen and Moser 1998 for review). If pyramidal cells were activated by rebound excitation from GABAergic inhibition, one would expect that pyramidal cells should discharge when interneurons become silent. This may be the case in anesthetized states. The intracellular θ activity of CA1 pyramidal cells when recorded under anesthesia have often been reported to fire out-of-phase, delayed about a half cycle (Soltesz and Deschenes 1993; Ylinen et al. 1995). In behaving animals or during REM sleep, however, the earlier discharge peaks of these interneurons precede peaks of population activity of pyramidal cells during θ activity and both pyramidal cell firing and interneuronal discharge occur within the same θ phase period (Cscsvari et al. 1999). Anesthesia is known to attenuate a large peak of θ, revealing rhythmic hyperpolarization of pyramidal cells from basket interneurons (Ylinen et al. 1995). Thus, the θ activity during exploration or induced by cholinergic agonists in vitro seems incomparable to the θ under anesthesia (Ylinen et al. 1995; Muir, G. M. and Bilkey, D. K. Synchronous modulation of perirhinal cortex neuronal activity during cholinergically mediated (type II) hippocampal theta. Hippocampus 8: 526–532, 1998).

Not only does the discharge phase relationship between pyramidal cells and interneurons differ between the anesthetized and behaving animals, but the phase relationship is also dynamic. In behaving animals, the phase forward shift of the discharges of place cells on each θ cycle occurs during traversal of the place field of the cell (O'Keefe and Recce 1993; Shen et al. 1997). Place cells thus fire in phase with progressively stronger GABAergic inputs from interneurons and at earlier phases of the θ cycles as the rat moves toward the center of their place field (FIG. 7B; O'Keefe and Recce 1993; Shen et al. 1997; Csicsvari et al. 1999). Mechanism(s) responsible for the θ initiation or entraining of the pyramidal cell activity should be able to code for timing (Trussell, L. O. Synaptic mechanisms for coding timing in auditory neurons. Annu. Rev. Physiol. 61: 477–496, 1999) or entrain pyramidal cells at different θ phases, including those with minimal delay (Csicsvari et al. 1999). A rebound excitation following hyperpolarization is unlikely to have such multiphase capability as the interneurons become more active during θ-related activity. A brief switch toward or to GABAergic depolarization would be more effective and reliable in processing dynamic information. Strong GABAergic inputs after the synaptic switch can entrain the activity of pyramidal cells so that the delay would be relatively short and evoke an "in phase" activity.

The present results suggest that the GABAergic entraining could result in three ways. In a small percentage of cells, CCH was able to elevate the reversal potential to levels that were above the threshold for spike activity. GABAergic inputs thus could directly drive, even if briefly, activity of the pyramidal cells with sufficient transformation of hyperpolarizing to depolarizing responses. The reversed response, although often not strong enough to reach threshold by itself, can entrain the pyramidal cells when stimulated at a θ frequency (FIGS. 7A1 to 7A3, 7B1 to 7B2, and 7C1 to 7C5). Furthermore, the reversed response can effectively enhance weak excitatory inputs to reach threshold (FIGS. 7C1 to 7C5) (Sun et al. 1999). When the inputs are not very strong and require summation of multiple synaptic activation or other associative inputs, such as glutamatergic inputs (Sun et al. 1999) to reach the threshold, the entrained action potentials are likely to be delayed. It should also be noted that for this summation effect to occur, there must be sufficient spatial proximity on the pyramidal cells for the glutamatergic excitatory postsynaptic potentials to spread from the dendrites to the somata where they would interact with the transformed GABAergic IPSPs. Thus, "place cells" are capable of firing at all phases of the θ rhythm in relation to the activity of GABAergic interneurons.

This Example shows reversed, $HCO_3^-$-dependent GABAergic postsynaptic responses and their effectiveness in entraining activity of pyramidal cells. The most reasonable explanation for our results is an essential requirement for carbonic anhydrase activity in the molecular signaling pathways, for learning and memory. This result surprisingly offers an explanation for the occurrence of mental retardation in carbonic anhydrase II-deficient patients (Sly, W. S. and Hu, P. Y. Human carbonic anhydrases and carbonic anhydrase deficiencies. Annu. Rev. Biochem. 64: 375–401, 1995). Carbonic anhydrase is very efficient and may act as a functional switch. The effectiveness of inhibiting carbonic anhydrase to impair rat spatial memory was not predicted by evidence of bicarbonate-dependent GABAergic depolarization, as defined in vitro. That is spatial memory is a much more complex phenomenon than depolarization. The critical role of $HCO_3^-$ in θ activity also surprisingly explains the fact that ACET is effective in the treatment of central sleep apnea or epilepsy, causing somnolence together with significant decreases in centrally originated θ rhythm-related fluctuations in cardiorespiratory functions (Sone et al. 1998). ACET-regulated $HCO_3^-$ gradients appear important for acquisition of memory rather than retrieval from formed memory. Such compounds may have clinical value when temporarily suppressed memory is beneficial (e.g., in surgery or post-traumatic-stress-disorder).

Example 2

Encoding an experience into a lasting memory is thought to involve an altered operation of relevant synapses and a variety of other subcellular processes, including changed activity of specific proteins. The following example demonstrates that co-applying (associating) membrane depolarization of rat hippocampal CA1 pyramidal cells with intracellular microinjections of calexcitin (CE), a memory-related signaling protein, induces a long-term transformation of inhibitory postsynaptic potentials from basket interneurons (BAS) into excitatory postsynaptic potentials. This synaptic transformation changes the function of the synaptic inputs from excitation filter to amplifier, is accompanied by a shift of the reversal potential of BAS-CA1 postsynaptic potentials, and is blocked by inhibiting carbonic anhydrase or antagonizing ryanodine receptors. Effects in the opposite direction are produced when anti-CE antibody is introduced into the cells, whereas heat-inactivated CE and antibodies are ineffective. These data suggest that CE is actively involved in shaping BAS-CA1 synaptic plasticity and controlling information processing through the hippocampal networks.

Introduction

Synapses are considered a critical site at final targets through which memory-related events realize their functional expression (Kornhauser, J. M. & Greenberg, M. E. (1997) Neuron 18, 839–842), whether the events involve changed gene expression and protein translation, altered kinase activities, or modified signaling cascades. A few proteins have been implicated in associative memory. These include $Ca^{2+}$/calmodulin II kinases, protein kinase C (PKC), and calexcitin (CE), a recently cloned and sequenced 22-kDa learning-associated $Ca^{2+}$-binding protein (Alkon, D. L., Nelson, T. J., Zhao, W. Q. & Cavallaro, S. (1998) Trends Neurosci. 21, 529–537; Nelson, T. J., Collin, C. & Alkon, D. L. (1990) Science 247, 1479–1483), and the type II ryanodine receptors (RyR). Levels of CE in identified mollusk neurons change with Pavlovian conditioning (Nelson et al. 1990). CE is also a substrate of PKC and may play a role in pathophysiology of Alzheimer disease (Alkon et al. 1998). It increases neuronal excitability in Hermissenda and mammalian hippocampus and cerebellum, whereas anti-CE antibodies react with 22-kDa protein fractions from mammalian brain extracts (Alkon et al. 1998). Furthermore, biochemical and patch-clamp studies indicate that CE activates the RyR to release intracellular $Ca^{2+}$ from the endoplasmic reticulum (Alkon et al. 1998). These functional similarities in diverse species suggest homologous protein targets and mechanistic conservation across evolution.

Abbreviations

ACET, acetazolamide; BAPTA, 1,2-bis(2-aminophenoxy)ethane-N,N,N',N'-tetraacetic acid; BAS, basket neurons; CA, carbonic anhydrase; CE, calexcitin; EPSPs, excitatory postsynaptic potentials; GABA, γ-aminobutyrate; IPSPs, inhibitory postsynaptic potentials; KYN, kynurenate; PSP, postsynaptic potential; RR, ruthenium red; RyR, ryanodine receptors; SCH, Schaffer collateral pathway.

Methods

Chemicals. Cloned CE (without the C-terminal P-loop) containing a $His_9$ leader sequence was expressed in BL21 (DE3) Escherichia coli cells and purified by repeated affinity chromatography on $Ni^{2+}$-charged His-Bind columns (Novagen). Anti-CE antibody was raised in rabbits, by using peptide Ac-DVNDTSGDNIIDKHEYSTC-NH, corresponding to positions 115–133 of CE, conjugated to keyhole limpet hemocyanin(KLH; linked via C-terminal cysteine). The antibody was effective against nondenatured CE only. Agents were either injected into the recorded cells through the recording electrodes: CE, anti-CE antibody, ruthenium red (RR), or 1,2-bis(2-aminophenoxy)ethane-N,N,N',N'-tetraacetic acid (BAPTA); or into the perfusion medium: kynurenic acid (KYN; Sigma; 500 μM; adjusted to pH 7.4 with 1 M NaOH; Sun, M. -K. (1996) Pharmacol. Rev. 48, 465–494), bicuculline methiodide (Sigma; 10 μM), acetazolamide (ACET; Sigma; 1 or 10 μM), or benzolamide (gift from T. H. Maren, University of Florida, Gainesville). For injections of the proteins, electrode tips were filled with 1 μl (260 ng/μl) of cloned CE, heat-inactivated CE, or anti-CE antibody or heat-inactivated anti-CE antibody, respectively, in 1 M potassium acetate (KOAc) and backfilled with 3 M KOAc (pH adjusted to 7.25). The proteins, BAPTA (~10 mM), and RR were injected during pulse cycles controlled with PCLAMP program (the proteins and BAPTA: −2.0 nA, 700 ms on 33% duty cycles for 15 min; RR: +0.5 nA, 500 ms 50% on duty cycles through 2 mM solution for 10 min). Heat-inactivated proteins (100° C. for 5 min) were used as control. For carbonic anhydrase (CA) activity measurement, a 1-μl sample of purified CA (Sigma) and rat brain homogenate in 1 ml of 0.1 M Tris-HCl (pH 7.4) was bubbled at 4° C. with $CO_2$ from a gas cylinder. pH changes were monitored with an Orion 9802 BH pH electrode connected to a data acquisition system via a VWR 8010 pH meter.

Electrophysiology. Male Sprague-Dawley rats (130–180 g) were decapitated and the brains were removed and cooled rapidly in a modified artificial cerebrospinal fluid (aCSF) (about 4° C.), bubbled continuously with 95% $O_2$/5% $CO_2$. Hippocampi were sliced (400 μm), placed in oxygenated aCSF (124 mM NaCl/3 mM KCl/1.3 mM $MgSO_4$/2.4 mM $CaCl_2$/26 mM $NaHCO_3$/1.25 mM $NaH_2PO_4$/10 mM glucose), and subfused (2 ml/min) with the oxygenated aCSF in an interface chamber and allowed to equilibrate for a minimum of 1 hr at 30–31° C. Hepes was used to replace $NaHCO_3$ in non-bicarbonate buffer solution, which was bubbled with 100% $O_2$ (pH adjusted to 7.38–7.40). CA1 pyramidal cells were recorded intracellularly with sharp electrodes. Intracellular microelectrode recording rather than whole-cell clamp avoids immediate internal perfusion of the test proteins and agents into the cells and marked run-down of γ-aminobutyrate (GABA)-evoked currents. A control period without immediate influence of test proteins is crucial for evaluating test results. KOAc (3 M, pH 7.25)-filled electrodes (tip resistance 60–120 MΩ) were positioned in the area of CA1. A bipolar stimulating electrode (Teflon-insulated PtIr wire 25 μm in diameter) was also placed in the stratum pyramidale, within 200 μm from the recording electrode, for stimulation of basket interneurons (BAS) (50 μA). In some experiments, an additional bipolar electrode was placed in the stratum radiatum to stimulate the Schaffer collateral pathway (SCH). CA1 neurons with stable resting membrane potential more negative than −70 mV were studied. Unless otherwise mentioned, test stimuli were applied at frequency of 1 per minute (0.017 Hz). Signals were amplified with AxoClamp-2B amplifier and digitized and stored by using a DigiData 1200 with the PCLAMP6 data collection and analysis software (Axon Instruments) and a Pentium PC computer. Experiments in which >20% variations in the evoked inhibitory postsynaptic potentials (IPSPs) during a 10 min control period occurred were discarded. Percent baseline PSP at each minute was calculated by dividing its value by baseline PSP then multiplying the result by 100. Baseline PSP was the mean of 10 min before treatments in each cell. A negative sign was added to indicate its inhibitory nature so that −100% is baseline IPSP and a positive value indicates an excitatory response. Differences were considered significant at P<0.05.

Results

Figure 10A:
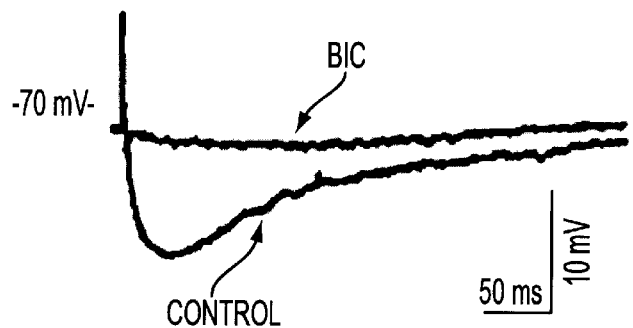
Figure 10B:
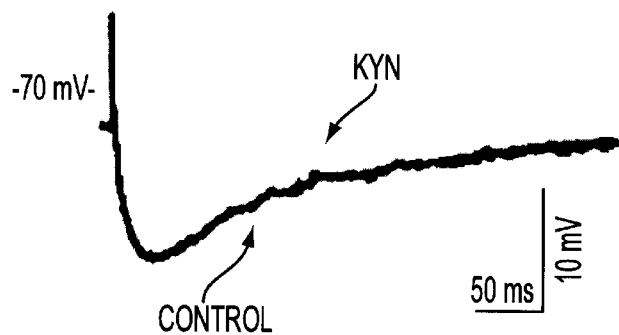
Figure 10C:
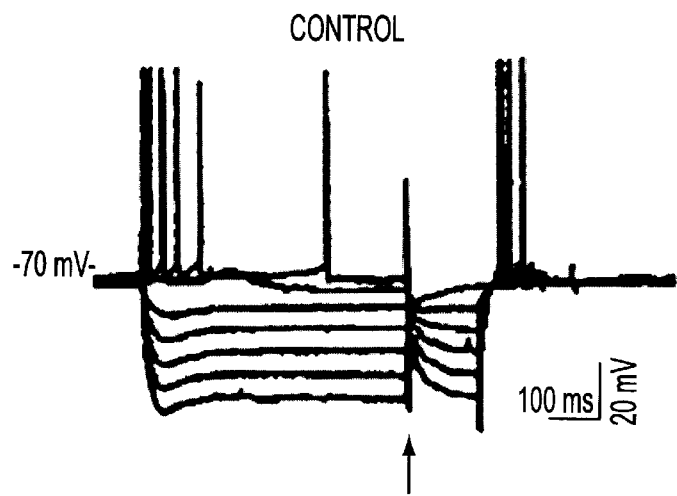
Figure 10D:
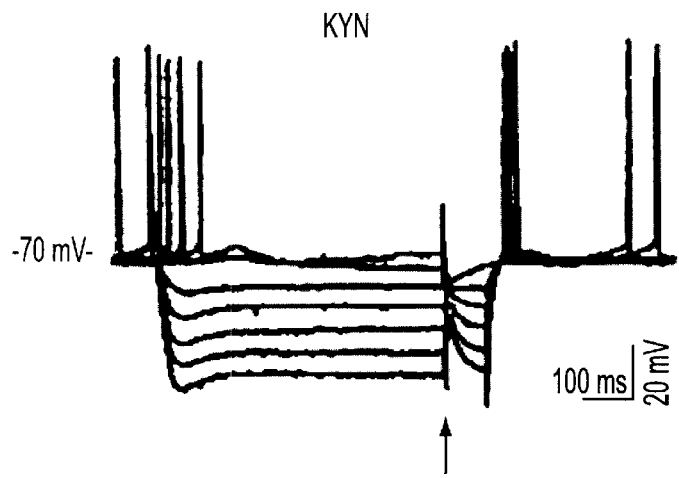
Figure 10E:
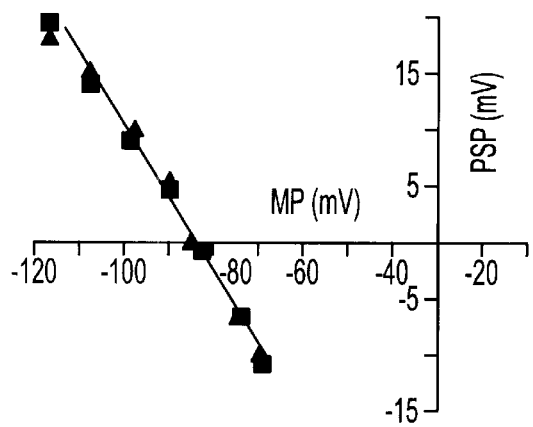
Figure 10F:
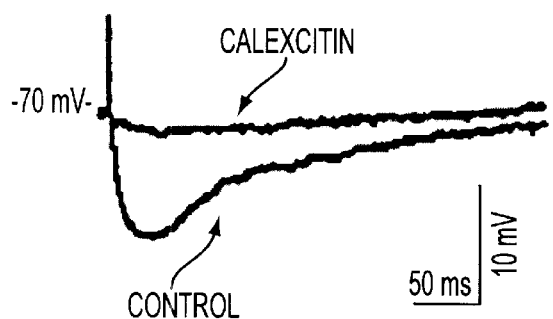
Figure 10G:
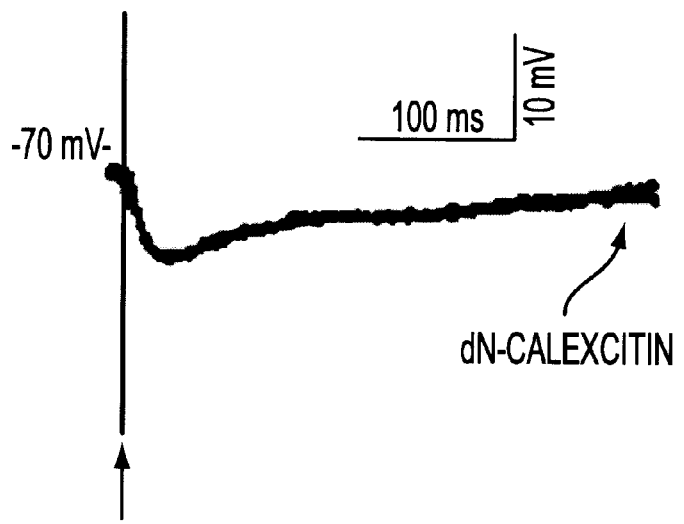
Figure 10H:
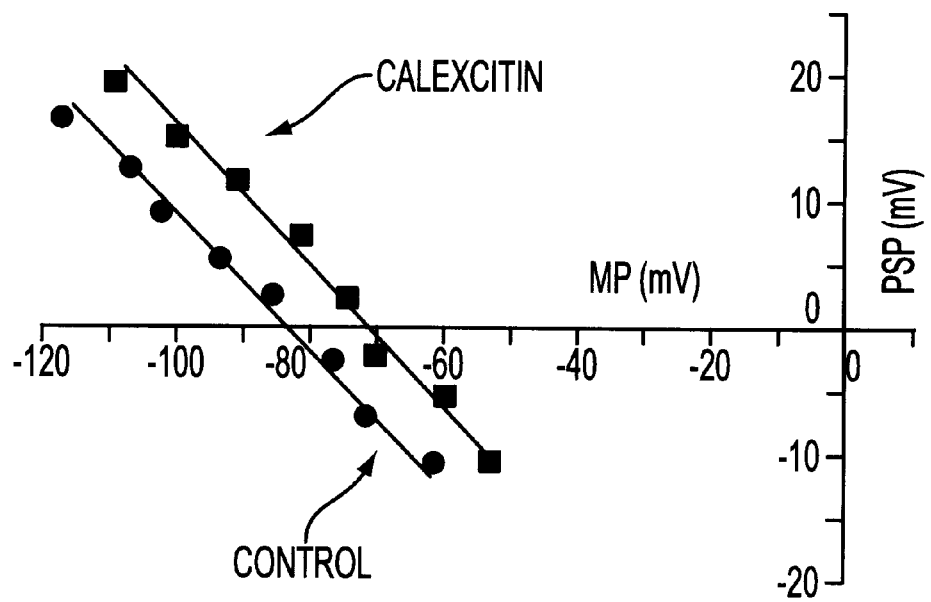
Figures 1, 10I:
Figures 2, 10I:
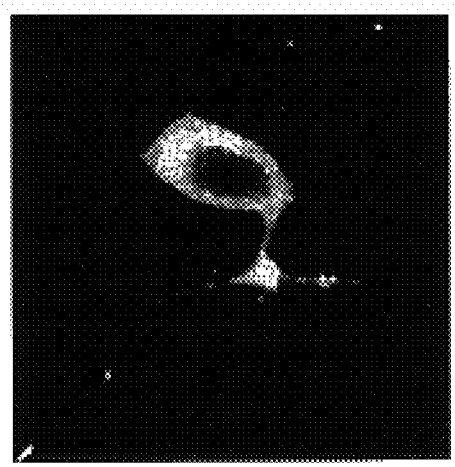
Figure 10J:
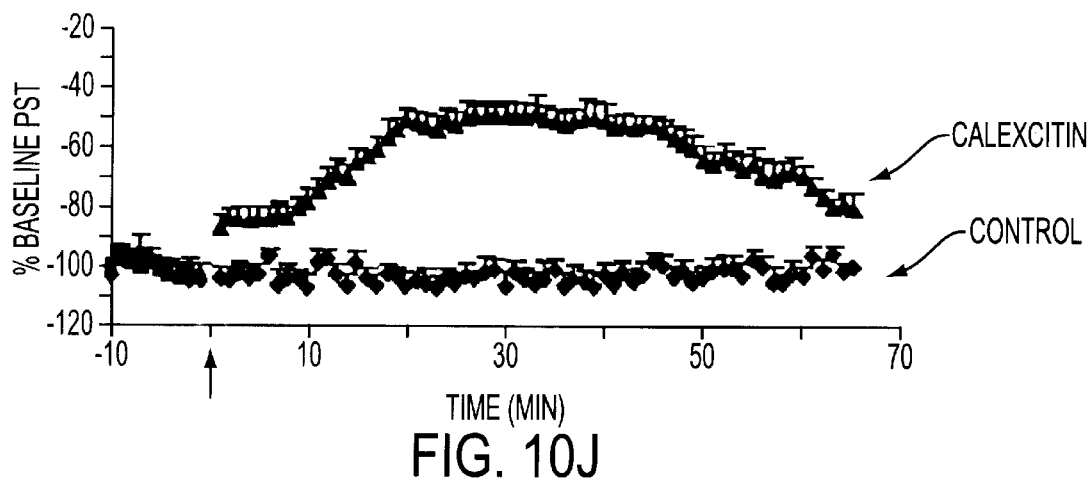
Figure 10K:
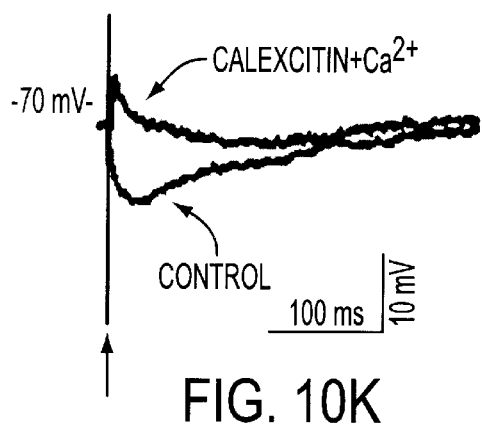
Figure 10L:
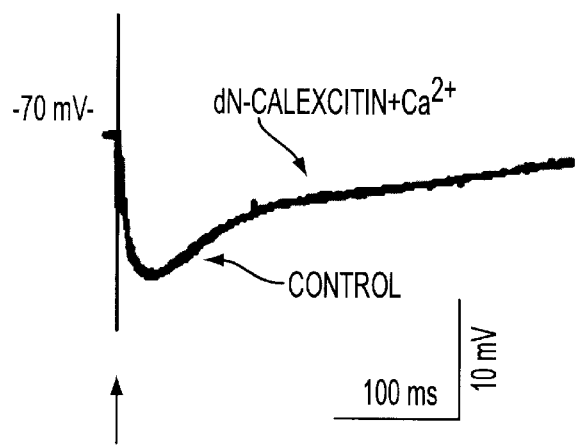
Figure 10M:
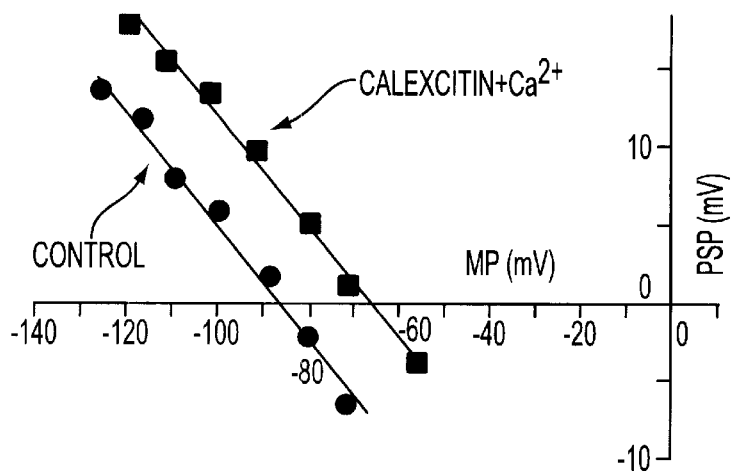
Figure 10N:
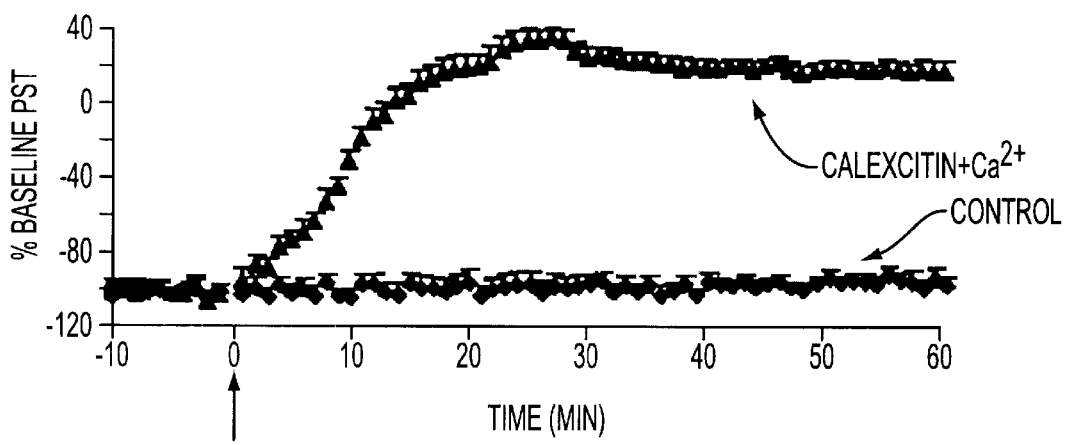
Figure 10O:
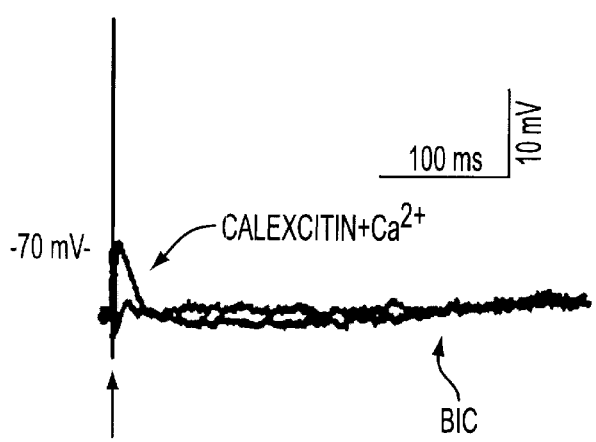

As seen in FIGS. 10A–O, CE transforms BAS-CA1 synapses. Bicuculline (BIC, 1 μM, 30 min) eliminates (FIG. 10A), whereas KYN (500 μM, 20 min) does not alter (FIG. 10B), the evoked IPSPs. The relationship between the evoked BAS-CA1 PSP at different membrane potentials (MPs) (FIGS. 10C and 10D) in a CA1 pyramidal cell can be described with a straight line (FIG. 10E), determined by the least sum squares criterion, and is not altered by KYN (FIGS. 10C and D). CE reduces BAS-CA1 IPSP (FIG. 10F; two overlapping traces) and shifts the PSP-MP curve to the right (FIG. 10H). Heat-inactivated CE (dN-Calexcitin) is ineffective (FIG. 10G). Microinjections of CE conjugated with the green fluorescent Alexa488 (Molecular Probes) results in strong labeling of the cell body and portion of the dendrites in focus (FIGS. 10I-1, active form, and 10I-2, heat-inactivated; after fixation with 10% paraformaldehyde/saline overnight and cutting to 40 μm thick, shown ×400), indicating the efficacy of the CE microinjection. In FIG. 10J, time courses of the response to CE or heat-inactivated CE injection (Control), each point represents the mean IPSP magnitudes+SEM normalized to the average of the pre-CE IPSPs. PST, postsynaptic transformation. The vertical arrow indicates the time of injection. Associating CE injection with postsynaptic depolarization (0.4–0.6 nA during the off period with the current intensities adjusted to elicit 4–8 spikes per s) transforms BAS-CA1 inhibitory PSP into an excitatory one (FIG. 10K) and produces a further shift of the PSP-MP curve to the right (FIG. 10M). Associating heat-inactivated CE with postsynaptic depolarization (0.4–0.8 nA at the off period with current intensities adjusted to evoke 4–8 spikes per s) does not alter BAS-CA1 IPSP (FIG. 10L). Average responses of BAS-CA1 PSP after associating either CE (CE+$Ca^{2+}$) or heat-inactivated CE (Control) are shown in FIG. 10N. The transformed synaptic response is eliminated by 1 μM bicuculline (FIG. 10O; 30 min).

Effects of CE on synaptic function were investigated on synaptic inputs from GABAergic BAS to CA1 pyramidal cells. Each GABAergic interneuron powerfully inhibits some 1,000 pyramidal cells, providing widespread control over hippocampal networks (McMahon, L. L. & Kauer, J. A. (1997) *Neuron* 18, 295–305; Buhl, E. H., Halasy, K. & Somogyi, P. (1994) *Nature* (London) 368, 823–828; Cobb, S. R., Buhl, E. H., Halasy, K., Paulsen, O. & Somogyi, P. (1995) *Nature* (London) 378, 75–78). A singlepulse stimulation within the stratum pyramidale produced IPSPs in CA1 pyramidal neurons at their resting membrane potential (FIG. 10A). The IPSPs (−8.4±0.3 mV, n=8, P<0.05) were abolished (reduced by 95.1±3.2%, n=8, P<0.05, paired t test) by bicuculline (1 μM, 30 min), a $GABA_A$ receptor antagonist (Sun 1996), indicating that the evoked IPSPs are mediated largely, if not exclusively, by activation of BAS-CA1 pathway and are GABAergic. In some cases, a small but delayed inhibitory component remained in the presence of bicuculline (not shown), possibly representing an incomplete-blockade of the $GABA_A$ receptor or $GABA_B$ receptor-mediated component.

KYN (Sun et al. 1996; Collingridge, G. L. & Lester, A. J. (1989) *Pharmacol. Rev.* 40, 143–209), a competitive antagonist for both N-methyl-Daspartate (NMDA) and non-NMDA ionotropic subtypes, receptors for the most dominant excitatory inputs to CA1 pyramidal cells, at 500 μM (20 min; Collingridge et al. 1989) effectively eliminated SCH-CA1 excitatory postsynaptic potentials (EPSPs) (by >90%) but did not increase BAS-CA1 IPSPs (FIG. 10B). In the presence of KYN, the BAS-CA1 IPSP (−8.1±0.4 mV, n=7, P<0.05) did not differ (P>0.05) from that of pre-KYN (−8.0±0.3 mV, n=7, P<0.05), indicating the lack of a hidden, significant glutamatergic depolarizing component in the BAS-CA1 IPSPs.

The BAS-CA1 IPSPs were induced at different membrane potentials (FIGS. 10C and D) and were found to reverse at a single membrane potential (−79.4±0.4 mV, n=59). No minor component was detected that exhibited a different reversal potential (FIGS. 10C and D). The relationship between BAS-CA1 PSPs and membrane potentials can be described with a straight line, not affected by KYN (FIG. 10E). The reversal potential in the presence of KYN was −78.9 mV (±0.7 mV) and did not significantly differ (n=7, P>0.05) from pre-KYN values (−78.7±0.6 mV).

CE, applied postsynaptically into single pyramidal cells, produced a lasting (>1 hr) reduction in BAS-CA1 IPSP (FIG. 10F and J; Table 1). The effect resulted from biological activity of CE, since heat-inactivated CE was ineffective (FIG. 10G and J; Table 1). Membrane input resistance was altered neither by CE (post-CE: 83.7±2.5 MΩ vs. pre-CE: 83.6±2.6 MΩ, n=10, P>0.05) nor by heat-inactivated CE (post-CE: 81.3±1.8 MΩ vs. pre-CE: 80.6±1.6 M, n=8, P>0.05). Microinjections (with the same parameters used in the protocol) of CE conjugated with a green fluorescent Alexa488 resulted in strong labeling of the cell body and a portion of the dendritic tree in the plane of focus (FIG. 10I1), indicating the efficacy of the CE microinjections. Similar intensity of labeling of the cells was observed when heat-inactivated conjugated CE was microinjected (FIG. 10I2). Effects of CE on $K^+$ channels were evident as a reduction in after-hyperpolarization (from −4.7±0.3 mV to −0.5±0.2 mV, n=10, P<0.05) and a prolongation of the interval between brief intracellular depolarizing pulses (1 ms, 1–4 nA) sufficient to evoke action potentials and the time required for the membrane potential to repolarize to its prestimulation level (from 39.5±1.9 ms to 53.4±2.3 ms, n=10, P<0.05).

CE-induced reduction of BAS-CA1 PSPs does not appear to result from a simple blockade of a receptor-channel complex. Rather, CE caused a shift (FIG. 10H) of the relationship between BAS-CA1 PSPs and membrane potential to the right and of the reversal potential to more positive potentials (Table 1). The slope did not vary significantly on average. Heat-inactivated CE produced no such effect (Table 1).

TABLE 1

Effects of CE on BAS-CA1 PSPs of CA1 pyramidal cells

| Treatment | N | % PSPs Control | % PSPs Test | P | Reversal potential, mV Control | Reversal potential, mV Test | P |
|---|---|---|---|---|---|---|---|
| CE | 10 | −101.1 ± 42 | −49.9 ± 47* | | −79.0 ± 1.0 | −70.1 ± 1.4* | |
| CE (I) | 8 | −102.3 ± 3.5 | −106.0 ± 3.6$^{NS}$ | <0.05 | −77.6 ± 2.8 | −78.0 ± 2.4$^{NS}$ | <0.05 |
| CE + Ca$^{2+}$ | 10 | −102.3 ± 2.4 | +21.1 ± 4.5* | | −77.5 ± 0.9 | −66.4 ± 1.8* | |
| CE (I) + Ca$^{2+}$ | 8 | −102.5 ± 33 | −99.2 ± 2.5$^{NS}$ | <0.05 | −78.5 ± 1.6 | −78.8 ± 1.7$^{NS}$ | <0.05 |
| CE + Ca$^{2+}$ (BZA) | 7 | −99.8 ± 2.3 | +23.4 ± 3.7* | >0.05† | −78.9 ± 1.2 | −67.2 ± 2.0* | >0.05† |
| Anti-CE | 8 | −100.4 ± 31 | −121.9 ± 5.2* | | −79.5 ± 0.9 | −84.6 ± 2.2* | |
| Anti-CE (I) | 7 | −98.9 ± 2.9 | −100.9 ± 3.1$^{NS}$ | <0.05 | −79.2 ± 1.2 | −79.6 ± 1.8$^{NS}$ | <0.05 |

(I) heat–inactivated form; BZA, bath benzolamide. *, Significant difference (P < 0.05) as compared with pretreatments. $^{NS}$, no significant difference (P > 0.05) as compared with pretreatments. P indicates the significance of tests between the two groups; †, as compared with CE+ Ca$^{2+}$ group. Control values were obtained approximately 5 min before, while the test values were observed about 30 min. after the application of the proteins.

When CE microinjection was coincident with postsynaptic depolarization (0.4–0.6 nA during the interval between injection episodes, to load Ca$^{2+}$), the BAS-CA1 PSP was reversed to excitatory (FIGS. 10K and N and Table 1). This synaptic transformation lasted more than 1 hr (FIG. 10N) and did not occur suddenly, but rather as an extension of an initial gradual reduction in BAS-CA1 IPSPs (FIG. 10N). The transformed synaptic response was eliminated by bath application of bicuculline (1 μM; 30 min; FIG. 10O; by 95.6%±5.2%, n=6, P<0.05), indicating GABA$_A$ receptor mediation. The relationship between BAS-CA1 PSPs and membrane potential showed a further significant shift to the right with CE-depolarization pairing (FIG. 10M). Co-application of postsynaptic depolarization with heat-inactivated CE, however, had no such effects (FIGS. 10L and N; Table 1).

Figure 11A:
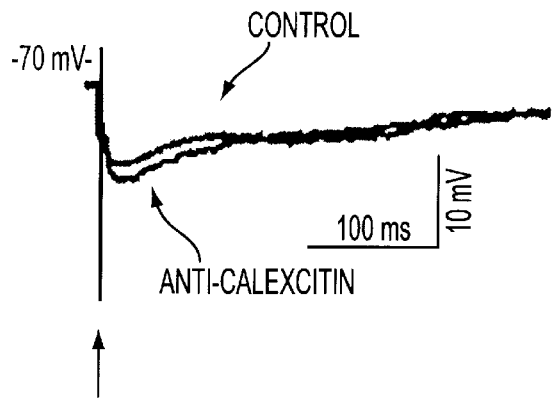
FIGS. 11A to 11E demonstrate the effects of anti-CE antibody in enhancing BAS-CA1 IPSPs, and provide potential mechanisms of CE-induced transformation of GABAergic synapses.
Figure 11B:
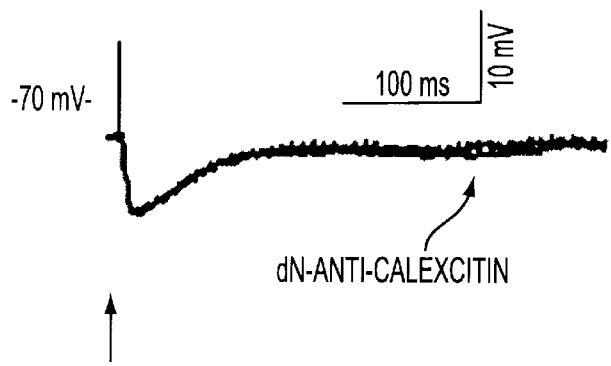
Figure 11C:
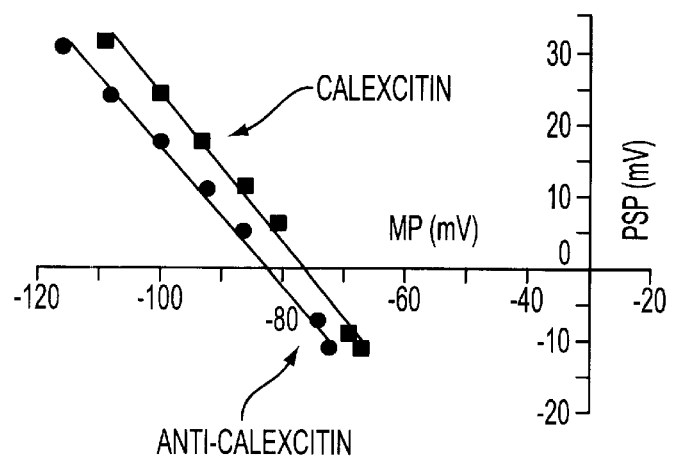
Figure 11D:
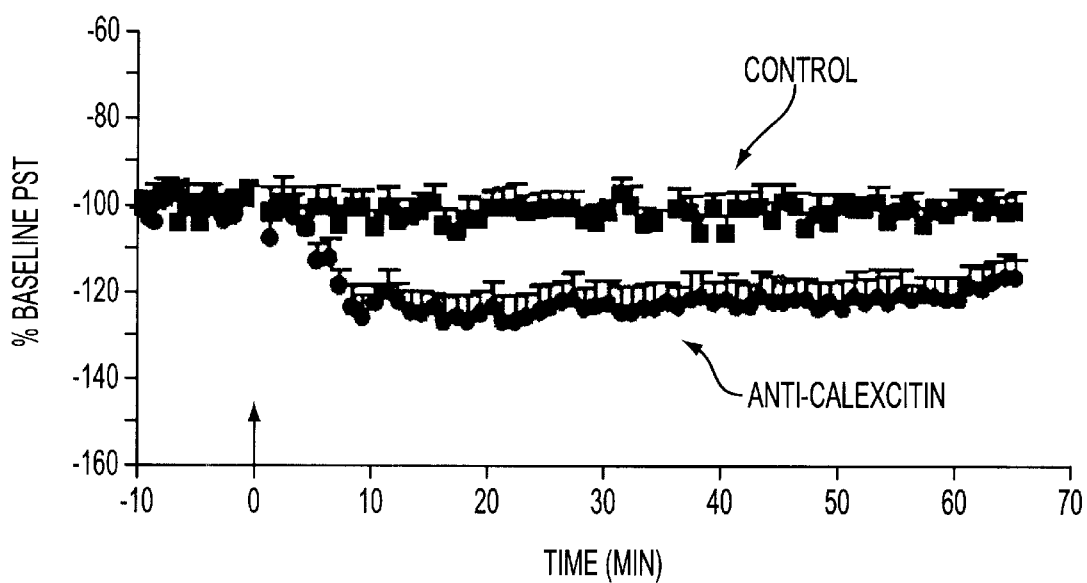

FIGS. 11A–E demonstrate that anti-CE antibody enhances BAS-CA1 IPSPs and shows mechanisms of CE-induced transformation of GABAergic synapses. Anti-CE antibody injection into a recorded CA1 pyramidal cell enhances BAS-CA1 IPSP (FIG. 11A, as compared with unmarked IPSP before injection) and elicits a shift of the PSP-MP curve to the left (FIG. 11C). Injection of heat-inactivated antibody is ineffective (FIG. 11B; two traces overlapping). Average responses of BAS-CA1 PSP after injection of either anti-CE antibody (Anti-CE) or its heat-inactivated form (Control) are shown in FIG. 11D.

A schematic drawing (FIG. 11E) shows mechanisms of CE-mediated transformation of GABAergic synapses. Synapse-transforming signals (such as associative activation of cholinergic and GABAergic inputs) turn on a CE/CE-like protein signal cascade. CE binds to the RyR and causes Ca$^{2+}$ release. The Ca$^{2+}$/CE transforms the GABAergic synapses by shifting the GABA$_A$ reversal potential from Cl$^-$ reversal potential toward HCO$_3^-$ reversal potential, through altering anion selectivity of the Cl$^-$ channels, activity of CA, and/or formation of HCO$_3^-$. Multiple arrows indicate possible involvement of unidentified mediators. AA, arachidonic acid; DAG, diacylglycerol; ER, endoplasmic reticulum; PKC, protein kinase C.

Microinjections of anti-CE antibody, which recognizes CE-like proteins in rat and rabbit cerebellum and other brain regions, including the hippocampus, into CA1 pyramidal cells produced a period of enhanced BAS-CA1 IPSPs (FIGS. 11A and D and Table 1), whereas heat-inactivated anti-CE antibody was ineffective (FIGS. 11B and D and Table 1). The difference, though small, was significant (Table 1). The anti-CE antibody-induced enhancement of BAS-CA1 IPSPs is not simply an increase in postsynaptic response for a given membrane potential. The relationship between BAS-CA1 IPSPs and membrane potential was shifted to the left (FIG. 11C). Thus, the antibody induced a significant change in the reversal potential to more negative potentials (Table 1), whereas the heat-inactivated antibody was ineffective (Table 1). The membrane input resistance was not affected by microinjection of anti-CE antibody (post-antibody: 79.0±3.2 MΩ vs. pre-antibody: 79.2±2.8 MΩ) or its heat-inactivated form post-inactive antibody: 80.7±4.1 MΩ vs. pre-inactive antibody: 80.6±3.0 MΩ). The IPSP enhancement by anti-CE antibody supports the idea that effects of CE on synaptic function are not an artificial change of synaptic function, but involve effects on endogenous substrates within the CA1 cells.

According to the invention, reducing the GABA$_A$ receptor-channel Cl$^-$ current and increasing the HCO$_3^-$ current contributes to GABA-induced depolarization (Staley, K. J., Soldo, B. L. & Proctor, W. R., Science 269, 977–981 (1995); Grover, L. M., Lambert, N. A., Schwartzkroin, P. A. & Teyler, T. J., J. Neurophysiol. 69, 1541–1555 (1993)), and the latter should be sensitive to CA inhibitors. HCO$_3^-$ formation is a slow process but is increased at least several thousand fold by CA (Dodgson, S. J., Tashian, R. E., Gros, G. & Carter, N. D. (1991). The Carbonic Anhydrases (Plenum, N.Y.)), which is present within CA1 pyramidal cells (Paternack, M., Voipio, J. & Kaila, K., Acta Physiol. Scand. 148, 229–231 (1993)). The HCO$_3^-$ reversal potential is about −12 mV (Staley et al. 1995) so that an outward flux would result (FIG. 11E) and thus depolarizes the membrane at resting membrane potentials.

Figure 12A:
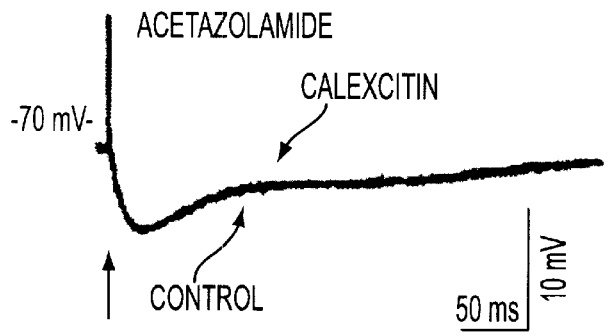
FIGS. 12A to 12K demonstrate the effects of ACET and non-bicarbonate buffer in eliminating CE-induced transformation, which converts excitatory input filter into amplifier.
Figure 12B:
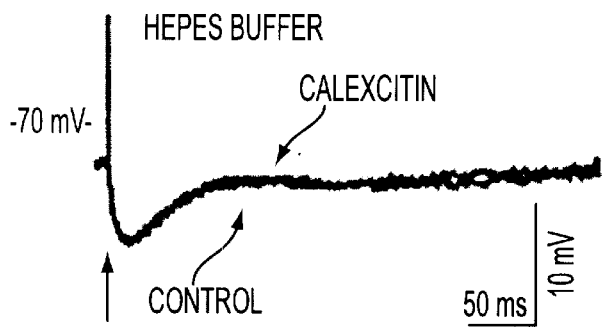
Figure 12C:
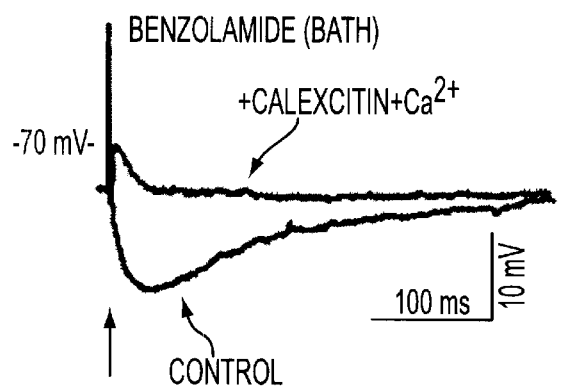
Figure 12D:
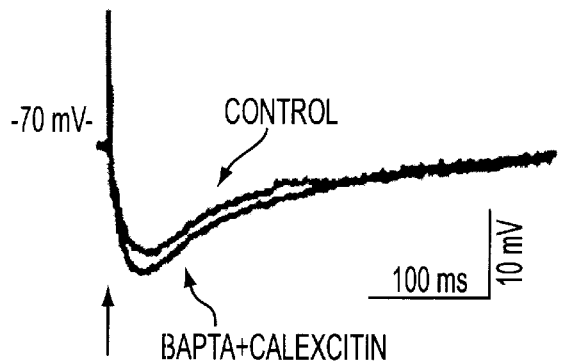
Figure 12E:
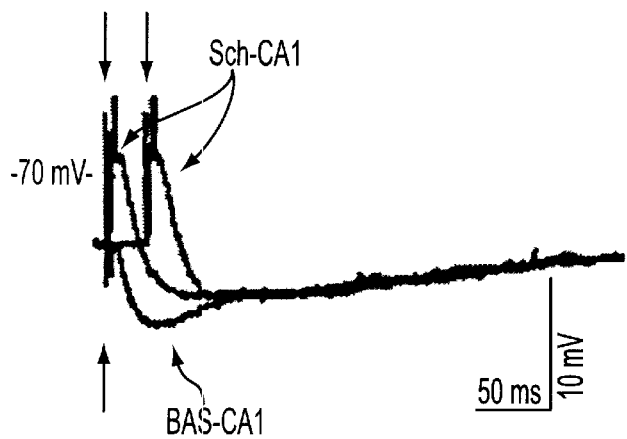
Figure 12F:
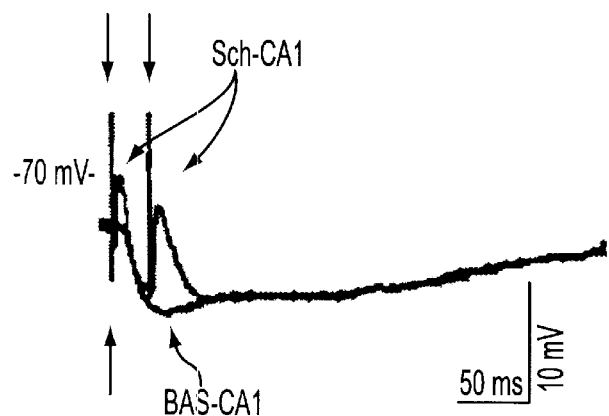
Figure 12G:
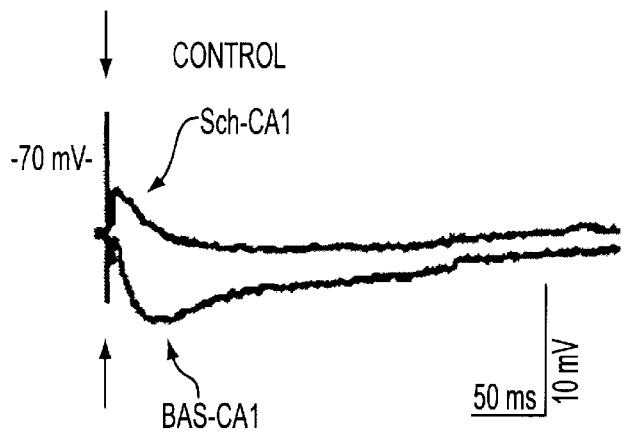
Figure 12H:
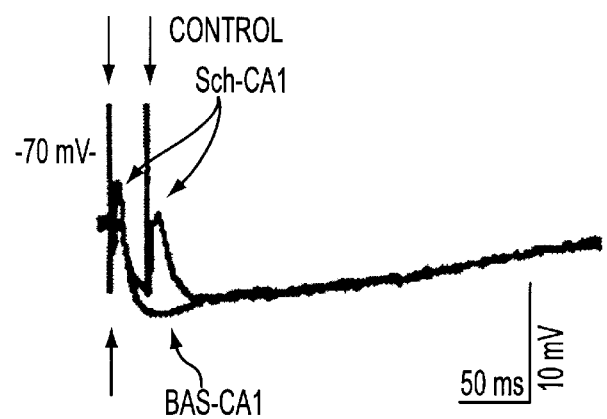
Figure 12I:
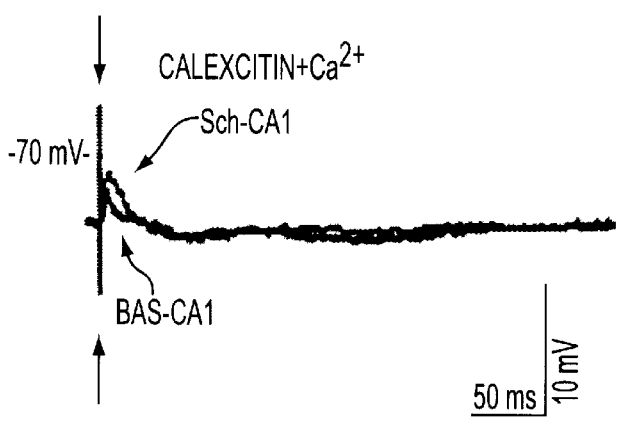
Figure 12J:
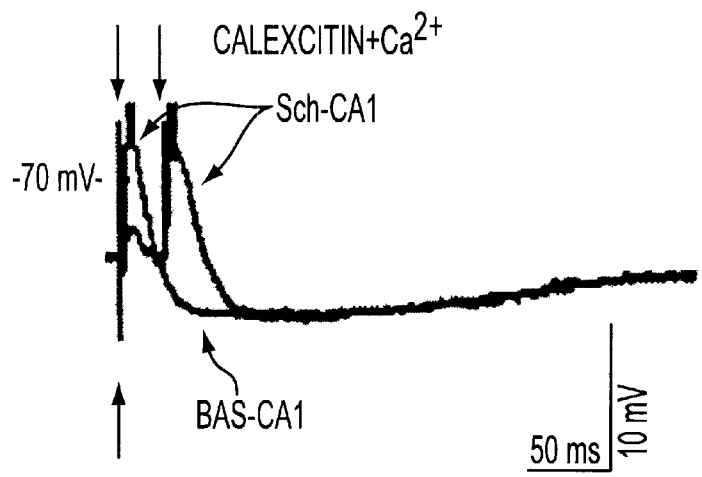

As seen in FIGS. 12A–K, ACET and non-bicarbonate buffer eliminate CE-induced transformation, and the transformation converts excitatory input filter into amplifier. ACET (1 μM) eliminates CE-induced synaptic transformation (FIG. 12A). The effect of CE on BAS-CA1 IPSPs is not observed in Hepes buffer (FIG. 12B). In the presence of extracellular benzolamide (10 μM), CE depolarization induces the synaptic transformation (FIG. 12C), which is not induced when BAPTA is co-applied (FIG. 12D; the charges carried by BAPTA are compensated by reducing the amount of acetate). Single-pulse stimulation (FIG. 12E) of BAS-CA1 evokes an IPSP and of SCH at above-threshold intensities, action potentials (truncated; two traces: one stimulated at delay of 10 ms and the other 30 ms, marked with arrows). The excitatory SCH (at the same above-threshold stimulation) input is filtered out by a costimulation of BAS-CA1 (FIG. 12F; two overlapping traces). (FIG. 12G) Single-pulse stimulation of BAS-CA1 evokes an IPSP, and stimulation of SCH at below-threshold intensities evokes an EPSP. The excitatory SCH (at the same below-threshold stimulation) input is below threshold as evoked by costimulation (single pulse) of BAS-CA1 and SCH inputs (FIG. 12H) before CE application. CE (30 min after the application) transforms BAS-CA1 IPSP and does not change much of the SCH-CA1 EPSP, evoked by single-pulse stimulation of BAS or SCH, respectively (FIG. 12I). The excitatory SCH (at the same below-threshold stimulation) input is amplified by the co-BAS stimulation after the CE-induced synaptic transformation and induces action potentials (truncated; FIG. 12J: two overlapping traces). (FIG. 12K) Schematic diagram of transformed GABAergic synapse functioning as either excitatory filter (surround) or amplifier (center). Active BAS GABAergic inputs effectively filter excitatory signals so that only very strong excitatory inputs might evoke action potentials. The GABAergic synaptic transformation results in amplifying excitatory signals so that weaker inputs can pass through the neural circuits (through the cell in the middle). BAS, basket GABAergic interneurons (in black); Pyr, CA1 pyramidal cells.

Figure 11E:
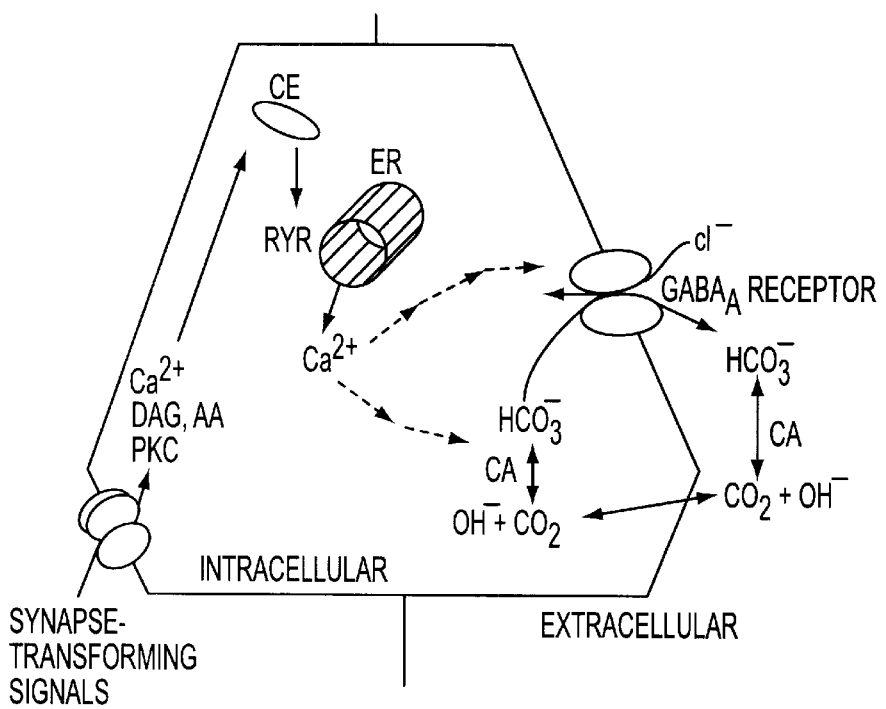

In the presence of ACET (1 $\mu$M, 30 min), a CA inhibitor, CE caused no obvious alterations in the BAS-CA1 IPSPs (FIG. 12A; $-99.2\pm3.5\%$, 30 min after CE injection as compared with $-100\%$ control value, n=8, P>0.05). CA isoforms (such as cytoplasmic types I, II, III, and VII; cell-surface membrane type IV; mitochondrial type V; and secretory type VI; Landolfi, C., Marchetti, M., Ciocci, G. & Milanese, C. J., Pharmacol. Toxicol. Methods 38, 169–172 (1997); Linskog, S. Pharmacol. Ther., 74, 1–20 (1997)) are zinc enzymes and show different sensitivity to ACET inhibition. Their activity can be regulated by hormones through cAMP in other tissues. Inhibition of probably the type II isoform ($IC_{50}=0.09$ $\mu$M for ACET; Landolfi et al. 1997), in addition to a partial inhibition of other less sensitive isoforms, appears effective in suppressing the CE effect. Bath perfusion of the membrane-impermeant CA inhibitor benzolamide (10 $\mu$M) was found to have no effects on the CE-induced synaptic transformation (FIG. 12C and Table 1), indicating that the inhibitory effects on CA were intracellular. At 10 $\mu$M (30 min), ACET itself was sufficient to transform the BAS-CA1 IPSPs, while abolishing effects of CE on the synaptic response (n=8, not shown). When non-bicarbonate buffer was perfused externally, a condition to minimize bicarbonate effects, CE did not elicit any obvious changes in BAS-CA1 IPSPs (FIG. 12B; $-98.9\pm4.2\%$, 30 min after CE injection as compared with $-100\%$ control value, n=7, P>0.05). The cellular mechanism underlying the CE-induced GABAergic synaptic transformation thus involves an induction of a depolarizing $HCO_3^-$ flux through the $GABA_A$ receptor-$Cl^-$ channel (FIG. 11E). The effectiveness of CA inhibitors and of minimizing bicarbonate influence indicates that altered $Cl^-$ accumulation through changed activity of $K^+$—$Cl^-$ transports is unlikely to be involved in the synaptic transformation. $CE/Ca^{2+}$ may induce changes in anion selectivity of the $Cl^-$ channels, activity of CA, and/or formation of $HCO_3^-$ (FIG. 11E). Ion permeability of channels has been previously shown to be modifiable by intracellular messengers or cations/anions (Williams, K., Pahk, A. J., Kashiwagi, K., Masuko, T., Nguyen, N. D. & Igarashi, K. (1998) Mol. Pharmacol. 53, 933–941; Rychkov, G. Y., Pusch, M., Roberts, M. L., Jentsch, T. J. & Bretag, A. H. (1998) J. Gen. Physiol. 111, 653–665). $Ca^{2+}$- and ATP-activated $HCO_3^-/Cl^-$ conductance has been observed in nonneuronal cells (Ishikawa, T. (1996) J. Membr. Biol. 153, 147–159). While these results strongly suggest a central role of $HCO_3^-/CA$ activity in the CE-induced synaptic transformation, CE does not appear to directly affect CA activity, as determined by measuring pH changes in the reaction for $CO_2$ conversion to bicarbonate in the presence of 4.4 nM CE, 20 $\mu$M $Ca^{2+}$, and 6.6 nM CA ($384\pm18$ mmol/min·mg of CA, n=4; as compared with $395\pm9$ mmol/min·mg of CA in the presence of 4.4 nM CE and 20 $\mu$M $Ca^{2+}$, n=6; P>0.05). Nor was CA activity in the rat whole brain homogenate affected by 4.4 nM CE and 10 $\mu$M $Ca^{2+}$ ($1.32\pm0.07$ mmol/min·mg of protein, n=2; as compared with $1.37\pm0.08$ mmol/min·mg of protein in the presence of 4.4 nM CE only, n=2; P>0.05). It thus remains to be determined what factors (coupled to CE and/or bound to $Ca^{2+}$), which would be diluted to $1/10,000$ in the brain homogenate, might affect CA and thereby mediate the responses in untreated cells. Retrograde inhibition of GABA release (Alger, B. E., Pitler, T. A., Wagner, J. J., Martin, L. A., Morishita, W., Kinov, S. A. & Lenz, R. A. (1996) J. Physiol. (London) 496, 197–209; Marty, A. & Llano, I. (1995) Curr. Opin. Neurobiol. 5, 335–341), as induced by depolarizing the membrane potential to +60 to +90 mV, might not be involved in the CE-induced inhibition of the GABAergic IPSP that follows negative current pulses used to inject CE alone. Inhibition of GABA release would not be expected to produce a reversed membrane response in polarity, nor would it be expected to be sensitive to CA inhibition or non-bicarbonate buffering. The transformed response has also been observed in response to externally applied GABA (Collin, C., Devane, W. A., Dahl, D., Lee, C. -J., Axelrod, J. & Alkon, D. L. (1995) Proc. Natl. Acad. Sci. USA 92, 10167–10171) when paired with postsynaptic depolarization. Exogenous GABA (thus not under presynaptic control) delivered in the same quantity subsequently produced depolarization rather than hyperpolarization.

CE binds to the RyR in neurons and induces intracellular $Ca^{2+}$ release, as monitored with bis-fura-2 ratiometric imaging in rat CA1 pyramidal cells (Alkon et al. 1998). We, therefore, examined whether the RyR may mediate effects of CE on BAS-CA1 synapses. RR, a membrane-impermeant polycationic molecule, inhibits the RyR with $IC_{50}$ in the nanomolar range and may alter its structure at micromolar concentrations. Its specificity is indicated by its lack of obvious effects on inositol triphosphate receptor-mediated $Ca^{2+}$ release and ensured by postsynaptic application into singly recorded pyramidal cells (5 min before CE injection). RR slightly increased the evoked BAS-CA1 IPSPs (by $16.3\%\pm4.0\%$, n=10, P<0.05), and it effectively blocked effects of CE on BAS-CA1 PSP (n=10). It neither reduced the GABAergic synaptic response nor affected postsynaptic membrane properties (n=10). Such changes would otherwise be expected if a significant amount of RR permeated (from inside the cell) the membrane to block voltage-sensitive $Ca^{2+}$ channels and presynaptic transmitter release during the experimental period. Buffering intracellular $Ca^{2+}$ with BAPTA mimicked RR in increasing the evoked BAS-CA1 IPSPs (by $17.4\%\pm3.9\%$, n=6, P<0.05; FIG. 12D) and in blocking the effects of CE postsynaptic depolarization on the BAS-CA1 PSPs (n=6). These results, together with the previously obtained observations that CE induces intracellular $Ca^{2+}$ waves in hippocampal CA1 pyramidal neurons and release $^{45}Ca^{2+}$ from microsomes (Alkon et al. 1998), indicate that CE regulates intracellular $Ca^{2+}$ levels. The effectiveness of RR and BAPTA, however, does not rule out the possibility that $Ca^{2+}$ might function as a cofactor for CE and/or other mediators to induce changes in anion selectivity of the Cl⁻ channels and activity of CA.

The BAS interneurons in CA1 are part of hippocampal networks that control the main excitatory input pathway and thus play a critical role in determination of information processing in CA1 pyramidal cells and memory storage, including transmission of the theta rhythm from septun to the hippocampus (Toth, K., Freund, T. F. & Miles, R. (1997) J. Physiol. (London) 500, 463–474). In a separate study, we observed that GABAergic synaptic transformation can be induced through associative activation of the cholinergic-GABAergic inputs into the CA1 pyramidal cells (unpublished observations). Thus, CE-induced transformation of GABAergic synapses might help determine the synaptic effect of the cholinergic system during attention to training-induced stimulus association (Fisahn, A., Pike, F. G., Buhl, E. H. & Paulsen, O. (1998) Nature (London) 394, 186–189).

Figure 12K:
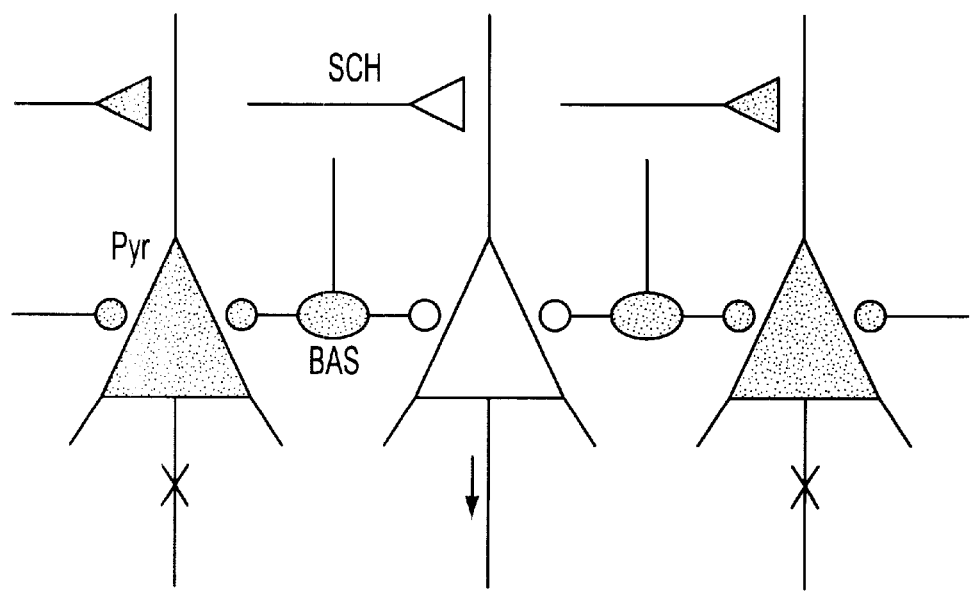

GABAergic interneurons receive excitatory inputs from SCH/commissural afferents in a feed-forward manner (Buhl et al. 1994; Cobb et al. 1995; Paulsen, O. & Moser, E. I. (1998) *Trends Neurosci.* 21, 273–278) and preferentially make synapses on cell bodies, proximal dendrites, and axon initial segments of CA1 pyramidal cells (Cobb et al. 1995; Halasy, K., Buhl, E. H., Lorinczi, Z., Tamas, G. & Somogyi, P. (1996) *Hippocampus* 6, 306–329). One BAS cell is estimated to have over 10,000 boutons innervating some 1,000 pyramidal cells (Halasy et al. 1996), forming 10–12 synapses on each pyramidal cell (Buhl et al. 1994; Cobb et al. 1995). The perisomatic termination of BAS cells is suited for synchronization of pyramidal cells (Cobb et al. 1995). Modifiability of inhibitory circuits may thus be less specific but more efficient in controlling a specific population of pyramidal cells (Cobb et al. 1995). Furthermore, the coincidence of GABAergic and the more specific glutamatergic inputs could confer great specificity in a center-surround manner (FIG. 12K). The transformed synaptic input from the BAS cells could provide a mechanism to selectively activate a subset of pyramidal neurons (those transformed and thus in the "center" of attention) and block others (those not transformed and thus in the "surround"). Activation of BAS produces fast IPSPs and reduces excitability (FIG. 12E and F) and probability of action-potential generation (Andreasen, M. & Lambert, J. D. (1998) *J. Physiol. (London)* 507, 441–462) of CA1 pyramidal cells. SCH stimulation at intensities above (30%) threshold elicits action potentials (100% of 10 trials; FIG. 12E). BAS stimulation produced an effective signal-filtering period of 50–100 ms (up to 200 ms in some cases), during which no action potential (0% of 10 trials) was evoked by SCH stimulation at the same intensities (FIG. 12F; n=9, P<0.05). Action potentials were reliably elicited (FIG. 12J; n=9) by single-pulse costimulation of SCH (at below threshold intensities) and BAS after CE-induced transformation (FIG. 12I as compare with FIG. 12G). Before the CE application, the same intensities of costimulation did not evoke action potentials (FIG. 12H; n=9). Weak signals are amplified in the transformed cells, whereas only very strong excitatory signals can successfully pass through the network under BAS inhibition. Thus, opposite GABAergic effects in subsets of neurons could act as either filter or amplifier, increasing the signal-to-noise ratio of relevant information, that is in the focused center of attention (FIG. 12K).

Discussion

Transformation of GABAergic inhibitory into excitatory synaptic potentials has been observed experimentally by several groups, with transformed response lasting either for a short term (seconds) to minutes. (Staley et al. 1995; Wong, R. K. S. & Watkins, D. J. (1982) *J. Neurophysiol.* 48, 938–951; Kalia, K., Larnsa, K., Smimov, S., Taira, T. & Voipio, J. (1997) *J. Neurosci.* 17, 7662–7672; Taira, T., Lamsa, K. & Kaila, K. (1997) *J. Neurophysiol.* 77, 2213–2218) or long period (≧1 hr; 20; Alkon, D. L., Sanchez-Andres, J. -V., Ito, E., Oka, K., Yoshioka, T. & Collin, C. (1992) *Proc. Natl. Acad. Sci. USA* 89, 11862–11866; Alkon, D. L., Lederhendler, I. & Soukimas, J. J. (1992) *Science* 215, 693–695). While fascinating and important because the transformation results in a novel synaptic response, its role in memory, and the intracellular signaling cascades that lead to the synaptic transformation were previously unknown. The present study provides evidence that lasting changes in synaptic polarity can be orchestrated by CE, an associative memory-related signal protein (Alkon et al. 1998; Nelson et al. 1990). CE switches GABAergic synaptic function from excitation filter to amplifier and may help control hippocampal networks and hippocampus-dependent memory processing.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A method of suppressing or enhancing attentive cognition in a mammal in need thereof comprising administering to the mammal a compound that modulates carbonic anhydrase activity in the brain in an amount sufficient to suppress or enhance attentive cognition.

2. The method of claim 1, wherein the compound inhibits carbonic anhydrase activity in the brain and suppresses attentive cognition.

3. The method of claim 2, wherein the compound is selected from the group consisting of acetazolamide, benzolamide, and analogs thereof.

4. The method of claim 2, wherein the compound prevents establishment of a theta rhythm.

5. The method of claim 2, wherein the compound prevents formation of associative memory.

6. The method of claim 2 wherein the suppression of attentive cognition is specific.

7. The method of claim 1 wherein the compound modulates intraneuronal carbonic anhydrase activity.

8. The method of claim 1, wherein the compound modulates extraneuronal carbonic anhydrase activity.

9. The method of claim 1, wherein the compound alters neuronal $HCO_3^-$ conductance.

10. The method of claim 1, wherein the compound modulates a neuronal $HCO_3^-$ current relative to neuronal $Cl^-$ and/or $K^+$ currents.

11. The method of claim 1, wherein the compound strengthens theta rhythm in the mammal.

12. The method of claim 1, wherein the compound promotes synaptic transformation in the mammal.

13. The method of claim 1, wherein the compound increases or decreases bicarbonate-mediated GABAergic depolarization.

14. A method of improving attentive cognition in a patient in need thereof comprising administering to the patient a compound that stimulates carbonic anhydrase activity in the brain in an amount sufficient to improve attentive cognition.

15. The method of claim 14, wherein the patient has no neurodegenerative disease or disorder.

16. The method of claim 14, wherein the patient suffers from a neurodegenerative disease or disorder.

17. The method of claim 14, wherein the compound stimulates intraneuronal carbonic anhydrase activity.

18. A method for treating a neurological disease or disorder in a mammal comprising administering to the mammal a stimulator of brain carbonic anhydrase activity in an amount effective to improve attentive cognition.

19. The method of claim 18, wherein attention and/or memory acquisition is enhanced.

20. The method of claim 18, wherein the neurological disease or disorder is selected from dementia, stroke, hypoxia, and ischemia.

21. A method of stimulating synaptic transformation of inhibitory postsynaptic potentials into excitatory postsynaptic potentials in GABAergic synapses in a mammalian brain, comprising administering to the brain an activator of intraneuronal carbonic anhydrase activity, thereby stimulating the synaptic transformation in the synapses.

22. The method of claim 21, wherein the synapses are in pyramidal cells in the hippocampal region.

23. A method of blocking synaptic transformation of inhibitory postsynaptic potentials into excitatory postsynaptic potentials in GABAergic synapses in a mammalian brain, comprising determining a need for blocking, and administering to the brain an inhibitor of intraneuronal carbonic anhydrase activity, thereby blocking the synaptic transformation in the synapses.

24. The method of claim 23, wherein the inhibitor neutralizes the excitatory effects of calexcitin.

25. The method of claim 23, wherein the inhibitor is acetazolamide or an analog of acetazolamide.

26. The method of claim 23, wherein the synapses are in pyramidal cells in the hippocampal region.

* * * * *